(12) United States Patent
Nishi et al.

(10) Patent No.: US 7,910,617 B2
(45) Date of Patent: Mar. 22, 2011

(54) METHOD FOR SUPPRESSING THE NUMBER OF PERIPHERAL BLOOD LYMPHOCYTES USING AN AMINO ALCOHOL COMPOUND

(75) Inventors: Takahide Nishi, Tokyo (JP); Toshiyasu Takemoto, Tokyo (JP); Shojiro Miyazaki, Tokyo (JP); Takaichi Shimozato, Miura-shi (JP); Futoshi Nara, Yachiyo (JP); Takashi Izumi, Kawasaki (JP)

(73) Assignee: Sankyo Company, Limited, Tokyo (JP)

( * ) Notice: Subject to any disclaimer, the term of this patent is extended or adjusted under 35 U.S.C. 154(b) by 1246 days.

(21) Appl. No.: 10/588,818

(22) PCT Filed: Feb. 23, 2005

(86) PCT No.: PCT/JP2005/002884
§ 371 (c)(1),
(2), (4) Date: Aug. 23, 2006

(87) PCT Pub. No.: WO2005/079788
PCT Pub. Date: Sep. 1, 2005

(65) Prior Publication Data
US 2007/0191468 A1    Aug. 16, 2007

(30) Foreign Application Priority Data
Feb. 24, 2004   (JP) .................. 2004-048205

(51) Int. Cl.
*A61K 31/40* (2006.01)
(52) U.S. Cl. ...................................... 514/423
(58) Field of Classification Search ............ 514/423
See application file for complete search history.

(56) References Cited

U.S. PATENT DOCUMENTS

| | | |
|---|---|---|
| 3,726,948 A | 4/1973 | Botts |
| 4,363,918 A | 12/1982 | Albert et al. |
| 4,386,090 A | 5/1983 | Moinet et al. |
| 4,536,601 A | 8/1985 | Tukamoto et al. |
| 4,613,596 A | 9/1986 | Moroni |
| 4,634,689 A | 1/1987 | Witkowski et al. |
| 4,667,038 A | 5/1987 | Clark et al. |
| 4,716,155 A | 12/1987 | Karanewsky et al. |
| 4,792,568 A | 12/1988 | Auerbach |
| 4,888,338 A | 12/1989 | Godfroid et al. |
| 4,977,171 A | 12/1990 | Suzuki et al. |
| 5,002,966 A | 3/1991 | Skidmore et al. |
| 5,037,853 A | 8/1991 | Brooks et al. |
| 5,037,958 A | 8/1991 | Hashimoto et al. |
| 5,039,706 A | 8/1991 | Wilkerson |
| 5,061,704 A | 10/1991 | Wierzbicki et al. |
| 5,068,247 A | 11/1991 | Fujita et al. |
| 5,112,848 A | 5/1992 | Brooks et al. |
| 5,130,487 A | 7/1992 | Budai et al. |
| 5,135,947 A | 8/1992 | Robertson et al. |
| 5,177,085 A | 1/1993 | Naef |
| 5,219,884 A | 6/1993 | Fujita et al. |
| 5,234,934 A | 8/1993 | Budai et al. |
| 5,260,329 A | 11/1993 | Mongelli et al. |
| 5,266,599 A | 11/1993 | Aubard et al. |
| 5,276,190 A | 1/1994 | Boesten et al. |
| 5,288,751 A | 2/1994 | Brooks et al. |
| 5,387,514 A | 2/1995 | Schudok et al. |
| 5,433,896 A | 7/1995 | Kang et al. |
| 5,470,878 A | 11/1995 | Michnick et al. |
| 5,501,980 A | 3/1996 | Katerinopoulos et al. |
| 5,534,539 A | 7/1996 | Mongelli et al. |
| 5,573,909 A | 11/1996 | Singer et al. |
| 5,604,229 A | 2/1997 | Fujita et al. |
| 5,641,783 A | 6/1997 | Klein et al. |
| 5,686,479 A | 11/1997 | Okumoto et al. |
| 5,714,605 A | 2/1998 | Vazquez et al. |
| 5,719,176 A | 2/1998 | Fujita et al. |
| 5,723,218 A | 3/1998 | Haugland et al. |
| 5,837,703 A | 11/1998 | Kumar et al. |
| 5,891,892 A | 4/1999 | Cheng et al. |
| 5,922,770 A | 7/1999 | Peschke et al. |
| 5,948,820 A | 9/1999 | Fujita et al. |
| 5,952,316 A | 9/1999 | Fujita et al. |
| 6,004,565 A | 12/1999 | Chiba et al. |
| 6,013,802 A | 1/2000 | Hoyland et al. |
| 6,028,098 A | 2/2000 | Goodman et al. |
| 6,077,954 A | 6/2000 | Cook et al. |
| 6,121,329 A | 9/2000 | Fujii et al. |
| 6,187,821 B1 | 2/2001 | Fujita et al. |
| 6,214,873 B1 | 4/2001 | Adachi et al. |
| 6,277,888 B1 | 8/2001 | Sakai et al. |
| 6,284,915 B2 | 9/2001 | Hirase et al. |
| 6,372,800 B1 | 4/2002 | Fujita et al. |
| 6,437,165 B1 | 8/2002 | Mandala et al. |
| 6,444,686 B1 | 9/2002 | Ko et al. |
| 6,455,528 B1 | 9/2002 | Adachi et al. |
| 6,462,092 B1 | 10/2002 | Sikorski et al. |
| 6,468,998 B1 | 10/2002 | Kuroita et al. |

(Continued)

FOREIGN PATENT DOCUMENTS

EP    0 125 315 A1    11/1984

(Continued)

OTHER PUBLICATIONS

English-language International Preliminary Report on Patentability dated Sep. 19, 2006 for International application PCT/JP2005/002884 filed Feb. 23, 2005; Applicant: Sankyo Company, Limited et al.

(Continued)

*Primary Examiner* — Phyllis G Spivack
*Assistant Examiner* — Nelson C Blakely, III
(74) *Attorney, Agent, or Firm* — Holtz, Holtz, Goodman & Chick, P.C.

(57) ABSTRACT

A method for suppressing the number of peripheral blood lymphocytes involving administering to a human in need thereof a pharmaceutically effective amount of a compound which is (2R) -2-amino-2-methyl-4-{1-methyl-5-[4-(4-methylphenyl)butanoyl]pyrrol-2-yl}butan-1-ol or a pharmacologically acceptable salt thereof, such as the hydrochloride salt.

6 Claims, No Drawings

U.S. PATENT DOCUMENTS

| | | | |
|---|---|---|---|
| 6,476,004 B1 | 11/2002 | Sakai et al. | |
| 6,476,075 B1 | 11/2002 | Sikorski et al. | |
| 6,525,069 B1 | 2/2003 | Ko et al. | |
| 6,605,744 B2 | 8/2003 | Abel et al. | |
| 6,630,492 B1 | 10/2003 | Bauer et al. | |
| 6,630,493 B1 | 10/2003 | Lubisch et al. | |
| 6,638,950 B2 | 10/2003 | Duncia et al. | |
| 6,649,611 B2 | 11/2003 | Blumberg et al. | |
| 6,667,025 B2 | 12/2003 | Chiba et al. | |
| 6,677,375 B2 | 1/2004 | Sikorski et al. | |
| 6,683,099 B2 | 1/2004 | Sikorski et al. | |
| 6,686,353 B1 | 2/2004 | Shiota et al. | |
| 6,765,023 B2 | 7/2004 | Sikorski et al. | |
| 6,964,976 B2 | 11/2005 | Nishi et al. | |
| 7,199,150 B2 | 4/2007 | Nishi et al. | |
| 2002/0052349 A1 | 5/2002 | Krauss et al. | |
| 2002/0086832 A1* | 7/2002 | Budd et al. | 514/18 |
| 2002/0091105 A1 | 7/2002 | Mandala et al. | |
| 2003/0216393 A1 | 11/2003 | Buschmann et al. | |
| 2003/0220390 A1 | 11/2003 | Buschmann et al. | |
| 2003/0236297 A1 | 12/2003 | Nishi et al. | |
| 2004/0034063 A1 | 2/2004 | Ko et al. | |
| 2004/0058894 A1 | 3/2004 | Doherty et al. | |
| 2004/0082790 A1 | 4/2004 | Duncia et al. | |
| 2004/0092603 A1 | 5/2004 | Chiba et al. | |
| 2004/0097508 A1 | 5/2004 | Lubisch et al. | |
| 2004/0132784 A1 | 7/2004 | Nishi et al. | |
| 2004/0242654 A1 | 12/2004 | Kohno et al. | |
| 2004/0254222 A1 | 12/2004 | Kohno et al. | |
| 2005/0043386 A1 | 2/2005 | Nishi et al. | |
| 2007/0105933 A1 | 5/2007 | Nishi et al. | |
| 2007/0142335 A1 | 6/2007 | Nishi et al. | |
| 2007/0149597 A1 | 6/2007 | Nishi et al. | |

FOREIGN PATENT DOCUMENTS

| | | |
|---|---|---|
| EP | 0 167 459 B1 | 1/1986 |
| EP | 0 297 782 A1 | 1/1989 |
| EP | 0 300 688 A1 | 1/1989 |
| EP | 0 480 659 B1 | 4/1992 |
| EP | 0 520 336 A2 | 12/1992 |
| EP | 0 627 406 A1 | 12/1994 |
| EP | 0 778 263 A1 | 6/1997 |
| EP | 1 002 792 A1 | 5/2000 |
| EP | 1 050 301 A1 | 11/2000 |
| EP | 1 176 140 B1 | 1/2002 |
| EP | 1 201 236 A1 | 5/2002 |
| EP | 1300405 A1 | 4/2003 |
| EP | 1 319 651 A2 | 6/2003 |
| EP | 1 431 275 A1 | 6/2004 |
| EP | 1 431 284 A1 | 6/2004 |
| EP | 1471054 A1 | 10/2004 |
| GB | 1 134 687 | 11/1968 |
| GB | 2 022 085 A | 12/1979 |
| GB | 2 054 588 A | 2/1981 |
| JP | 58-105946 A | 6/1983 |
| JP | 59-44345 A | 3/1984 |
| JP | 62-123126 A | 6/1987 |
| JP | 63-139179 A | 6/1988 |
| JP | 1-104087 A | 4/1989 |
| JP | 2-256612 A | 10/1990 |
| JP | 3-246264 A | 11/1991 |
| JP | 4-104796 A | 4/1992 |
| JP | 5-294907 A | 11/1993 |
| JP | 6-067229 A | 3/1994 |
| JP | 6-345728 A | 12/1994 |
| JP | 7-002665 A | 1/1995 |
| JP | 7-138230 A | 5/1995 |
| JP | 9-124564 A | 5/1997 |
| JP | 10-81623 A | 3/1998 |
| JP | 11-80026 A | 3/1999 |
| JP | 11-310556 A | 11/1999 |
| JP | 11-343300 A | 12/1999 |
| JP | 2002-053575 A | 2/2002 |
| JP | 2002-316985 A | 10/2002 |
| JP | 2003-267974 A | 9/2003 |
| JP | 2005-41867 A | 2/2005 |
| WO | WO 93/09185 A1 | 5/1993 |
| WO | WO 94/08943 A1 | 4/1994 |
| WO | WO 96/06068 A1 | 2/1996 |
| WO | WO 98/15278 A1 | 4/1998 |
| WO | WO 98/22100 A2 | 5/1998 |
| WO | WO 98/45249 A1 | 10/1998 |
| WO | WO 00/27798 A1 | 5/2000 |
| WO | WO 00/33836 A1 | 6/2000 |
| WO | WO 00/53569 A1 | 9/2000 |
| WO | WO 01/01978 A1 | 1/2001 |
| WO | WO 01/08685 A1 | 2/2001 |
| WO | WO 01/49663 A2 | 7/2001 |
| WO | WO 01/49685 A2 | 7/2001 |
| WO | WO 02/06268 A1 | 1/2002 |
| WO | WO 02/18395 A1 | 3/2002 |
| WO | WO 02/067915 A1 | 9/2002 |
| WO | WO 02/076995 A2 | 10/2002 |
| WO | WO 02/094342 A2 | 11/2002 |
| WO | WO 03/009836 A2 | 2/2003 |
| WO | WO 03/013509 A1 | 2/2003 |
| WO | WO 03/029205 A1 | 4/2003 |
| WO | WO 03/035068 A1 | 5/2003 |
| WO | WO 03/044015 A2 | 5/2003 |
| WO | WO 03/059880 A1 | 7/2003 |
| WO | WO 03/097028 A1 | 11/2003 |
| WO | WO 2004/024673 A1 | 3/2004 |
| WO | WO 2004/028521 A2 | 4/2004 |

OTHER PUBLICATIONS

Cativiela et al., "Stereoselective synthesis of quaternary α-amino acids, Part 1: Acyclic compounds", *Tetrahedron: Asymmetry*, 9, pp. 3517-3599 (1998).

Gander-Coquoz et al., "Synthesis of Enantiomercially Pure, α-Alkylated Lysine, Ornithine, and Tryptophan Derivatives", *Helvetica Chimica Acta.*, 71, pp. 224-236, (1988).

Sano et al., "Lewis Acid- and Cationic Lithium-Mediated Diastereoselective Aldol-Type Reaction Based on a Double Chiral Recognition Manner for the Asymmetric Synthesis of α-Substituted Serines", *Tetrahedron Letters*, 36, No. 23, pp. 4101-4104 (1995).

Nagao et al., "Efficient Preparation of New Chiral Synthons Useful for (+)-Carbacyclin Synthesis by Utilizing Enzymatic Hydrolysis", *Chemistry Letters*, pp. 239-242 (1989).

Tamai et al., Enzymatic Hydrolyses of the ó-Symmetric Dicarboxylic Diesters Bearing a Sulfinyl Group as the Prochiral Center, *Chemistry Letters*, pp. 2381-2384 (1994).

Casarrubio et al., "On the Syntheses of Thiophene Analogs of Practolol and 'Reversed' Practolol", *J. Heterocyclic Chem.*, 20, 1557-1560 (1983).

Charette et al., "Syntheses of α, α-Disubstituted-α-Amino Acids by Double Nucleophilic Addition to Cyanohydrins", *Tetrahedron Letters*, 39, 5147-5150 (1998).

Adachi et al., "Design, Synthesis, and Structure-Activity Relationships of 2-Substituted-2-Amino-1,3-Propanediols: Discovery of a Novel Immunosuppressant, FTY720," *Bioorganic & Medicinal Chemistry Letters*, vol. 5, No. 8, pp. 853-856, 1995.

Chiba et al., "FTY720: Immunosuppressant," *Drugs of the Future*, 22(1):18-22 (1997).

Constantinou-Kokotou et al., "Synthesis of optically active lipidic α-amino acids and lipidic 2-amino alcohols," *Amino Acids*, (1999) 16:273-285.

Constantinou-Kokotou et al., "Synthesis and biological activities of long chain 2-amino alcohols," *Letters in Peptide Science*, 9:143-152, 2002.

Dagan et al., "Synthetic, non-natural sphingolipid analogs inhibit the biosynthesis of cellular sphingolipids, elevate ceramide and induce apoptotic cell death," *Biochimica et Biophysica Acta*, 1633 (3) :161-169 (2003).

Fujita et al., "Simple Compounds, 2-Alkyl-2-Amino-1,3-Propanediols Have Potent Immunosuppressive Activity," *Bioorganic & Medicinal Chemistry Letters*, vol. 5, No. 8, pp. 847-852, 1995.

Fujita et al., 2-Substituted 2-Aminoethanol: Minimum Essential Structure for Immunosuppressive Activity of ISP-I (Myriocin), *Bioorganic & Medicinal Chemistry Letters*, vol. 5, No. 16, pp. 1857-1860, 1995.

Fujita et al., "2-Aminoalcohol: Minimum essential structure of immunosuppressive activity of ISP-I (myriocin)," *Tennen Yuki Kagobutsu Toronkai Koen Yoshisyu*, 38:727-732 (1996).

Fujita et al., "Potent Immunosuppressants, 2-Alkyl-2-aminopropane-1,3-diols," *J. Med. Chem.*, 1996, 39, 4451-4459.

Fujita et al., "Design of Novel Immunosuppressants Based on Fungal Metabolites," *International Symposium on Natural Medicines*, PL-1, p. 3-4, 1997, Kyoto, Japan.

Hinterding et al., "Synthesis of Chiral Analogues of FTY720 and its Phosphate," *Synthesis 2003*, No. 11, 1667-1670, 2003.

Hinterding et al., "First asymmetric synthesis of chiral analogues of the novel immunosuppressant FTY720," *Tetrahedron Letters*, 43 (2002) 8095-8097.

Hirose et al., "2-Aminoalcohol Immunosuppressants: Structure-Activity Relationships," *Bioorganic & Medicinal Chemistry Letters*, vol. 6, No. 22, pp. 2647-2650, 1996.

Kley et al., "Synthesis and PLA$_2$-Inhibitory Properties of 2 (R) -Acetamido-Alkylphosphomethanols with a Variable Aggregate Anchor," *Bioorganic & Medicinal Chemistry Letters*, 9 (1999) 261-264.

Maier et al., "Organic Phosphorus Compounds 93. Preparation, Properties and Herbicidal Activity of 2-Substituted 5-Phenoxy- and 5-Pyridyloxy-Phenylaminoalkyl-Phosphonic- and -Phosphinic Acid—as well as—Phosphine Oxide Derivatives," *Phosphorus, Sulfur and Silicon*, 56 (1-4) : 5-15 (1991).

U.S. Appl. No. 11/922,429 deposited Dec. 18, 2007, Confirmation No. 6507.

Xiao-Ru Huang et al., "Th1 responsiveness to nephritogenic antigens determines susceptibility to crescentic glomerulonephritis in mice," *Kidney International*, vol. 51, (1997), pp. 94-103.

Monique A. Berman et al., "Decreased IL-4 Production in new Onset Type 1 Insulin-Dependent Diabetes Mellitus," *The Journal of Immunology*, vol. 157, 4691 (1996).

Supplementary European Search Report dated May 27, 2010 for EP 05710577.

English-language summary of Nov. 27, 2009 Office Action in Colombian Application No. 06083976.

* cited by examiner

METHOD FOR SUPPRESSING THE NUMBER OF PERIPHERAL BLOOD LYMPHOCYTES USING AN AMINO ALCOHOL COMPOUND

This application is a United States national phase application of International Application PCT/JP2005/002884, filed Feb. 23, 2005.

TECHNICAL FIELD

The present invention relates to an amino alcohol compound having superior immunosuppressive activity or a pharmacologically acceptable salt thereof, and to a pharmaceutical composition having peripheral blood lymphocyte count lowering activity that demonstrates superior physical properties and pharmacokinetics.

BACKGROUND ART

Conventionally in the treatment of immunity-related diseases such as rheumatoid arthritis and other autoimmune diseases, anti-inflammatory drugs such as steroids have been used against inflammatory reactions caused by an abnormal immune response. However, this treatment is merely a nosotropic therapy, and does not constitute a fundamental cure.

In addition, whilst abnormalities of the immune system have also been reported to be involved in the onset of diabetes and nephritis (see, for example, Non-Patent Document 1), a drug has yet to be developed capable of correcting these abnormalities.

On the other hand, development of a method for suppressing the immune response is extremely important for preventing rejection reactions during organ and cell transplants, and for treating and preventing various autoimmune diseases. However, conventionally known immunosuppressants such as Cyclosporin A (CsA) and Tacrolimus (TRL) are known to demonstrate toxicity to the kidneys and liver, and although therapies combining their use with steroids are widely used to diminish such adverse side effects, these drugs are still unable to demonstrate adequate immunosuppressive effects without causing adverse side effects.

In view of these circumstances, attempts have been made to discover compounds having low toxicity and superior immunosuppressive activity.

The following lists examples of known immunosuppressants.

(1) A compound of the general formula (a) is known as an immunosuppressant (see, for example, Patent Document 1):

[Chemical Formula 1]

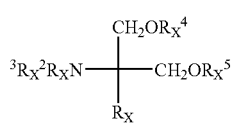

(a)

{in compound (a), $R_x$ represents an optionally substituted, linear or branched carbon chain [which may have a double bond, triple bond, oxygen, sulfur, $-N(R_x^6)-$ group (wherein $R_x^6$ represents hydrogen), optionally substituted arylene or optionally substituted heteroarylene, and may have optionally substituted aryl, optionally substituted cycloalkyl or optionally substituted heteroaryl on the end of said chain]; and $R_x^2$, $R_x^3$, $R_x^4$ and $R_x^5$ may be the same or different and represent hydrogen or alkyl}.

Although compound (a) of the prior art has as essential substituents two oxymethyl groups substituted on the same carbon atom (namely, $-CH_2OR_x^4$ and $-CH_2OR_x^5$), the compound of the present invention differs from compound (a) in that it has a $-CH_2OH$ group and a methyl or ethyl group substituted on the same carbon atom as the corresponding groups thereto.

(2) A compound of the general formula (b) is known as an immunosuppressant (see, for example, Patent Document 2):

[Chemical Formula 2]

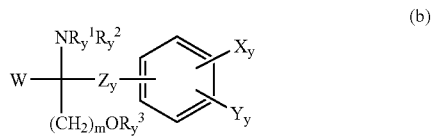

(b)

[in compound (b), $R_y^1$, $R_y^2$ and $R_y^3$ represent a hydrogen atom or the like, W represents a hydrogen atom, an alkyl group or the like, $Z_y$ represents a single bond or an alkylene group; $X_y$ represents a hydrogen atom or an alkoxy group, and $Y_y$ represents a hydrogen atom, an alkyl group, an alkoxy group, an acyl group, an acyloxy group, an amino group, an acylamino group or the like].

Although it is essential that compound (b) has a phenyl group in its basic backbone, the compound contained in the pharmaceutical composition of the present invention differs from compound (b) in that the corresponding group is a heterocyclic group in the form of a pyrrole group having a substituent on the nitrogen atom.

Moreover, a compound having a structure that resembles the structure of the compound contained in the pharmaceutical composition of the present invention is not disclosed whatsoever in this publication.

(3) A compound of the general formula (c) is known as an immunosuppressant (see, for example, Patent Document 3):

[Chemical Formula 3]

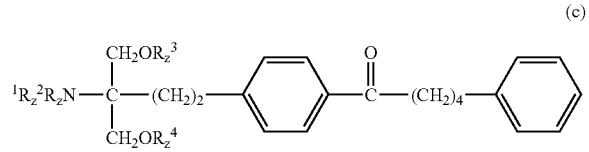

(c)

[in compound (c), $R_z^1$, $R_z^2$, $R_z^3$ and $R_z^4$ may be the same or different, and represent a hydrogen atom or an acyl group].

Although compound (c) has two oxymethyl groups (namely, $-CH_2OR_z^3$ and $-CH_2OR_z^4$) substituted on the same carbon atom as essential substituents, the compound of the present invention differs from compound (c) in that it has a $-CH_2OH$ group and a methyl or ethyl group substituted on the same carbon atom as the corresponding groups thereto. In addition, although compound (c) has an essential group in the form of a phenyl group between the $-(CH_2)_2-$ group and $-CO-(CH_2)_4-$ group in the basic backbone thereof, the compound contained in the pharmaceutical composition of the present invention differs from compound (c) in that the corresponding group is a heterocyclic group in the form of a pyrrole group having a substituent on the nitrogen atom.

(4) A compound of the general formula (d) is known as an immunosuppressant (see, for example, Patent Documents 4 and 5):
[Chemical Formula 4]

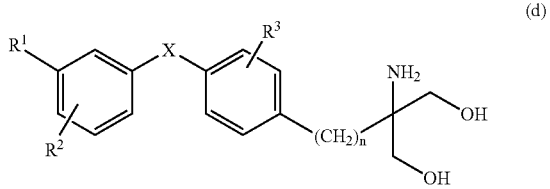

[in compound (d), $R^1$ represents a halogen atom, a trihalomethyl group, a hydroxyl group, a lower alkyl group having 1 to 7 carbon atoms, a phenoxymethyl group or the like; $R^2$ represents a hydrogen atom, a halogen atom, a trihalomethyl group or the like; X represents O, S, SO or $SO_2$; and n represents an integer of 1 to 4].

Although compound (d) has two oxymethyl groups ($-CH_2OH$) substituted on the same carbon atom as essential substituents, the compound of the present invention differs from compound (d) in that it has a $-CH_2OH$ group and a methyl or ethyl group substituted on the same carbon atom as the corresponding groups thereto. In addition, although compound (d) has a substituted phenyl group in its basic backbone as an essential group, the compound contained in the pharmaceutical composition differs from compound (d) in that the corresponding group is a heterocyclic group in the form of a pyrrole group having a substituent on the nitrogen atom.

On the other hand, a compound of the general formula (e) that has immunosuppressive activity is disclosed by the present applicant in Japanese Patent Application (Kokai) No. 2002-167382 (Patent Document 6):
[Chemical Formula 5]

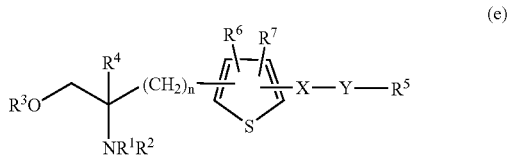

[wherein $R^1$ and $R^2$ represent a hydrogen atom or an amino protecting group; $R^3$ represents a hydrogen atom or a hydroxyl protecting group; $R^4$ represents a lower alkyl group; n represents an integer of 1 to 6; X represents an ethylene group, Y represents a $C_1$-$C_{10}$ alkylene group; $R^5$ represents an aryl group or substituted aryl group; and $R^6$ and $R^7$ represent a hydrogen atom].

In addition, a compound of the general formula (f) that has immunosuppressive activity is disclosed by the present applicant in Japanese Patent Application (Kokai) No. 2003-267950 (Patent Document 7):
[Chemical Formula 6]

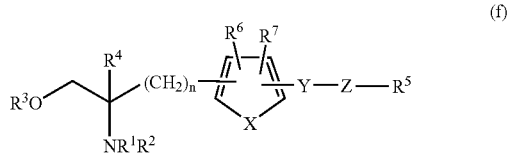

[wherein $R^1$ and $R^2$ represent a hydrogen atom, an amino protecting group or the like; $R^3$ represents a hydrogen atom or a hydroxyl protecting group; $R^4$ represents a lower alkyl group; n represents an integer of 1 to 6; X represents an oxygen atom or an unsubstituted nitrogen atom or a nitrogen atom substituted with a lower alkyl group or the like; Y represents an ethylene group or the like; Z represents an alkylene group having 1 to 10 carbon atoms or the like; $R^5$ represents an aryl group or substituted aryl group or the like; and $R^6$ and $R^7$ represent a hydrogen atom or the like].

In view of these circumstances, it is desired to discover a pharmaceutical composition having low toxicity and superior immunosuppressive activity.

[Patent Document 1] International Publication WO94/08943 (EP627406)
[Patent Document 2] International Publication WO96/06068
[Patent Document 3] International Publication WO98/45249
[Patent Document 4] International Publication WO03/029184
[Patent Document 5] International Publication WO03/029205
[Patent Document 6] Japanese Patent Application (Kokai) No. 2002-167382
[Patent Document 7] Japanese Patent Application (Kokai) No. 2003-267950
[Non-Patent Document 1] Kidney International, vol.51, 94 (1997); Journal of Immunology, vol. 157, 4691 (1996)

DISCLOSURE OF THE INVENTION

Problem to be Solved by the Invention

As a result of conducting extensive studies over many years on pharmaceutical compositions, the present inventors found a novel pharmaceutical composition having low toxicity and superior immunosuppressive activity, that is useful against rejection reactions during various organ transplants or skin transplants, autoimmune diseases or other immunity-related diseases such as systemic lupus erythematosus, rheumatoid arthritis, polymyositis, fibrositis, skeletal myositis, arthrosteitis, osteoarthritis, dermatomyositis, scleroderma, Behcet's disease, Crohn's disease, ulcerative colitis, autoimmune hepatitis, aplastic anemia, idiopathic thrombocytopenic purpura, autoimmune hemolytic anemia, multiple sclerosis, autoimmune pomphus, psoriasis vulgaris, angiitis, Wegener's granuloma, uveitis, Sjogren's syndrome, idiopathic interstitial pneumonia, Goodpasture's syndrome, sarcoidosis, allergic granulomatous angiitis, bronchial asthma, myocarditis, cardiomyopathy, aortitis syndrome, postmyocardial infarction syndrome, primary pulmonary hypertension, lipoid nephrosis, membranous nephropathy, membranoproliferative glomerulonephritis, focal glomerular sclerosis, crescenteric nephritis, myasthenia gravis, inflammatory neuropathy, atopic dermatitis, chronic photosensitive dermatitis, hyperphotosensitivity, decubitis ulcer, Sydenham's chorea, sclerosis, adult-onset diabetes, insulin-dependent diabetes, juvenile diabetes, atherosclerosis, glomerulonephritis, IgA nephropathy, tubulointerstitial nephritis, primary biliary cirrhosis, primary sclerosing cholangitis, fulminant hepatitis, viral hepatitis, GVHD, contact dermatitis and septicemia, infections such as fungal, mycoplasma, viral and protozoan infections, cardiovascular diseases such as cardiac failure, cardiomegaly, arrhythmia, angina pectoris, cardiac ischemia, arterial embolism, aneurysm, varix and circulatory disorders, central nervous system diseases such as Alzheimer's disease, dementia, Parkinson's disease, stroke, cerebral infarction, cerebral ischemia, depression, manic depression, schizophrenia, Huntington's chorea, epilepsy, convulsion, hyperactivity disorder, encephalitis, meningitis, anorexia and bulimia, and various diseases such as lymphoma, leukemia, polyuria, thamuria and diabetic retinopathy (and particularly against rejection reactions during various organs transplants and skin transplants, and autoimmune diseases such as systemic lupus erythematosus, rheumatoid arthritis, multiple sclerosis and atopic dermatitis).

Thus, an object of the present invention is to provide a pharmaceutical composition containing a novel amino alcohol compound having low toxicity and superior immunosuppressive activity, a pharmacologically acceptable salt thereof or a pharmacologically acceptable ester thereof.

In addition, since it is desired to discover a pharmaceutical composition that is useful for diseases caused by abnormal peripheral blood lymphocyte count and so forth, a problem to be solved by the present invention is to provide a pharmaceutical composition that is useful for the aforementioned diseases, has low toxicity, and demonstrates superior physicochemical properties and superior pharmacokinetics.

Means for Solving the Problem

The present invention will be described specifically.
(1) The amino alcohol compound contained in the pharmaceutical composition of the present invention has the following general formula (I'):
[Chemical Formula 7]

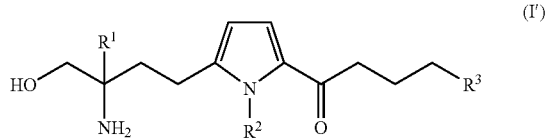

(wherein $R^1$ represents a methyl group or an ethyl group, $R^2$ represents a methyl group or an ethyl group, and $R^3$ represents a phenyl group substituted with 1 to 3 substituents selected from the group consisting of a halogen atom, a lower alkyl group, a cycloalkyl group, a lower alkoxy group, a halogeno lower alkyl group, a lower aliphatic acyl group and a cyano group).

The present invention provides a pharmaceutical composition containing a compound having general formula (I'), a pharmacologically acceptable salt thereof or a pharmacologically acceptable ester thereof.
(2) In (1), a compound wherein $R^1$ is a methyl group, or a pharmacologically acceptable salt thereof;
(3) in (1) or (2), a compound wherein $R^2$ is a methyl group, or a pharmacologically acceptable salt thereof;
(4) in (1) to (3), a compound wherein $R^3$ is a phenyl group substituted with 1 to 3 groups selected from the group consisting of a lower alkyl group, a cycloalkyl group and a lower alkoxy group, or a pharmacologically acceptable salt thereof;
(5) in (1) to (3), a compound wherein $R^3$ is a phenyl group substituted with 1 to 3 groups selected from the group consisting of a lower alkyl group and a lower alkoxy group, or a pharmacologically acceptable salt thereof;
(6) in any one selected from (1) to (3), a compound wherein $R^3$ is a phenyl group substituted with 1 to 3 groups selected from the group consisting of a methyl group and a methoxy group, or a pharmacologically acceptable salt thereof; and,
(7) in (1), any compound selected from the following compounds, or a pharmacologically acceptable salt thereof:

2-amino-2-methyl-4-{1-methyl-5-[4-(2-methylphenyl) butanoyl]pyrrol-2-yl}butan-1-ol,
2-amino-2-methyl-4-{1-methyl-5-[4-(3-methylphenyl) butanoyl]pyrrol-2-yl}butan-1-ol,
2-amino-2-methyl-4-{1-methyl-5-[4-(4-methylphenyl) butanoyl]pyrrol-2-yl}butan-1-ol,
2-amino-2-methyl-4-{1-methyl-5-[4-(2,3-dimethylphenyl)butanoyl]pyrrol-2-yl}butan-1-ol,
2-amino-2-methyl-4-{1-methyl-5-[4-(2,4-dimethylphenyl)butanoyl]pyrrol-2-yl}butan-1-ol,
2-amino-2-methyl-4-{1-methyl-5-[4-(2,5-dimethylphenyl)butanoyl]pyrrol-2-yl}butan-1-ol,
2-amino-2-methyl-4-{1-methyl-5-[4-(3,4-dimethylphenyl)butanoyl]pyrrol-2-yl}butan-1-ol,
2-amino-2-methyl-4-{1-methyl-5-[4-(3,5-dimethylphenyl)butanoyl]pyrrol-2-yl}butan-1-ol,
2-amino-2-methyl-4-{1-methyl-5-[4-(4-ethylphenyl)butanoyl]pyrrol-2-yl}butan-1-ol,
2-amino-2-methyl-4-{1-methyl-5-[4-(4-isopropylphenyl) butanoyl]pyrrol-2-yl}butan-1-ol,
2-amino-2-methyl-4-{1-methyl-5-[4-(4-cyclopropylphenyl)butanoyl]pyrrol-2-yl}butan-1-ol,
2-amino-2-methyl-4-{1-methyl-5-[4-(4-t-butylphenyl) butanoyl]pyrrol-2-yl}butan-1-ol,
2-amino-2-methyl-4-{1-methyl-5-[4-(4-methoxyphenyl) butanoyl]pyrrol-2-yl}butan-1-ol,
2-amino-2-methyl-4-{1-methyl-5-[4-(3,4-dimethoxyphenyl)butanoyl]pyrrol-2-yl}butan-1-ol,
2-amino-2-methyl-4-{1-methyl-5-[4-(3-methyl-4-methoxyphenyl)butanoyl]pyrrol-2-yl}butan-1-ol,
2-amino-2-methyl-4-{1-methyl-5-[4-(3-methoxy-4-methylphenyl)butanoyl]pyrrol-2-yl}butan-1-ol,
2-amino-2-methyl-4-{1-methyl-5-[4-(4-fluorophenyl)butanoyl]pyrrol-2-yl}butan-1-ol,
2-amino-2-methyl-4-{1-methyl-5-[4-(4-chlorophenyl)butanoyl]pyrrol-2-yl}butan-1-ol,
2-amino-2-methyl-4-{1-methyl-5-[4-(4-trifluoromethylphenyl)butanoyl]pyrrol-2-yl}butan-1-ol,
2-amino-2-methyl-4-{1-methyl-5-[4-(4-cyanophenyl)butanoyl]pyrrol-2-yl}butan-1-ol,
2-amino-2-ethyl-4-{1-methyl-5-[4-(2-methylphenyl)butanoyl]pyrrol-2-yl}butan-1-ol,
2-amino-2-ethyl-4-{1-methyl-5-[4-(3-methylphenyl)butanoyl]pyrrol-2-yl}butan-1-ol,
2-amino-2-ethyl-4-{1-methyl-5-[4-(4-methylphenyl)butanoyl]pyrrol-2-yl}butan-1-ol,
2-amino-2-ethyl-4-{1-methyl-5-[4-(2,3-dimethylphenyl) butanoyl]pyrrol-2-yl}butan-1-ol,
2-amino-2-ethyl-4-{1-methyl-5-[4-(2,4-dimethylphenyl) butanoyl]pyrrol-2-yl}butan-1-ol,
2-amino-2-ethyl-4-{1-methyl-5-[4-(2,5-dimethylphenyl) butanoyl] pyrrol-2-yl}butan-1-ol,
2-amino-2-ethyl-4-{1-methyl-5-[4-(3,4-dimethylphenyl) butanoyl]pyrrol-2-yl}butan-1-ol,
2-amino-2-ethyl-4-{1-methyl-5-[4-(3,5-dimethylphenyl) butanoyl]pyrrol-2-yl}butan-1-ol,
2-amino-2-ethyl-4-{1-methyl-5-[4-(4-ethylphenyl)butanoyl]pyrrol-2-yl}butan-1-ol,
2-amino-2-ethyl-4-{1-methyl-5-[4-(4-isopropylphenyl) butanoyl]pyrrol-2-yl}butan-1-ol,
2-amino-2-ethyl-4-{1-methyl-5-[4-(4-cyclopropylphenyl)butanoyl]pyrrol-2-yl}butan-1-ol,
2-amino-2-ethyl-4-{1-methyl-5-[4-(4-t-butylphenyl)butanoyl]pyrrol-2-yl}butan-1-ol,
2-amino-2-ethyl-4-{1-methyl-5-[4-(4-methoxyphenyl) butanoyl]pyrrol-2-yl}butan-1-ol, 2-amino-2-ethyl-4-{1-methyl-5-[4-(3,4-dimethoxyphenyl)butanoyl]pyrrol-2-yl}butan-1-ol,
2-amino-2-ethyl-4-{1-methyl-5-[4-(3-methyl-4-methoxyphenyl)butanoyl]pyrrol-2-yl}butan-1-ol,
2-amino-2-ethyl-4-{1-methyl-5-[4-(4-fluorophenyl)butanoyl]pyrrol-2-yl}butan-1-ol,
2-amino-2-ethyl-4-{1-methyl-5-[4-(4-chlorophenyl)butanoyl]pyrrol-2-yl}butan-1-ol,
2-amino-2-ethyl-4-{1-methyl-5-[4-(4-trifluoromethylphenyl)butanoyl]pyrrol-2-yl}butan-1-ol and
2-amino-2-ethyl-4-{1-methyl-5-[4-(4-cyanophenyl)butanoyl]pyrrol-2-yl}butan-1-ol.

In addition, the present invention includes the following inventions.

(8) A pharmaceutical composition containing a compound having the following general formula (I):
[Chemical Formula 8]

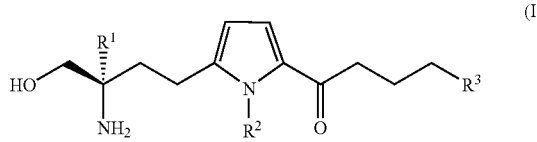

(I)

(wherein $R^1$ represents a methyl group or an ethyl group, $R^2$ represents a methyl group or an ethyl group, and $R^3$ represents a phenyl group substituted with 1 to 3 substituents selected from a halogen atom, lower alkyl group, a cycloalkyl group, a lower alkoxy group, a halogeno lower alkyl group, a lower aliphatic acyl group and a cyano group), a pharmacologically acceptable salt thereof or a pharmacologically acceptable ester thereof;

(9) a pharmaceutical composition-according to (8) wherein $R^1$ is a methyl group;
(10) a pharmaceutical composition according to (8) or (9) wherein $R^2$ is a methyl group;
(11) a pharmaceutical composition according to any of (8) to (10) wherein $R^3$ is a phenyl group substituted with 1 to 3 substituents selected from the group consisting of a lower alkyl group, a cycloalkyl group and a lower alkoxy group;
(12) a pharmaceutical composition according to any of (8) to (10) wherein $R^3$ is a phenyl group substituted with 1 to 3 substituents selected from the group consisting of a lower alkyl group and a lower alkoxy group;
(13) a pharmaceutical composition according to any of (8) to (10) wherein $R^3$ is a phenyl group substituted with 1 to 3 substituents selected from the group consisting of a methyl group and a methoxy group;
(14) a pharmaceutical composition containing any compound selected from the following compounds, or a pharmacologically acceptable salt thereof:
(2R)-2-amino-2-methyl-4-{1-methyl-5-[4-(3-methylphenyl) butanoyl]pyrrol-2-yl}butan-1-ol,
(2R)-2-amino-2-methyl-4-{1-methyl-5-[4-(4-methylphenyl) butanoyl]pyrrol-2-yl}butan-1-ol,
(2R)-2-amino-2-methyl-4-{1-methyl-5-[4-(3,4-dimethylphenyl)butanoyl]pyrrol-2-yl}butan-1-ol,
(2R)-2-amino-2-methyl-4-{1-methyl-5-[4-(4-methoxyphenyl)butanoyl]pyrrol-2-yl}butan-1-ol and
(2R)-2-amino-2-methyl-4-{1-methyl-5-[4-(3-methyl-4-methoxyphenyl)butanoyl]pyrrol-2-yl}butan-1-ol;
(15) a pharmaceutical composition according to any of (8) to (14) wherein the pharmacologically acceptable salt is a fumarate;
(16) a pharmaceutical composition according to any of (8) to (15) that has peripheral blood lymphocyte count lowering activity;
(17) a pharmaceutical composition according to any of (8) to (15) that is a peripheral blood lymphocyte count lowering agent;
(18) a pharmaceutical composition according to any of (8) to (15) that inhibits increases in peripheral blood lymphocyte count;
(19) a pharmaceutical composition according to any of (8) to (15) for treatment or prophylaxis of diseases caused by abnormal peripheral blood lymphocyte count;
(20) a pharmaceutical composition according to any of (8) to (15) for prophylaxis or treatment of diseases for which symptoms can be improved by lowering peripheral blood lymphocyte count;
(21) a pharmaceutical composition according to any of (8) to (15) that exhibits immunosuppressive effects through peripheral blood lymphocyte count lowering activity;
(22) a pharmaceutical composition according to any of (8) to (15) for suppressing rejection reactions during skin transplants or organ transplants;
(23) a pharmaceutical composition according to any of (8) to (15) for prophylaxis or treatment of autoimmune diseases;
(24) a pharmaceutical composition according to (23) wherein the autoimmune diseases are one or more types selected from the group consisting of rheumatoid arthritis, psoriasis, atopic dermatitis, multiple sclerosis, ulcerative colitis and Crohn's disease;
(25) a pharmaceutical composition according to any of (8) to (24) for administering orally at a dose of the active ingredient of 0.00042 mg/kg/day to 0.84 mg/kg/day;
(26) a pharmaceutical composition according to any of (8) to (25) wherein the number of administrations is once per one to three days; and,
(27) a pharmaceutical composition according to any of (8) to (25) wherein the number of administrations is once per day.

Effect of the Invention

A pharmaceutical composition containing an amino alcohol compound having general formula (I) or (I') of the present invention or a pharmacologically acceptable salt thereof has low toxicity and superior immunosuppressive activity, and is particularly useful as a prophylactic or therapeutic (and preferably a therapeutic) in warm-blooded animals (and particularly humans) against rejection reactions during various organ transplants or skin transplants, autoimmune diseases or other immunity-related diseases such as systemic lupus erythematosus, rheumatoid arthritis, polymyositis, fibrositis, skeletal myositis, arthrosteitis, osteoarthritis, dermatomyositis, scleroderma, Behcet's disease, Crohn's disease, ulcerative colitis, autoimmune hepatitis, aplastic anemia, idiopathic thrombocytopenic purpura, autoimmune hemolytic anemia, multiple sclerosis, autoimmune pomphus, psoriasis vulgaris, angiitis, Wegener's granuloma, uveitis, Sjogren's syndrome, idiopathic interstitial pneumonia, Goodpasture's syndrome, sarcoidosis, allergic granulomatous angiitis, bronchial asthma, myocarditis, cardiomyopathy, aortitis syndrome, postmyocardial infarction syndrome, primary pulmonary hypertension, lipoid nephrosis, membranous nephropathy, membranoproliferative glomerulonephritis, focal glomerular sclerosis, crescenteric nephritis, myasthenia gravis, inflammatory neuropathy, atopic dermatitis, chronic photosensitive dermatitis, hyperphotosensitivity, decubitis ulcer, Sydenham's chorea, sclerosis, adult-onset diabetes, insulin-dependent diabetes, juvenile diabetes, atherosclerosis, glomerulonephritis, IgA nephropathy, tubulointerstitial nephritis, primary biliary cirrhosis, primary sclerosing cholangitis, fulminant hepatitis, viral hepatitis, GVHD, contact dermatitis and septicemia, infections such as fungal, mycoplasma, viral and protozoan infections, cardiovascular diseases such as cardiac failure, cardiomegaly, arrhythmia, angina pectoris, cardiac ischemia, arterial embolism, aneurysm, varix and circulatory disorders, central nervous system diseases such as Alzheimer's disease, dementia, Parkinson's disease, stroke, cerebral infarction, cerebral ischemia, depression, manic depression, schizophrenia, Huntington's chorea, epilepsy, convulsion, hyperactivity disorder, encephalitis, meningitis, anorexia and bulimia, and various diseases such as lymphoma, leukemia, polyuria, thamuria and diabetic retinopathy (and particularly against rejection reactions during various organs transplants or skin transplants, and autoimmune diseases such as systemic lupus erythematosus, rheumatoid arthritis, multiple sclerosis and atopic dermatitis).

In addition, since the pharmaceutical composition of the present invention has low toxicity, demonstrates superior physical properties and superior pharmacokinetics, and demonstrates satisfactory peripheral blood lymphocyte count lowering activity through oral administration, it is useful as an oral prophylactic or oral therapeutic (and preferably an oral therapeutic) for the aforementioned autoimmune diseases and so forth, or as an oral prophylactic or oral therapeutic (and preferably an oral therapeutic) for other diseases caused by abnormal peripheral blood lymphocyte count.

BEST MODE FOR CARRYING OUT THE INVENTION

The following provides a specific explanation of the present invention.

The amino alcohol compound serving as the active ingredient of the pharmaceutical composition of the present invention has the following general formula (I) or (I').

[Chemical Formula 9]

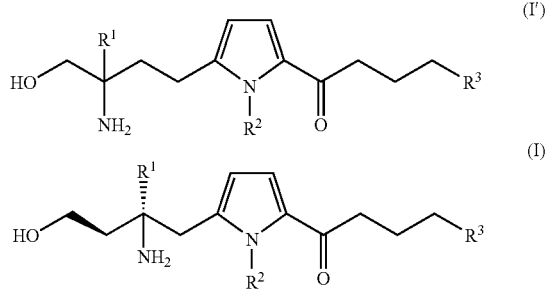

In the above formulae, a "halogen atom" in the definition of $R^3$ is a fluorine atom, chlorine atom, bromine atom or iodine atom, preferably a fluorine atom or chlorine atom, and most preferably a chlorine atom.

In the above formulae, a "lower alkyl group" in the definition of $R^3$ is a linear or branched alkyl group having 1 to 6 carbon atoms such as a methyl, ethyl, propyl, isopropyl, butyl, isobutyl, s-butyl, t-butyl, pentyl, isopentyl, 2-methylbutyl, neopentyl, 1-ethylpropyl, hexyl, isohexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 1-ethylbutyl or 2-ethylbutyl group, preferably an alkyl group having 1 to 4 carbon atoms, more preferably a methyl or ethyl group, and most preferably a methyl group.

In the above formulae, a "cycloalkyl group" in the definition of $R^3$ is a cyclic alkyl group having 3 to 6 carbon atoms such as a cyclopropyl, cyclobutyl, cyclopentyl or cyclohexyl group, preferably a cyclopropyl or cyclobutyl group, and most preferably a cyclopropyl group.

In the above formulae, a "lower alkoxy group" in the definition of $R^3$ indicates a group in which the aforementioned "lower alkyl group" is bonded to an oxygen atom, and is a linear or branched alkoxy group having 1 to 6 carbon atoms such as a methoxy, ethoxy, propoxy, isopropoxy, butoxy, isobutoxy, s-butoxy, t-butoxy, pentoxy, isopentoxy, 2-methylbutoxy, 1-ethylpropoxy, 2-ethylpropoxy, neopentoxy, hexyloxy, 4-methylpentoxy, 3-methylpentoxy, 2-methylpentoxy, 3,3-dimethylbutoxy, 2,2-dimethylbutoxy, 1,1-dimethylbutoxy, 1,2-dimethylbutoxy, 1,3-dimethylbutoxy or 2,3-dimethylbutoxy group, preferably an alkoxy group having 1 to 4 carbon atoms, more preferably an alkoxy group having 1 or 2 carbon atoms, and most preferably a methoxy group.

In the above formulae, a "halogeno lower alkyl group" in the definition of $R^3$ indicates a group in which a halogen atom is substituted in the aforementioned "lower alkyl group", and is an alkyl group having 1 to 6 carbon atoms in which a halogen atom has been substituted such as a trifluoromethyl, trichloromethyl, difluoromethyl, dichloromethyl, dibromomethyl, fluoromethyl, 2,2,2-trifluoroethyl, 2,2,2-trichloroethyl, 2-bromoethyl, 2-chloroethyl, 2-fluoroethyl, 2-iodoethyl, 3-chloropropyl, 4-fluorobutyl, 6-iodohexyl or 2,2-dibromoethyl group, preferably an alkyl group having 1 to 4 carbon atoms in which a halogen atom has been substituted, more preferably an alkyl group having 1 or 2 carbon atoms in which a halogen atom has been substituted, and most preferably a trifluoromethyl group.

In the above formulae, a "lower aliphatic acyl group" in the definition of $R^3$ is a linear or branched aliphatic acyl group having 1 to 6 carbon atoms such as a formyl, acetyl, propionyl, butyryl, isobutyryl, pivaloyl or hexanoyl group, preferably an aliphatic acyl group having 1 to 4 carbon atoms, more preferably an acetyl or propionyl group, and most preferably an acetyl group.

The aforementioned "pharmacologically acceptable salt thereof" refers to a salt of a compound having general formula (I) or (I') of the present invention since said compound has a basic group in the manner of an amino group and can be converted to a salt by reacting with acid.

Preferable examples of pharmacologically acceptable salts of a compound having general formula (I) or (I') of the present invention normally include salts of halogenated hydroacids such as hydrofluorides, hydrochlorides, hydrobromides and hydroiodides, salts of inorganic acids such as nitrates, perchlorates, sulfates and phosphates; salts of lower alkane sulfonic acids such as methane sulfonates, trifluoromethane sulfonates and ethane sulfonates, salts of aryl sulfonic acids such as benzene sulfonates and p-toluene sulfonates, salts of organic acids such as acetates, malates, fumarates, succinates, citrates, ascorbates, tartrates, oxalates and maleates; and salts of amino acids such as glycine, lysine, arginine, ornithine, glutamates and aspartates, and more preferably salts of halogenated hydroacids.

In the present invention, a preferable salt is determined in consideration of the physical properties, solubility, hygroscopicity, thermal stability and melting point and so forth of the salt itself, and the stability when mixing with a vehicle or diluent and so forth during formulation and so forth (including not reacting with that mixture along with the physical properties, solubility, hygroscopicity, thermal stability and melting point and so forth of the preparation). A pharmacologically acceptable salt of a compound having general formula (I) or (I') serving as the active ingredient of the present invention is preferably a salt of an organic acid and more preferably a fumarate.

The aforementioned "ester" refers to an ester of a compound having general formula (I) or (I') of the present invention since said compound can be converted to an ester, an example of such an ester being an "ester of a hydroxyl group", and such esters refer to esters in which each ester residue is an "ordinary protecting group" or a "protecting group that can be cleaved by a biological method such as hydrolysis in the body".

An "ordinary protecting group" refers to protecting groups that can be cleaved by a chemical method such as hydrogenolysis, hydrolysis, electrolysis or photolysis.

Preferable examples of an "ordinary protecting group" in an "ester of a hydroxyl group" include "aliphatic acyl groups" including alkanoyl groups such as a formyl, acetyl, propionyl, butyryl, isobutyryl, pentanoyl, pivaloyl, valeryl, isovaleryl, octanoyl, nonanoyl, decanoyl, 3-methylnonanoyl, 8-methylnonanoyl, 3-ethyloctanoyl, 3,7-dimethyloctanoyl, undecanoyl, dodecanoyl, tridecanoyl, tetradecanoyl, pentadecanoyl, hexadecanoyl, 1-methylpentadecanoyl, 14-methylpentadecanoyl, 13,13-dimethyltetradecanoyl, heptadecanoyl, 15-methylhexadecanoyl, octadecanoyl, 1-methylheptadecanoyl, nonadecanoyl, eicosanoyl or heneicosanoyl group, halogenated alkyl carbonyl groups such as a chloroacetyl, dichloroacetyl, trichloroacetyl or trifluoroacetyl group, lower alkoxy alkyl carbonyl groups such as a methoxyacetyl group, and unsaturated alkyl carbonyl groups such as an acryloyl, propionoyl, methacryloyl, crotonoyl, isocrotonoyl or (E)-2-methyl-2-butenoyl group (and preferably aliphatic acyl groups having 1 to 6 carbon atoms); "aromatic acyl groups" including aryl carbonyl groups such as a benzoyl, α-naphthoyl or β-naphthoyl group, halogenated aryl carbonyl groups such as a 2-bromobenzoyl, 4-chlorobenzoyl or 2,4,6-trifluorobenzoyl group, lower alkylated aryl carbonyl groups such as a 2,4,6-trimethylbenzoyl or 4-tolyl group, lower alkoxylated aryl carbonyl groups such as a 4-anisoyl group, nitrated aryl carbonyl groups such as a 4-nitrobenzoyl or 2-nitrobenzoyl group, lower alkoxycarbonylated aryl carbonyl groups such as a 2-(methoxycarbonyl)benzoyl group, and arylated aryl carbonyl groups such as a 4-phenylbenzoyl group; "alkoxycarbonyl groups" including lower alkoxycarbonyl groups such as a methoxycarbonyl, ethoxycarbonyl, propoxycarbonyl, butoxycarbonyl, s-butoxycarbonyl, t-butoxycarbonyl or isobutoxycarbonyl group, and lower alkoxycarbonyl groups substituted with a halogen atom or tri-lower alkylsilyl group such as a 2,2,2-trichloroethoxycarbonyl or 2-trimethylsilyl ethoxycarbonyl group; "tetrahydropyranyl or tetrahydrothiopyranyl groups" such as a tetrahydropyran-2-yl, 3-bromotetrahydropyran-2-yl or 4-methoxytetrahydrothiopyran-4-yl group; "tetrahydrofuranyl or tetrahydrothiofuranyl" groups such as a tetrahydrofuran-2-yl or tetrahydrothiofuran-2-yl group; "silyl groups" including tri-lower alkyl silyl groups such as a trimethylsilyl, triethylsilyl, isopropyl dimethylsilyl, t-butyl dimethylsilyl, methyl diisopropylsilyl, methyl di-t-butylsilyl or triisopropylsilyl group, and tri-lower alkyl silyl groups substituted with 1 to 2 aryl groups such as a diphenyl methylsilyl, diphenyl butylsilyl, diphenyl isopropylsilyl or phenyl diisopropylsilyl group; "alkoxymethyl groups" including lower alkoxymethyl groups such as a methoxymethyl, 1,1-dimethyl-1-methoxymethyl, ethoxymethyl, propoxymethyl, isopropoxymethyl, butoxymethyl or t-butoxymethyl group, lower alkoxylated lower alkoxymethyl groups such as a 2-methoxyethoxymethyl group, and halogeno lower alkoxymethyl groups such as a 2,2,2-trichloroethoxymethyl or bis(2-chloroethoxy)methyl group; "substituted ethyl groups" including lower alkoxylated ethyl groups such as a 1-ethoxyethyl or 1-(isopropoxy)ethyl group, and halogenated ethyl groups such as a 2,2,2-trichloroethyl group; "aralkyl groups" including lower alkyl groups substituted with 1 to 3 aryl groups such as a benzyl, α-naphtylmethyl, β-naphthylmethyl, diphenylmethyl, triphenylmethyl, α-naphthyldiphenylmethyl or 9-anthrylmethyl group, and lower alkyl groups substituted with 1 to 3 aryl groups in which the aryl ring is substituted with a lower alkyl, lower alkoxy, nitro, halogen or cyano group such as a 4-methylbenzyl, 2,4,6-trimethylbenzyl, 3,4,5-trimethylbenzyl, 4-methoxybenzyl, 4-methoxyphenyldiphenylmethyl, 2-nitrobenzyl, 4-nitrobenzyl, 4-chlorobenzyl, 4-bromobenzyl or 4-cyanobenzyl group; "alkenyloxycarbonyl groups" such as a vinyloxycarbonyl or allyloxycarbonyl group; and, "aralkyloxycarbonyl groups" in which the aryl ring is optionally substituted with 1 to 2 lower alkoxy groups or nitro groups such as a benzyloxycarbonyl, 4-methoxybenzyloxycarbonyl, 3,4-dimethoxybenzyloxycarbonyl, 2-nitrobenzyloxycarbonyl or 4-nitrobenzyloxycarbonyl group.

A "protecting group that can be cleaved by a biological method such as hydrolysis in the body" refers to a protecting group that generates a free acid or salt thereof as a result of being cleaved by a biological method such as hydrolysis in the body, and whether or not it is a derivative thereof can be determined by administering to a laboratory animal such as a rat or mouse by intravenous injection, subsequently investigating a body fluid of the animal, and detecting the original compound or pharmacologically acceptable salt thereof.

Preferable examples of a "protecting group that can be cleaved by a biological method such as hydrolysis in the body" in an "ester of a hydroxyl group" include a 1-(acyloxy) "lower alkyl group" such as a 1-("lower aliphatic acyl" oxy) "lower alkyl group", e.g. a formyloxymethyl, acetoxymethyl, dimethylaminoacetoxymethyl, propionyloxymethyl, butyryloxymethyl, pivaloyloxymethyl, valeryloxymethyl, isovaleryloxymethyl, hexanoyloxymethyl, 1-formyloxyethyl, 1-acetoxyethyl, 1-propionyloxyethyl, 1-butyryloxyethyl, 1-pivaloyloxyethyl, 1-valeryloxyethyl, 1-isovaleryloxyethyl, 1-hexanoyloxyethyl, 1-formyloxypropyl, 1-acetoxypropyl, 1-propionyloxypropyl, 1-butyryloxypropyl, 1-pivaloyloxypropyl, 1-valeryloxypropyl, 1-isovaleryloxypropyl, 1-hexanoyloxypropyl, 1-acetoxybutyl, 1-propionyloxybutyl, 1-butyryloxybutyl, 1-pivaloyloxybutyl, 1-acetoxypentyl, 1-propionyloxypentyl, 1-butyryloxypentyl, 1-pivaloyloxypentyl or 1-pivaloyloxyhexyl group, a 1-("cycloalkyl" carbonyloxy) "lower alkyl group", e.g. a cyclopentylcarbonyloxymethyl, cyclohexylcarbonyloxymethyl, 1-cyclopentylcarbonyloxyethyl, 1-cyclohexylcarbonyloxyethyl, 1-cyclopentylcarbonyloxypropyl, 1-cyclohexylcarbonyloxypropyl, 1-cyclopentylcarbonyloxybutyl or 1-cyclohexylcarbonyloxybutyl group, a 1-("aromatic acyl"oxy) "lower alkyl group" e.g. a benzoyloxymethyl group; a "carbonyloxy alkyl group" such as a (lower alkoxycarbonyloxy) alkyl group, e.g. a methoxycarbonyloxymethyl, ethoxycarbonyloxymethyl, propoxycarbonyloxymethyl, isopropoxycarbonyloxymethyl, butoxycarbonyloxymethyl, isobutoxycarbonyloxymethyl, pentyloxycarbonyloxymethyl, hexyloxycarbonyloxymethyl, cyclohexyloxycarbonyloxymethyl, cyclohexyloxycarbonyloxy, (cyclohexyl)methyl, 1-(methoxycarbonyloxy)ethyl, 1-(ethoxycarbonyloxy) ethyl, 1-(propoxycarbonyloxy)ethyl, 1-(isopropoxycarbonyloxy)ethyl, 1-(butoxycarbonyloxy) ethyl, 1-(isobutoxycarbonyloxy)ethyl, 1-(t-butoxycarbonyloxy)ethyl, 1-(pentyloxycarbonyloxy)ethyl, 1-(hexyloxycarbonyloxy)ethyl, 1-(cyclopentyloxycarbonyloxy)ethyl, 1-(cyclopentyloxycarbonyloxy)propyl, 1-(cyclohexyloxycarbonyloxy)propyl, 1-(cyclopentyloxycarbonyloxy)butyl, 1-(cyclohexyloxycarbonyloxy)butyl, 1-(cyclohexyloxycarbonyloxy)ethyl, 1-(ethoxycarbonyloxy)propyl, 1-(methoxycarbonyloxy)propyl, 1-(ethoxycarbonyloxy)propyl, 1-(propoxycarbonyloxy)propyl, 1-(isopropoxycarbonyloxy)propyl, 1-(butoxycarbonyloxy)propyl, 1-(isobutoxycarbonyloxy)propyl, 1-(pentyloxycarbonyloxy)propyl, 1-(hexyloxycarbonyloxy)propyl, 1-(methoxycarbonyloxy)butyl, 1-(ethoxycarbonyloxy)butyl, 1-(propoxycarbonyloxy)butyl, 1-(isopropoxycarbonyloxy)butyl, 1-(butoxycarbonyloxy)butyl, 1-(isobutoxycarbonyloxy)butyl, 1-(methoxycarbonyloxy)pentyl, 1-(ethoxycarbonyloxy)pentyl, 1-(methoxycarbonyloxy)hexyl, or 1-(ethoxycarbonyloxy)hexyl group; an oxodioxblenyl methyl group, e.g. a (5-phenyl-2-oxo-1,3-dioxolen-4-yl)methyl, [5-(4-methylphenyl)-2-oxo-1,3-dioxolen-4-yl]methyl, [5-(4-methoxyphenyl)-2-oxo-1,3-dioxolen-4-yl]methyl, [5-(4-fluiorophenyl)-2-oxo-1,3-dioxolen-4-yl]methyl, [5-(4-chlorophenyl)-2-oxo-1,3-dioxolen-4-yl]methyl, (2-oxo-1,3-dioxolen-4-yl)methyl, (5-methyl-2-oxo-1,3-dioxolen-4-yl)methyl, (5-ethyl-2-oxo-1,3-dioxolen-4-yl)methyl, (5-propyl-2-oxo-1,3-dioxolen-4-yl)methyl, (5-isopropyl-2-oxo-1,3-dioxolen-4-yl)methyl, or (5-butyl-2-oxo-1,3-dioxolen-4-yl)methyl group: a "phthalidyl group" such as a phthalidyl, dimethylphthalidyl, or dimethoxy phthalidyl group: the above-mentioned "lower aliphatic acyl group": the above-mentioned "aromatic acyl group": a "half ester salt residue of succinic acid": a "phosphate ester salt residue": an "ester formation residue such as amino acid": a carbamoyl group: a carbamoyl group substituted with 1 or 2 lower alkyl groups: and a pivaloyloxymethyloxycarbonyl group, and preferably a "carbonyloxyalkyl group".

A compound having general formula (I) or (I') serving as an active ingredient of the present invention, a pharmacologically acceptable salt thereof or a pharmacologically acceptable ester thereof may be in the form of a hydrate by allowing to stand in air, recrystallizing, absorbing water or having adsorbed water, and such hydrates are also included in the present invention.

A compound having general formula (I) or (I') serving as an active ingredient of the present invention, a pharmacologically acceptable salt thereof, a pharmacologically acceptable ester thereof, or a pharmacologically acceptable other derivative thereof has optical isomers since it has an asymmetric carbon atom within its molecule.

A compound having general formula (I) serving as an active ingredient of the present invention is an optical isomer, namely the (R) isomer. Although the present invention mainly includes the (R) isomer among the optical isomers thereof, it also includes the (R) isomer in mixture with a small amount of the (S) isomer for reasons attributable to the production process and so forth, as represented by the formula (I').

Although specific examples of a compound having general formula (I) or (I') serving as an active ingredient of the present invention include, for example, the compounds described in the following Table 1, the present invention is not limited to these compounds.

The following abbreviations are used in the table.

| | |
|---|---|
| Ac | acetyl group |
| tBu | t-butyl group |
| Et | ethyl group |
| EtO | ethoxy formula |
| Me | methyl group |
| MeO | methoxy group |
| Ph | phenyl group |
| cPr | cyclopropyl group |
| iPr | isopropyl group |

TABLE 1

[Chemical Formula 101]

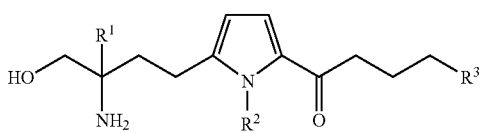

(I')

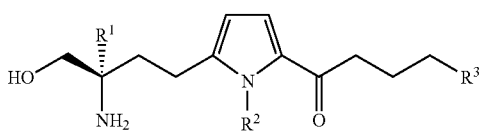

(I)

| Compound No. | $R^1$ | $R^2$ | $R^3$ |
|---|---|---|---|
| 1 | Me | Me | 2-F—Ph |
| 2 | Me | Me | 3-F—Ph |
| 3 | Me | Me | 4-F—Ph |
| 4 | Me | Me | 2,3-di-F—Ph |
| 5 | Me | Me | 2,4-di-F—Ph |
| 6 | Me | Me | 2,5-di-F—Ph |
| 7 | Me | Me | 3,4-di-F—Ph |
| 8 | Me | Me | 3,5-di-F—Ph |
| 9 | Me | Me | 2-Cl—Ph |
| 10 | Me | Me | 3-Cl—Ph |
| 11 | Me | Me | 4-Cl—Ph |
| 12 | Me | Me | 2,3-di-Cl—Ph |
| 13 | Me | Me | 2,4-di-Cl—Ph |
| 14 | Me | Me | 2,5-di-Cl—Ph |
| 15 | Me | Me | 3,4-di-Cl—Ph |
| 16 | Me | Me | 3,5-di-Cl—Ph |
| 17 | Me | Me | 2-Me—Ph |
| 18 | Me | Me | 3-Me—Ph |
| 19 | Me | Me | 4-Me—Ph |
| 20 | Me | Me | 2,3-di-Me—Ph |
| 21 | Me | Me | 2,4-di-Me—Ph |
| 22 | Me | Me | 2,5-di-Me—Ph |
| 23 | Me | Me | 3,4-di-Me—Ph |
| 24 | Me | Me | 3,S-di-Me—Ph |
| 25 | Me | Me | 2-Et—Ph |
| 26 | Me | Me | 3-Et—Ph |
| 27 | Me | Me | 4-Et—Ph |
| 28 | Me | Me | 2-cPr—Ph |
| 29 | Me | Me | 3-cPr—Ph |
| 30 | Me | Me | 4-cPr—Ph |
| 31 | Me | Me | 2-iPr—Ph |
| 32 | Me | Me | 3-iPr—Ph |
| 33 | Me | Me | 4-iPr—Ph |
| 34 | Me | Me | 2-tBu—Ph |
| 35 | Me | Me | 3-tBu—Ph |
| 36 | Me | Me | 4-tBu—Ph |
| 37 | Me | Me | 2-tBu—Ph |
| 38 | Me | Me | 3-tBu—Ph |
| 39 | Me | Me | 4-tBu—Ph |
| 40 | Me | Me | 2-MeO—Ph |
| 41 | Me | Me | 3-MeO—Ph |
| 42 | Me | Me | 4-MeO—Ph |
| 43 | Me | Me | 2,3-di-MeO—Ph |
| 44 | Me | Me | 2,4-ai-MeO—Ph |
| 45 | Me | Me | 2,5-ai-MeO—Ph |
| 46 | Me | Me | 3,4-di-MeO—Ph |
| 47 | Me | Me | 3,5-di-MeO—Ph |
| 48 | Me | Me | 2-EtO—Ph |

TABLE 1-continued

[Chemical Formula 101]

(I')  HO-C(R¹)(NH₂)-CH₂-CH₂-[pyrrole(N-R²)]-C(=O)-CH₂-CH₂-CH₂-R³

(I) same with stereochemistry at the carbon bearing R¹

| Compound No. | R¹ | R² | R³ |
|---|---|---|---|
| 49 | Me | Me | 3-EtO—Ph |
| 50 | Me | Me | 4-EtO—Ph |
| 51 | Me | Me | 2-iPrO—Ph |
| 52 | Me | Me | 3-iPrO—Ph |
| 53 | Me | Me | 4-iPrO—Ph |
| 54 | Me | Me | 2-Me-3-MeO—Ph |
| 55 | Me | Me | 2-Me-4-MeO—Ph |
| 56 | Me | Me | 2-Me-5-MeO—Ph |
| 57 | Me | Me | 3-Me-4-MeO—Ph |
| 58 | Me | Me | 3-Me-5-MeO—Ph |
| 59 | Me | Me | 2-MeO-3-Me—Ph |
| 60 | Me | Me | 2-MeO-4-Me—Ph |
| 61 | Me | Me | 2-MeO-5-Me—Ph |
| 62 | Me | Me | 3-MeO-4-Me—Ph |
| 63 | Me | Me | 3-MeO-5-Me—Ph |
| 64 | Me | Me | 2-CF₃—Ph |
| 65 | Me | Me | 3-CF₃—Ph |
| 66 | Me | Me | 4-CF₃—Ph |
| 67 | Me | Me | 3,5-di-CF₃—Ph |
| 68 | Me | Me | 2-Ac—Ph |
| 69 | Me | Me | 3-Ac—Ph |
| 70 | Me | Me | 4-Ac—Ph |
| 71 | Me | Me | 2-CN—Ph |
| 72 | Me | Me | 3-CN—Ph |
| 73 | Me | Me | 4-CN—Ph |
| 74 | Me | Et | 2-F—Ph |
| 75 | Me | Et | 3-F—Ph |
| 76 | Me | Et | 4-F—Ph |
| 77 | Me | Et | 2,3-di-F—Ph |
| 78 | Me | Et | 2,4-di-F—Ph |
| 79 | Me | Et | 2,5-di-F—Ph |
| 80 | Me | Et | 3,4-di-F—Ph |
| 81 | Me | Et | 3,5-di-F—Ph |
| 82 | Me | Et | 2-Cl—Ph |
| 83 | Me | Et | 3-Cl—Ph |
| 84 | Me | Et | 4-Cl—Ph |
| 85 | Me | Et | 2,3-di-Cl—Ph |
| 86 | Me | Et | 2,4-di-Cl—Ph |
| 87 | Me | Et | 2,5-di-Cl—Ph |
| 88 | Me | Et | 3,4-di-Cl—Ph |
| 89 | Me | Et | 3,5-di-Cl—Ph |
| 90 | Me | Et | 2-Me—Ph |
| 91 | Me | Et | 3-Me—Ph |
| 92 | Me | Et | 4-Me—Ph |
| 93 | Me | Et | 2,3-di-Me—Ph |
| 94 | Me | Et | 2,4-di-Me—Ph |
| 95 | Me | Et | 2,5-di-Me—Ph |
| 96 | Me | Et | 3,4-di-Me—Ph |
| 97 | Me | Et | 3,5-di-Me—Ph |
| 98 | Me | Et | 2-Et—Ph |
| 99 | Me | Et | 3-Et—Ph |
| 100 | Me | Et | 4-Et—Ph |
| 101 | Me | Et | 2-cPr—Ph |
| 102 | Me | Et | 3-cPr—Ph |
| 103 | Me | Et | 4-cPr—Ph |
| 104 | Me | Et | 2-iPr—Ph |
| 105 | Me | Et | 3-iPr—Ph |
| 106 | Me | Et | 4-iPr—Ph |
| 107 | Me | Et | 2-tBu—Ph |
| 108 | Me | Et | 3-tBu—Ph |
| 109 | Me | Et | 4-tBu—Ph |
| 110 | Me | Et | 2-tBu—Ph |
| 111 | Me | Et | 3-tBu—Ph |
| 112 | Me | Et | 4-tBu—Ph |
| 113 | Me | Et | 2-MeO—Ph |
| 114 | Me | Et | 3-MeO—Ph |
| 115 | Me | Et | 4-MeO—Ph |
| 116 | Me | Et | 2,3-di-MeO—Ph |
| 117 | Me | Et | 2,4-di-MeO—Ph |
| 118 | Me | Et | 2,5-di-MeO—Ph |
| 119 | Me | Et | 3,4-di-MeO—Ph |
| 120 | Me | Et | 3,5-di-MeO—Ph |
| 121 | Me | Et | 2-EtO—Ph |
| 122 | Me | Et | 3-EtO—Ph |
| 123 | Me | Et | 4-EtO—Ph |
| 124 | Me | Et | 2-iPrO—Ph |
| 125 | Me | Et | 3-iPrO—Ph |
| 126 | Me | Et | 4-iPrO—Ph |
| 127 | Me | Et | 2-Me-3-MeO—Ph |
| 128 | Me | Et | 2-Me-4-MeO—Ph |
| 129 | Me | Et | 2-Me-5-MeO—Ph |
| 130 | Me | Et | 3-Me-4-MeO—Ph |
| 131 | Me | Et | 3-Me-5-MeO—Ph |
| 132 | Me | Et | 2-MeO-3-Me—Ph |
| 133 | Me | Et | 2-MeO-4-Me—Ph |
| 134 | Me | Et | 2-MeO-5-Me—Ph |
| 135 | Me | Et | 3-MeO-4-Me—Ph |
| 136 | Me | Et | 3-MeO-5-Me—Ph |
| 137 | Me | Et | 2-CF₃—Ph |
| 138 | Me | Et | 3-CF₃—Ph |
| 139 | Me | Et | 4-CF₃—Ph |
| 140 | Me | Et | 3,5-di-CF₃—Ph |
| 141 | Me | Et | 2-Ac—Ph |
| 142 | Me | Et | 3-Ac—Ph |
| 143 | Me | Et | 4-Ac—Ph |
| 144 | Me | Et | 2-CN—Ph |
| 145 | Me | Et | 3-CN—Ph |
| 146 | Me | Et | 4-CN—Ph |
| 147 | Et | Me | 2-F—Ph |
| 148 | Et | Me | 3-F—Ph |
| 149 | Et | Me | 4-F—Ph |
| 150 | Et | Me | 2,3-di-F—Ph |
| 151 | Et | Me | 2,4-di-F—Ph |
| 152 | Et | Me | 2,5-di-F—Ph |
| 153 | Et | Me | 3,4-di-F—Ph |
| 154 | Et | Me | 3,5-di-F—Ph |
| 155 | Et | Me | 2-Cl—Ph |
| 156 | Et | Me | 3-Cl—Ph |
| 157 | Et | Me | 4-Cl—Ph |
| 158 | Et | Me | 2,3-di-Cl—Ph |
| 159 | Et | Me | 2,4-di-Cl—Ph |
| 160 | Et | Me | 2,5-di-Cl—Ph |
| 161 | Et | Me | 3,4-di-Cl—Ph |
| 162 | Et | Me | 3,5-di-Cl—Ph |
| 163 | Et | Me | 2-Me—Ph |
| 164 | Et | Me | 3-Me—Ph |
| 165 | Et | Me | 4-Me—Ph |
| 166 | Et | Me | 2,3-di-Me—Ph |
| 167 | Et | Me | 2,4-di-Me—Ph |
| 168 | Et | Me | 2,5-di-Me—Ph |

TABLE 1-continued

[Chemical Formula 101]

Structure (I'):
HO-CH2-C(R1)(NH2)-CH2-CH2-[pyrrole(N-R2)]-C(=O)-CH2-CH2-CH2-R3

Structure (I): same with stereochemistry at the carbon bearing R1.

| Compound No. | R¹ | R² | R³ |
|---|---|---|---|
| 169 | Et | Me | 3,4-di-Me—Ph |
| 170 | Et | Me | 3,5-di-Me—Ph |
| 171 | Et | Me | 2-Et—Ph |
| 172 | Et | Me | 3-Et—Ph |
| 173 | Et | Me | 4-Et—Ph |
| 174 | Et | Me | 2-cPr—Ph |
| 175 | Et | Me | 3-cPr—Ph |
| 176 | Et | Me | 4-cPr—Ph |
| 177 | Et | Me | 2-iPr—Ph |
| 178 | Et | Me | 3-iPr—Ph |
| 179 | Et | Me | 4-iPr—Ph |
| 180 | Et | Me | 2-tBu—Ph |
| 181 | Et | Me | 3-tBu—Ph |
| 182 | Et | Me | 4-tBu—Ph |
| 183 | Et | Me | 2-tBu—Ph |
| 184 | Et | Me | 3-tBu—Ph |
| 185 | Et | Me | 4-tBu—Ph |
| 186 | Et | Me | 2-MeO—Ph |
| 187 | Et | Me | 3-MeO—Ph |
| 188 | Et | Me | 4-MeO—Ph |
| 189 | Et | Me | 2,3-di-MeO—Ph |
| 190 | Et | Me | 2,4-di-MeO—Ph |
| 191 | Et | Me | 2,5-di-MeO—Ph |
| 192 | Et | Me | 3,4-di-MeO—Ph |
| 193 | Et | Me | 3,5-di-MeO—Ph |
| 194 | Et | Me | 2-EtO—Ph |
| 195 | Et | Me | 3-EtO—Ph |
| 196 | Et | Me | 4-EtO—Ph |
| 197 | Et | Me | 2-iPrO—Ph |
| 198 | Et | Me | 3-iPrO—Ph |
| 199 | Et | Me | 4-iPrO—Ph |
| 200 | Et | Me | 2-Me-3-MeO—Ph |
| 201 | Et | Me | 2-Me-4-MeO—Ph |
| 202 | Et | Me | 2-Me-5-MeO—Ph |
| 203 | Et | Me | 3-Me-4-MeO—Ph |
| 204 | Et | Me | 3-Me-5-MeO—Ph |
| 205 | Et | Me | 2-MeO-3-Me—Ph |
| 206 | Et | Me | 2-MeO-4-Me—Ph |
| 207 | Et | Me | 2-MeO-5-Me—Ph |
| 208 | Et | Me | 3-MeO-4-Me—Ph |
| 209 | Et | Me | 3-MeO-5-Me—Ph |
| 210 | Et | Me | 2-CF₃—Ph |
| 211 | Et | Me | 3-CF₃—Ph |
| 212 | Et | Me | 4-CF₃—Ph |
| 213 | Et | Me | 3,5-di-CF₃—Ph |
| 214 | Et | Me | 2-Ac—Ph |
| 215 | Et | Me | 3-Ac—Ph |
| 216 | Et | Me | 4-Ac—Ph |
| 217 | Et | Me | 2-CN—Ph |
| 218 | Et | Me | 3-CN—Ph |
| 219 | Et | Me | 4-CN—Ph |
| 220 | Et | Et | 2-F—Ph |
| 221 | Et | Et | 3-F—Ph |
| 222 | Et | Et | 4-F—Ph |
| 223 | Et | Et | 2,3-di-F—Ph |
| 224 | Et | Et | 2,4-di-F—Ph |
| 225 | Et | Et | 2,5-di-F—Ph |
| 226 | Et | Et | 3,4-di-F—Ph |
| 227 | Et | Et | 3,5-di-F—Ph |
| 228 | Et | Et | 2-Cl—Ph |
| 229 | Et | Et | 3-Cl—Ph |
| 230 | Et | Et | 4-Cl—Ph |
| 231 | Et | Et | 2,3-di-Cl—Ph |
| 232 | Et | Et | 2,4-di-Cl—Ph |
| 233 | Et | Et | 2,5-di-Cl—Ph |
| 234 | Et | Et | 3,4-di-Cl—Ph |
| 235 | Et | Et | 3,5-di-Cl—Ph |
| 236 | Et | Et | 2-Me—Ph |
| 237 | Et | Et | 3-Me—Ph |
| 238 | Et | Et | 4-Me—Ph |
| 239 | Et | Et | 2,3-di-Me—Ph |
| 240 | Et | Et | 2,4-di-Me—Ph |
| 241 | Et | Et | 2,5-di-Me—Ph |
| 242 | Et | Et | 3,4-di-Me—Ph |
| 243 | Et | Et | 3,5-di-Me—Ph |
| 244 | Et | Et | 2-Et—Ph |
| 245 | Et | Et | 3-Et—Ph |
| 246 | Et | Et | 4-Et—Ph |
| 247 | Et | Et | 2-cPr—Ph |
| 248 | Et | Et | 3-cPr—Ph |
| 249 | Et | Et | 4-cPr—Ph |
| 250 | Et | Et | 2-iPr—Ph |
| 251 | Et | Et | 3-iPr—Ph |
| 252 | Et | Et | 4-iPr—Ph |
| 253 | Et | Et | 2-tBu—Ph |
| 254 | Et | Et | 3-tBu—Ph |
| 255 | Et | Et | 4-tBu—Ph |
| 256 | Et | Et | 2-tBu—Ph |
| 257 | Et | Et | 3-tBu—Ph |
| 258 | Et | Et | 4-tBu—Ph |
| 259 | Et | Et | 2-MeO—Ph |
| 260 | Et | Et | 3-MeO—Ph |
| 261 | Et | Et | 4-MeO—Ph |
| 262 | Et | Et | 2,3-di-Meo—Ph |
| 263 | Et | Et | 2,4-di-MeO—Ph |
| 264 | Et | Et | 2,5-di-MeO—Ph |
| 265 | Et | Et | 3,4-di-MeO—Ph |
| 266 | Et | Et | 3,5-di-MeO—Ph |
| 267 | Et | Et | 2-EtO—Ph |
| 268 | Et | Et | 3-EtO—Ph |
| 269 | Et | Et | 4-EtO—Ph |
| 270 | Et | Et | 2-iPrO—Ph |
| 271 | Et | Et | 3-iPrO—Ph |
| 272 | Et | Et | 4-iPrO—Ph |
| 273 | Et | Et | 2-Me-3-MeO—Ph |
| 274 | Et | Et | 2-Me-4-MeO—Ph |
| 275 | Et | Et | 2-Me-5-MeO—Ph |
| 276 | Et | Et | 3-Me-4-MeO—Ph |
| 277 | Et | Et | 3-Me-5-MeO—Ph |
| 278 | Et | Et | 2-MeO-3-Me—Ph |
| 279 | Et | Et | 2-MeO-4-Me—Ph |
| 280 | Et | Et | 2-MeO-5-Me—Ph |
| 281 | Et | Et | 3-MeO-4-Me—Ph |
| 282 | Et | Et | 3-MeO-S-Me—Ph |
| 283 | Et | Et | 2-CF₃—Ph |
| 284 | Et | Et | 3-CF₃—Ph |
| 285 | Et | Et | 4-CF₃—Ph |
| 286 | Et | Et | 3,5-di-CF₃—Ph |
| 287 | Et | Et | 2-Ac—Ph |
| 288 | Et | Et | 3-Ac—Ph |

TABLE 1-continued

[Chemical Formula 101]

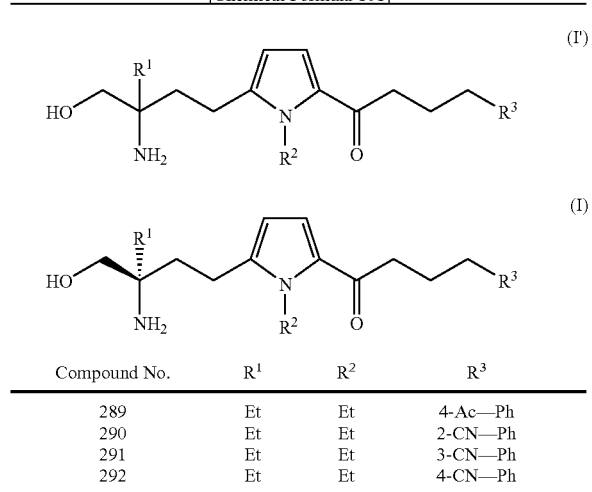

| Compound No. | $R^1$ | $R^2$ | $R^3$ |
|---|---|---|---|
| 289 | Et | Et | 4-Ac—Ph |
| 290 | Et | Et | 2-CN—Ph |
| 291 | Et | Et | 3-CN—Ph |
| 292 | Et | Et | 4-CN—Ph |

In the above Table 1, preferred examples of compound (I) or (I') serving as an active ingredient of the present invention include Exemplary Compound Nos. 17 to 24, 40 to 47, 54 to 63, 72, 73, 90 to 97, 113 to 120, 127 to 136, 145, 146, 163 to 170, 186 to 193, 200 to 209, 218, 219, 236 to 243, 259 to 266, 273 to 282, 291 and 292, more preferably Exemplary Compound Nos. 17 to 24, 54 to 63, 72, 73, 163 to 170, 192, 203, 208 and 219, and even more preferred examples include Exemplary Compound No. 17: 2-amino-2-methyl-4-{1-methyl-5-[4-(2-methylphenyl)butanoyl]pyrrol-2-yl}butan-1-ol, Exemplary Compound No. 18: 2-amino-2-methyl-4-{1-methyl-5-[4-(3-methylphenyl)butanoyl]pyrrol-2-yl}butan-1-ol, Exemplary Compound No. 19: 2-amino-2-methyl-4-{1-methyl-5-[4-(4-methylphenyl)butanoyl]pyrrol-2-yl}butan-1-ol, Exemplary Compound No. 20: 2-amino-2-methyl-4-{1-methyl-5-[4-(2,3-dimethylphenyl)butanoyl]pyrrol-2-yl}butan-1-ol, Exemplary Compound No. 21: 2-amino-2-methyl-4-{1-methyl-5-[4-(2,4-dimethylphenyl)butanoyl]pyrrol-2-yl}butan-1-ol, Exemplary Compound No. 22: 2-amino-2-methyl-4-{1-methyl-5-[4-(2,5-dimethylphenyl)butanoyl]pyrrol-2-yl}butan-1-ol, Exemplary Compound No. 23: 2-amino-2-methyl-4-{1-methyl-5-[4-(3,4-dimethylphenyl)butanoyl]pyrrol-2-yl}butan-1-ol, Exemplary Compound No. 24: 2-amino-2-methyl-4-{1-methyl-5-[4-(3,5-dimethylphenyl)butanoyl]pyrrol-2-yl}butan-1-ol, Exemplary Compound No. 57: 2-amino-2-methyl-4-{1-methyl-5-[4-(3-methyl-4-methoxyphenyl)butanoyl]pyrrol-2-yl}butan-1-ol, Exemplary Compound No. 62: 2-amino-2-methyl-4-{1-methyl-5-[4-(3-methoxy-4-methylphenyl)butanoyl]pyrrol-2-yl}butan-1-ol and Exemplary Compound No. 73: 2-amino-2-methyl-4-{1-methyl-5-[4-(4-cyanophenyl)butanoyl]pyrrol-2-yl}butan-1-ol.

A compound having general formula (I) serving as an active ingredient of the present invention can be produced according to the processes described below.

Process A is a process by which a compound having general formula (I) is produced from a compound having general formula (II) or general formula (III).

[Chemical Formula 11]

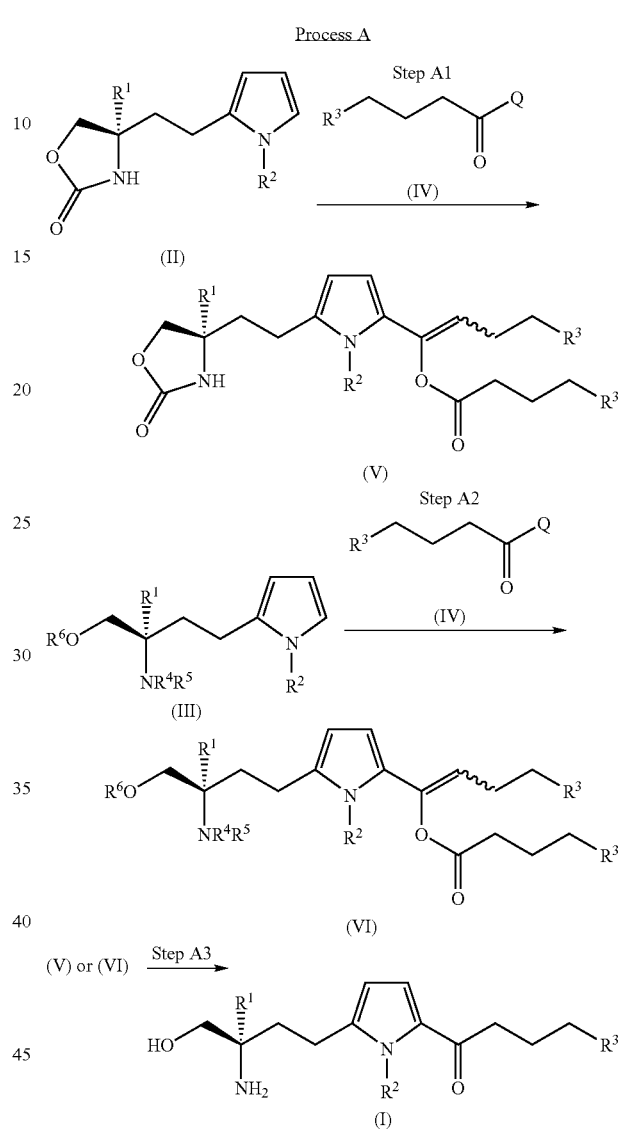

In the aforementioned formulae, $R^1$, $R^2$ and $R^3$ are the same as previously defined, $R^4$ and $R^5$ may be the same or different and represent an amino protecting group, $R^6$ represents a "hydroxyl protecting group" and Q represents a leaving group.

There are no particular limitations on the "amino protecting group" in the definition of $R^4$ and $R^5$ provided it is an amino protecting group used in the field of organic synthetic chemistry, and examples include lower aliphatic acyl groups and lower alkoxycarbonyl groups, and preferably an acetyl group or t-butoxycarbonyl group.

There are no particular limitations on the "hydroxyl protecting group" in the definition of $R^6$ provided it is a hydroxyl protecting group used in the field of organic synthetic chemistry, and examples include lower aliphatic acyl groups, and preferably an acetyl group.

There are no particular limitations on the leaving group in the definition of Q provided it is a leaving group used in the field of organic synthetic chemistry, and examples include halogen groups such as a chlorine, bromine or iodine atom and sulfonate groups such as a methane sulfonate group or p-toluene sulfonate group, and preferably a chlorine atom.

Step A1:

In Step A1, a compound having general formula (V) is produced, and this is carried out by reacting a compound having general formula (II) and a compound having general formula (IV) in an inert solvent in the presence of a base.

There are no particular limitations on the inert solvent used in the aforementioned reaction provided it does not react with the compound having general formula (IV), and examples include aliphatic hydrocarbons such as hexane, heptane, ligroin or petroleum ether; aromatic hydrocarbons such as toluene, benzene or xylene; halogenated hydrocarbons such as dichloromethane, chloroform, carbon tetrachloride, dichloroethane, chlorobenzene or dichlorobenzene; ethers such as diethyl ether, diisopropyl ether, tetrahydrofuran, dioxane, dimethoxyethane or diethylene glycol dimethyl ether; lower alkyl nitriles such as acetonitrile or propionitrile; and, lower alkyl ketones such as acetone or methyl ethyl ketone, preferably aromatic hydrocarbons, and more preferably benzene, toluene or xylene.

There are no particular limitations on the base used in the aforementioned reaction provided it activates the compound having general formula (IV), and examples include organic amines such as triethylamine, tributylamine, diisopropylethylamine, N-methylmorpholine, pyridine, 4-(N,N-dimethylamino)pyridine, 4-pyrrolidinopyridine, N,N-dimethylaniline, N,N-diethylaniline, 1,5-diazabicyclo[4.3.0]non-5-ene, 1,4-diazabicyclo[2.2.2]octane (DABCO) or 1,8-diazabicyclo[5.4.0]-7-undecene (DBU), and preferably 4-(N,N-dimethylaminopyridine) or 4-pyrrolidinopyridine.

Although the reaction temperature varies depending on the type of raw material compound, solvent, base and so forth, it is normally from 0 to 200° C. and preferably from room temperature to 150° C.

Although the reaction time varies depending on the type of raw material compound, base, solvent, reaction temperature and so forth, it is normally from 15 minutes to 7 days, and preferably from 6 hours to 3 days.

Step A2:

In Step A2, a compound having general formula (VI) is produced, and this is carried out using the same method as Step A1 using a compound having general formula (III) and a compound having general formula (IV).

Step A3:

In Step A3, a compound having general formula (I) is produced, and this is carried out by hydrolyzing a compound having general formula (V) or general formula (VI) in an inert solvent in the presence of a base.

There are no particular limitations on the inert solvent used in the aforementioned reactions, and examples include ethers such as diethyl ether, diisopropyl ether, tetrahydrofuran, dioxane, dimethoxyethane, or diethylene glycol dimethyl ether; aromatic hydrocarbons such as toluene, benzene or xylene; halogenated hydrocarbons such as dichloromethane, chloroform, carbon tetrachloride, dichloroethane, chlorobenzene or dichlorobenzene; lower alkyl nitriles such as acetonitrile or propionitrile; amides such as formamide, N,N-dimethylformamide, N,N-dimethylacetamide or hexamethyl phosphoric triamide; lower alkyl alcohols such as methanol, ethanol, propanol or butanol; and water, preferably alcohols or ethers, and more preferably a mixed solvent of methanol and tetrahydrofuran. The reaction speed may be increased by adding water as co-solvent.

There are no particular limitations on the base used in the aforementioned reactions provided it only acts in the desired hydrolysis reaction, and examples include alkaline metal carbonates such as lithium carbonate, sodium carbonate or potassium carbonate; alkaline metal bicarbonates such as lithium hydrogencarbonate, sodium hydrogencarbonate or potassium hydrogencarbonate; alkaline metal hydrides such as lithium hydride, sodium hydride or potassium hydride; alkaline metal hydroxides such as lithium hydroxide, sodium hydroxide or potassium hydroxide; and, alkaline metal alkoxides such as lithium methoxide, sodium methoxide, sodium ethoxide or potassium t-butoxide, preferably alkaline metal hydroxides, and more preferably lithium hydroxide or sodium hydroxide.

Although the reaction temperature varies depending on the type of raw material compound, solvent, base and so forth, it is normally from −78 to 200° C. and preferably from −50 to 150° C.

Although the reaction time varies depending on the type of raw material compound, base, solvent, reaction temperature and. so forth, it is normally from 15 minutes to 48 hours, and preferably from 30 minutes to 8 hours.

The desired compounds of each step of Process A are recovered from the reaction mixture in accordance with ordinary methods. For example, in the case of suitably neutralizing the reaction mixture or when impurities are present, an organic solvent such as ethyl acetate that is not miscible with water is added after removing the impurities by filtration, and after washing with water and so forth, the organic layer containing the desired compound is separated, and after drying with anhydrous magnesium sulfate or anhydrous sodium sulfate, the desired compound is obtained by distilling off the solvent. The resulting desired compound can be separated and purified as necessary by suitably combining ordinary methods, such as recrystallization, reprecipitation or other method commonly used for separation and purification of organic compounds, examples of which include absorption column chromatography using a carrier such as silica gel, alumina or magnesium-silica gel-based Florisil; a method using a synthetic adsorbent such as partition column chromatography using a carrier such as Sephadex LH-20 (Pharmacia), Amberlite XAD-11 (Rohm and Haas) or Diaion HP-20 (Mitsubishi Chemical), a method using ion exchange chromatography, and a forward-phase, reverse-phase column chromatography method using silica gel or alkylated silica gel (and preferably high-performance liquid column chromatography), and eluting with a suitable eluent.

Furthermore, when it is necessary to separate isomers, isomers can be separated by the aforementioned separation and purification means at a suitable time either following completion of the reaction of each step or following completion of a desired step.

Process B is an alternative process of Process A in which a compound having general formula (I) is produced from a compound having general formula (II) or general formula (III).

[Chemical Formula 12]

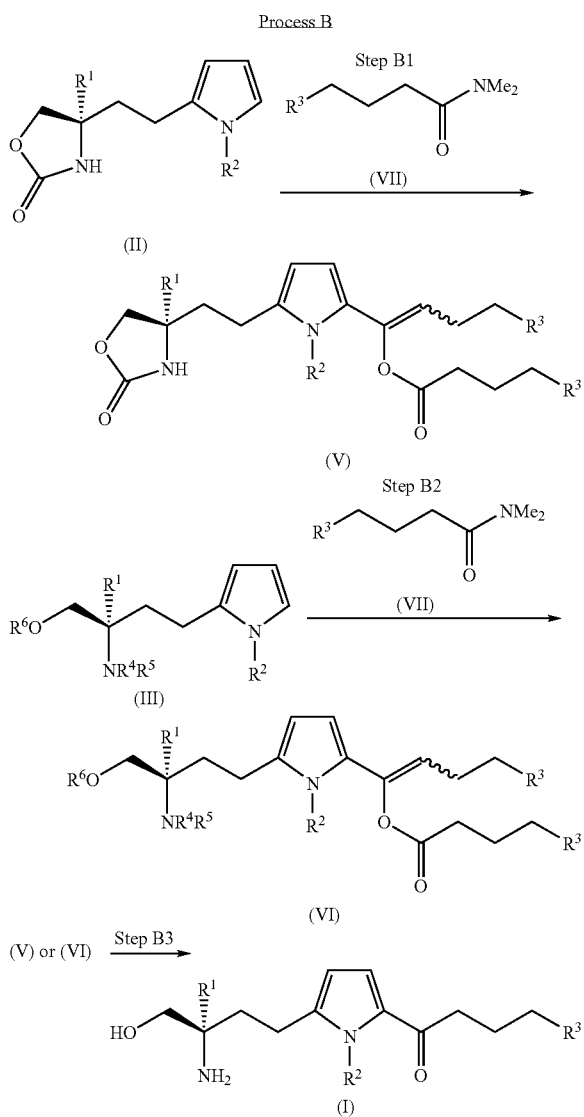

In the above formulae, $R^1$, $R^2_1$, $R^3$, $R^4_1$, $R^5$ and $R^6$ are the same as previously defined.

Step B1:

In Step B1, a compound having formula (V) is produced, and this is carried out by reacting a compound having general formula (II) and a compound having general formula (VII) in an inert solvent in the presence of phosphorus oxychloride or oxalyl chloride. This reaction is carried out in accordance with a known method (such as the method described in J. Med. Chem., 40, 3381 (1997)).

There are no particular limitations on the inert solvent used in the aforementioned reaction, and examples include aliphatic hydrocarbons such as hexane, heptane, ligroin or petroleum ether; aromatic hydrocarbons such as toluene, benzene or xylene; halogenated hydrocarbons such as dichloromethane, chloroform, carbon tetrachloride, dichloroethane, chlorobenzene or dichlorobenzene; ethers such as diethyl ether, diisopropyl ether, tetrahydrofuran, dioxane, dimethoxyethane or diethylene glycol dimethyl ether; lower alkyl nitriles such as acetonitrile or propionitrile; and lower alkyl ketones such as acetone or methyl ethyl ketone, preferably aromatic hydrocarbons, and more preferably benzene or toluene.

Although the reaction temperature varies depending on the type of raw material compound, solvent, base and so forth, it is normally from 0 to 200° C. and preferably from room temperature to 150° C.

Although the reaction time varies depending on the type of raw material compound, base, solvent, reaction temperature and so forth, it is normally from 15 minutes to 7 days, and preferably from 6 hours to 3 days.

Step B2:

In Step B2, a compound having general formula (VI) is produced, and this is carried out using the same method as Step B1 using a compound having general formula (III) and a compound having general formula (VII).

Step B3:

In Step B3, a compound having general formula (I) is produced, and this is carried out by hydrolyzing a compound having general formula (V) or a compound having general formula (VI) in an inert solvent in the presence of a base.

There are no particular limitations on the inert solvent used in the aforementioned reactions, and examples include ethers such as diethyl ether, diisopropyl ether, tetrahydrofuran, dioxane, dimethoxyethane, or diethylene glycol dimethyl ether; alcohols such as methanol, ethanol, n-propanol, isopropanol, n-butanol, isobutanol, t-butanol, isoamyl alcohol, diethylene glycol, glycerin, octanol, cyclohexanol or methyl cellosolve; amides such as formamide, N,N-dimethylformamide, N,N-dimethylacetamide or hexamethyl phosphoric triamide; water; or mixed solvents of the aforementioned solvents or mixed solvents of the aforementioned solvents and water, preferably mixed solvents of alcohols and ethers and water or mixed solvents of alcohols and water, and more preferably a mixed solvent of methanol, tetrahydrofuran and water or a mixed solvent of methanol and water.

There are no particular limitations on the base used in the aforementioned reactions provided it only acts in the desired hydrolysis reaction, and examples include alkaline metal carbonates such as lithium carbonate, sodium carbonate or potassium carbonate; alkaline metal bicarbonates such as lithium hydrogencarbonate, sodium hydrogencarbonate or potassium hydrogencarbonate; alkaline metal hydrides such as lithium hydride, sodium hydride or potassium hydride; alkaline metal hydroxides such as lithium hydroxide, sodium hydroxide or potassium hydroxide; and, alkaline metal alkoxides such as lithium methoxide, sodium methoxide, sodium ethoxide or potassium t-butoxide, preferably alkaline metal hydroxides, and more preferably sodium hydroxide.

Although the reaction temperature varies depending on the type of raw material compound, solvent, base and so forth, it is normally from −78 to 150° C., preferably from −50 to 100° C., and more preferably in the vicinity of room temperature.

Although the reaction time varies depending on the type of raw material compound, base, solvent, reaction temperature and so forth, it is normally from 15 minutes to 48 hours, and preferably from 30 minutes to 6 hours.

The desired compounds of each step of Process B are collected from the reaction mixture in accordance with ordinary methods. For example, in the case of suitably neutralizing the reaction mixture or when impurities are present, an organic solvent such as ethyl acetate that is not miscible with water is added after removing the impurities by filtration, and after washing with water and so forth, the organic layer containing the desired compound is separated, and after drying with anhydrous magnesium sulfate or anhydrous sodium sulfate, the desired compound is obtained by distilling off the solvent. The resulting desired compound can be separated and purified as necessary by suitably combining ordinary methods, such as recrystallization, reprecipitation or other method commonly used for separation and purification of organic compounds, examples of which include absorption column chromatography using a carrier such as silica gel, alumina or magnesium-silica gel-based Florisil; a method using a synthetic adsorbent such as partition column chromatography using a carrier such as Sephadex LH-20 (Pharmacia), Amberlite XAD-11 (Rohm and Haas) or Diaion HP-20 (Mitsubishi Chemical), a method using ion exchange chromatography, and a forward-phase, reverse-phase column chromatography method using silica gel or alkylated silica gel (and preferably high-performance liquid column chromatography), and eluting with a suitable eluent.

Furthermore, when it is necessary to separate isomers, isomers can be separated by the aforementioned separation and purification means at a suitable time either following completion of the reaction of each step or following completion of a desired step.

Process C is a process for producing a compound having general formula (III).

[Chemical Formula 13]

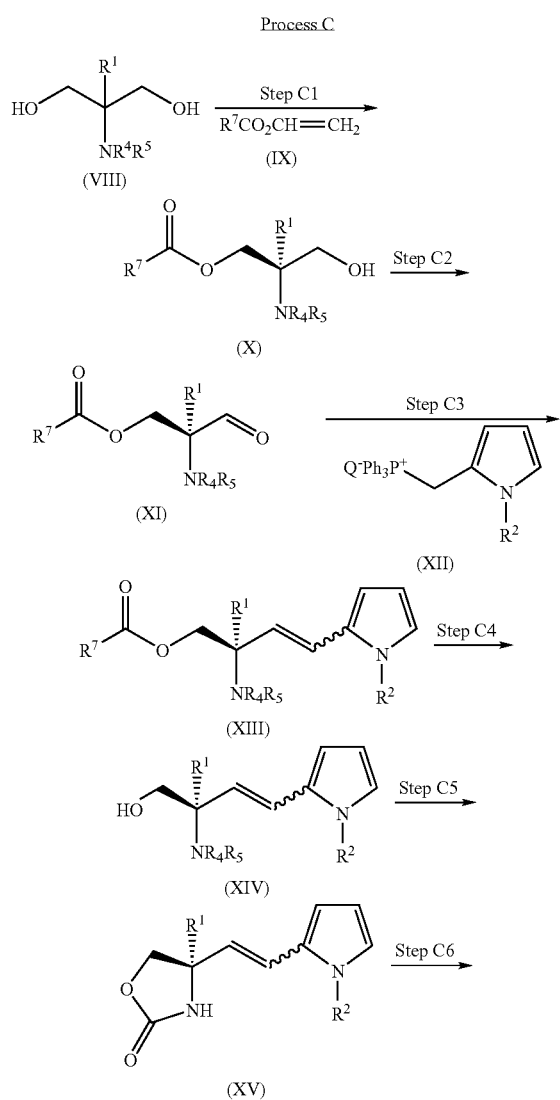

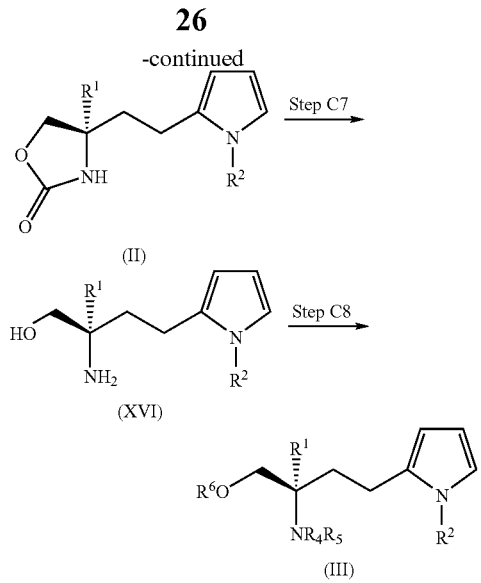

In the above formulae, $R^1$, $R^2$, $R^4$, $R^5$, $R^6$ and Q are the same as previously defined.

$R^7$ represents an alkyl group having 1 to 20 carbon atoms, an alkyl group having 2 to 20 carbon atoms interposed with a hetero atom, an alkyl group having 1 to 20 carbon atoms substituted with an aryl group or aromatic heterocyclic group, an alkynyl group having 2 to 20 carbon atoms, an alkynyl group having 3 to 20 carbon atoms interposed with a hetero atom, an alkynyl group having 2 to 20 carbon atoms substituted with an aryl group or aromatic heterocyclic group, an alkenyl group having 2 to 20 carbon atoms, an alkenyl group having 3 to 20 carbon atoms interposed with a hetero atom, an alkenyl group having 2 to 20 carbon atoms substituted with an aryl group or aromatic heterocyclic group, an alkyl group having 2 to 20 carbon atoms substituted with an aryl group or aromatic heterocyclic group and interposed with a hetero atom, or a cycloalkyl group having 3 to 20 carbon atoms.

An "alkyl group having 1 to 20 carbon atoms" in the definition of $R^7$ includes linear or branched alkyl groups having 1 to 20 carbon atoms such as the aforementioned "lower alkyl group", or a heptyl, 1-methylhexyl, 2-methylhexyl, 3-methylhexyl, 4-methylhexyl, 5-methylhexyl, 1-propylbutyl, 4,4-dimethylpentyl, octyl, 1-methylheptyl, 2-methylheptyl, 3-methylheptyl, 4-methylheptyl, 5-methylheptyl, 6-methylheptyl, 1-propylpentyl, 2-ethylhexyl, 5,5-dimethylhexyl, nonyl, 3-methyloctyl, 4-methyloctyl, 5-methyloctyl, 6-methyloctyl, 1-propylhexyl, 2-ethylheptyl, 6,6-dimethylheptyl, decyl, 1-methylnonyl, 3-methylnonyl, 8-methylnonyl, 3-ethyloctyl, 3,7-dimethyloctyl, 7,7-dimethyloctyl, undecyl, 4,8-dimethylnonyl, dodecyl, tridecyl, tetradecyl, pentadecyl, 3,7,11-trimethyldodecyl, hexadecyl, 4,8,12-trimethyltridecyl, 1-methylpentadecyl, 14-methylpentadecyl, 13,13-dimethyltetradecyl, heptadecyl, 15-methylhexadecyl, octadecyl, 1-methylheptadecyl, nonadecyl, eicosyl or 3,7,11,15-tetramethylhexadecyl group and preferably alkyl groups having 2 to 10 carbon atoms.

In the above, an "alkyl group having 2 to 20 carbon atoms interposed with a hetero atom" in the definition of $R^7$ indicates groups in which an "alkyl group having 2 to 20 carbon atoms" of the aforementioned "alkyl groups having 1 to 20 carbon atoms" may be the same or different, and are interposed with 1 or 2 sulfur atoms, oxygen atoms or nitrogen atoms, examples of which include alkyl groups having 2 to 20 carbon atoms interposed with 1 or two sulfur atoms such as methylthiomethyl, 1-methylthioethyl, 2-methylthioethyl, ethylthiomethyl, 1-methylthiopropyl, 2-methylthiopropyl, 3-methylthiopropyl, 2-ethylthioethyl, 2-methyl-2-methylthioethyl, 1-methylthiobutyl, 2-methylthiobutyl, 3-methylthiobutyl, 2-ethylthiopropyl, 3-methyl-3-methylthiopropyl, 4-methylthiopentyl, 3-methylthiopentyl, 2-methylthiopentyl, 1-methylthiopentyl, 3,3-dimethylthiobutyl, 2,2-dimethylthiobutyl, 1,1-dimethylthiobutyl, 1-methyl-2-methylthiobutyl, 1,3-dimethylthiobutyl, 2,3-dimethylthiobutyl, 2-ethylthiobutyl, 1-methylthiohexyl, 2-methylthiohexyl, 3-methylthiohexyl, 4-methylthiohexyl, 5-methylthiohexyl, 1-propylthiobutyl, 4-methyl-4-methylthiopentyl, 1-methylthioheptyl, 2-methylthioheptyl, 3-methylthioheptyl, 4-methylthioheptyl, 5-methylthioheptyl, 6-methylthioheptyl, 1-propylthiopentyl, 2-ethylthiohexyl, 5-methyl-5-methylthiohexyl, 3-methylthiooctyl, 4-methylthiooctyl, 5-methylthiooctyl, 6-methylthiooctyl, 1-propylthiohexyl, 2-ethylthioheptyl, 6-methyl-6-methylthioheptyl, 1-methylthiononyl, 3-methylthiononyl, 8-methylthiononyl, 3-ethylthiooctyl, 3-methyl-7-methylthiooctyl, 7,7-dimethylthiooctyl, 4-methyl-B-methylthiononyl, 3,7-dimethyl-11-methylthiododecyl, 4,8-dimethyl-12-methylthiotridecyl, 1-methylthiopentadecyl, 14-methylthiopentadecyl, 13-methyl-13-methylthiotetradecyl, 15-methylthiohexadecyl, 1-methylthioheptadecyl or 3,7,11-trimethyl-15-methylthiohexadecyl; alkyl groups having 2 to 20 carbon atoms interposed with 1 or 2 oxygen atoms such as methyloxymethyl, 1-methyloxyethyl, 2-methyloxyethyl, ethyloxymethyl, 1-methyloxypropyl, 2-methyloxypropyl, 3-methyloxypropyl, 2-ethyloxyethyl, 2-methyl-2-methyloxyethyl, 1-methyloxybutyl, 2-methyloxybutyl, 3-methyloxybutyl, 2-ethyloxypropyl, 3-methyl-3-methyloxypropyl, 4-methyloxypentyl, 3-methyloxypentyl, 2-methyloxypentyl, 1-methyloxypentyl, 3,3-dimethyloxybutyl, 2,2-dimethyloxybutyl, 1,1-dimethyloxybutyl, 1-methyl-2-methyloxybutyl, 1,3-dimethyloxybutyl, 2,3-dimethyloxybutyl., 2-ethyloxybutyl, 1-methyloxyhexyl, 2-methyloxyhexyl, 3-methyloxyhexyl, 4-methyloxyhexyl, 5-methyloxyhexyl, 1-propyloxybutyl, 4-methyl-4-methyloxypentyl, 1-methyloxyheptyl, 2-methyloxyheptyl, 3-methyloxyheptyl, 4-methyloxyheptyl, 5-methyloxyheptyl, 6-methyloxyheptyl, 1-propyloxypentyl, 2-ethyloxyhexyl, 5-methyl-5-methyloxyhexyl, 3-methyloxyoctyl, 4-methyloxyoctyl, 5-methyloxyoctyl, 6-methyloxyoctyl, 1-propyloxyhexyl, 2-ethyloxyheptyl, 6-methyl-6-methyloxyheptyl, 1-methyloxynonyl, 3-methyloxynonyl, 8-methyloxynonyl, 3-ethyloxyoctyl, 3-methyl-7-methyloxyoctyl, 7,7-dimethyloxyoctyl, 4-methyl-8-methyloxynonyl, 3,7-dimethyl-11-methyloxydodecyl, 4,8-dimethyl-12-methyloxytridecyl, 1-methyloxypentadecyl, 14-methyloxypentadecyl, 13-methyl-13-methyloxytetradecyl, 15-methyloxyhexadecyl, 1-methyloxyheptadecyl or 3,7,11-trimethyl-15-methyloxyhexadecyl;

alkyl groups having 2 to 20 carbon atoms interposed with 1 or 2 nitrogen atoms such as N-methylaminomethyl, 1-(N-methylamino)ethyl, 2-(N-methylamino)ethyl, N-ethylaminomethyl, 1-(N-methylamino)propyl, 2-(N-methylamino)propyl, 3-(N-methylamino)propyl, 2-(N-ethylamino)ethyl, 2-(N,N-dimethylamino)ethyl, 1-(N-methylamino)butyl, 2-(N-methylamino)butyl, 3-(N-methylamino)butyl, 2-(N-ethylamino)propyl, 3-(N,N-dimethylamino)propyl, 4-(N-methylamino)pentyl, 3-(N-methylamino)pentyl, 2-(N-methylamino)pentyl, 1-(N-methylamino)pentyl, 3-(N,N-dimethylamino)butyl, 2-(N,N-dimethylamino)butyl, 1-(N,N-dimethylamino)butyl, 1-methyl-2-(N-methylamino)butyl, 1,3-di(N-methylamino)butyl, 2,3-di(N-methylamino)butyl, 2-(N-ethylamino)butyl, 1-(N-methylamino)hexyl, 2-(N-methylamino)hexyl, 3-(N-methylamino)hexyl, 4-(N-methylamino)hexyl, 5-(N-methylamino)hexyl, 1-(N-propylamino)butyl, 4-methyl-4-(N-methylamino)pentyl, 1-(N-methylamino)heptyl, 2-(N-methylamino)heptyl, 3-(N-methylamino)heptyl, 4-(N-methylamino)heptyl, 5-(N-methylamino)heptyl, 6-(N-methylamino)heptyl, 1-(N-propylamino)pentyl, 2-(N-ethylamino)hexyl, 5-methyl-5-(N-methylamino)hexyl, 3-(N-methylamino)octyl, 4-(N-methylamino)octyl, 5-(N-methylamino)octyl, 6-(N-methylamino)octyl, 1-(N-propylamino)hexyl, 2-(N-ethylamino)heptyl, 6-methyl-6-(N-methylamino)heptyl, 1-(N-methylamino)nonyl, 3-(N-methylamino)nonyl, 8-(N-methylamino)nonyl, 3-(N-ethylamino)octyl, 3-methyl-7-(N-methylamino)octyl, 7,7-di(N-methylamino)octyl, 4-methyl-8-(N-methylamino)nonyl, 3,7-dimethyl-11-(N-methylamino)dodecyl, 4,8-dimethyl-12-(N-methylamino)tridecyl, 1-(N-methylamino)pentadecyl, 14-(N-methylamino)pentadecyl, 13-methyl-13-(N-methylamino)tetradecyl, 15-(N-methylamino)hexadecyl, 1-(N-methylamino)heptadecyl or 3,7,11-trimethyl-15-(N-methylamino)hexadecyl, preferably alkyl groups having 2 to 10 carbon atoms interposed with a hetero atom, and more preferably alkyl groups having 2 to 5 carbon atoms interposed with a hetero atom.

In the above, an "alkyl group having 1 to 20 carbon atoms substituted with an aryl group or aromatic heterocyclic group" in the definition of $R^7$ is a group in which the aforementioned "alkyl group having 1 to 20 carbon atoms" may be the same or different, and is substituted with 1 to 3 "aryl groups" or "aromatic heterocyclic groups", and preferably an alkyl group having 2 to 5 carbon atoms substituted with an aryl group or aromatic heterocyclic group.

Examples of "aryl groups" include aromatic hydrocarbon groups having 5 to 14 carbon atoms such as a phenyl, indenyl, naphthyl, phenylethenyl or anthracenyl group, and preferably a phenyl group.

The aforementioned "aryl group" may also be condensed into a ring with a cycloalkyl group having 3 to 10 carbon atoms such as a 2-indanyl group.

An "aromatic heterocyclic group" indicates a "5- to 7-member aromatic heterocyclic group" containing 1 to 3 sulfur atoms, oxygen atoms or nitrogen atoms, examples of which include aromatic heterocyclic groups such as a furyl, thienyl, pyrrolyl, azepinyl, pyrazolyl, imidazolyl, oxazolyl, isoxazolyl, thiazolyl, isothiazolyl, 1,2,3-oxadiazolyl, triazolyl, tetrazolyl, thiadiazolyl, pyranyl, pyridyl, pyridazinyl, pyrimidinyl or pyrazinyl group, and preferably a "5- to 7-member heterocyclic group" that contains at least one nitrogen atom and optionally contains an oxygen atom or sulfur atom, examples of which include a pyrrolyl, azepinyl, pyrazolyl, imidazolyl, oxazolyl, isoxazolyl, thiazolyl, isothiazolyl, 1,2,3-oxadiazolyl, triazolyl, tetrazolyl, thiadiazolyl, pyridyl, pyridazinyl, pyrimidinyl or pyrazinyl group.

The aforementioned "5- to 7-member heterocyclic group" may be condensed into a ring with other cyclic groups, examples of which include isobenzofuranyl, chromenyl, xanthenyl, phenoxathiinyl, indolizinyl, isoindolyl, indolyl, indazolyl, prinyl, quinolizinyl, isoquinolyl, quinolyl, phthalazinyl, naphthyridinyl, quinoxalinyl, quinazolinyl, carbazolyl, carbolinyl, acridinyl and isoindolinyl, and preferably isobenzofuranyl, chromenyl, xanthenyl, phenoxathiinyl, indolizinyl, isoindolyl, indolyl or indazolyl.

In the above, an "alkynyl group having 2 to 20 carbon atoms" in the definition of $R^7$ is a linear or branched alkynyl group having 2 to 20 carbon atoms, examples of which include ethynyl, 2-propynyl, 1-ethyl-2-propynyl, 1-ethyl-2-propynyl, 2-butynyl, 1-methyl-2-butynyl, 1-ethyl-2-butynyl, 3-butynyl, 1-methyl-3-butynyl, 2-methyl-3-butynyl, 1-ethyl-3-butynyl, 2-pentynyl, 1-methyl-2-pentynyl, 3-pentynyl, 1-methyl-3-pentynyl, 2-methyl-3-pentynyl, 4-pentynyl, 1-methyl-4-pentynyl, 2-methyl-4-pentynyl, 2-hexynyl, 3-hexynyl, 4-hexynyl, 5-hexynyl, 2-heptynyl, 3-heptynyl, 4-heptynyl, 5-heptynyl, 6-heptynyl, 1-methyl-5-hexynyl, 2-methyl-5-hexynyl, 3-methyl-5-hexynyl, 4-methyl-5-hexynyl, 5-methyl-3-hexynyl, 1-propyl-3-butynyl, 4,4-dimethyl-2-pentynyl, 7-octynyl, 1-methyl-6-heptynyl, 2-methyl-6-heptynyl, 3-methyl-6-heptynyl, 4-methyl-6-heptynyl, 5-methyl-6-heptynyl, 6-methyl-4-heptynyl, 1-propyl-4-pentynyl, 2-ethyl-5-hexynyl, 5,5-dimethyl-3-hexynyl, 7-nonynyl, 3-methyl-7-octynyl, 4-methyl-7-octynyl, 5-methyl-7-octynyl, 6-methyl-7-octynyl, 1-propyl-5-hexynyl, 2-ethyl-6-heptynyl, 6,6-dimethyl-4-heptynyl, 9-decynyl, 1-methyl-8-nonynyl, 3-methyl-8-nonynyl, 8-methyl-6-nonynyl, 3-ethyl-7-octynyl, 3,7-dimethyl-4-octynyl, 7,7-dimethyl-5-octynyl, 10-undecynyl, 4,8-dimethyl-6-nonynyl, 11-dodecynyl, 12-tridecynyl, 13-tetradecynyl, 14-pentadecynyl, 3,7,11-trimethyl-9-dodecynyl, 15-hexadecynyl, 4,8,12-trimethyl-10-tridecynyl, 1-methyl-14-pentadecynyl, 14-methyl-12-pentadecynyl, 13,13-dimethyl-12-tetradecynyl, 16-heptadecynyl, 15-methyl-13-hexadecynyl, 17-octadecynyl, 1-methyl-16-heptadecynyl, 18-nonadecynyl, 19-eicosynyl or 3,7,11,15-tetramethyl-13-hexadecynyl group, preferably an alkynyl group having 2 to 10 carbon atoms, and more preferably an alkynyl group having 2 to 5 carbon atoms.

In the above, an "alkynyl group having 3 to 20 carbon atoms interposed with a hetero atom" in the definition of $R^7$ indicates a group in which an "alkynyl group having 3 to 20 carbon atoms" of the aforementioned "alkynyl groups having 2 to 20 carbon atoms" may be the same or different, and is interposed with 1 or 2 sulfur atoms, oxygen atoms or nitrogen atoms, examples of which include an alkynyl group having 3 to 20 carbon atoms interposed with 1 or 2 sulfur atoms such as 2-methylthioethynyl, 1-methylthio-2-propynyl, 3-methylthio-1-propynyl, 1-methylthio-3-butynyl, 2-methylthio-3-butynyl, 1-ethylthio-2-propynyl, 3-methyl-3-methylthio-1-propynyl, 4-methylthio-2-pentynyl, 3-methylthio-4-pentynyl, 2-methylthio-3-pentynyl, 1-methylthio-3-pentynyl, 3,3-dimethylthio-1-butynyl, 2,2-dimethylthio-3-butynyl, 1,1-dimethylthio-3-butynyl, 1-methyl-2-methylthio-3-butynyl, 2-ethylthio-3-butynyl, 1-methylthio-5-hexynyl, 2-methylthio-5-hexynyl, 3-methylthio-5-hexynyl, 4-methylthio-5-hexynyl, 5-methylthio-3-hexynyl, 1-propylthio-2-butynyl, 4-methyl-4-methylthio-2-pentynyl, 1-methylthio-6-heptynyl, 2-methylthio-6-heptynyl, 3-methylthio-6-heptynyl, 4-methylthio-6-heptynyl, 5-methylthio-6-heptynyl, 6-methylthio-4-heptynyl, 1-propylthio-4-pentynyl, 2-ethylthio-5-hexynyl, 5-methyl-5-methylthio-3-hexynyl, 3-methylthio-7-octynyl, 4-methylthio-7-octynyl, 5-methylthio-7-octynyl, 6-methylthio-7-octynyl, 1-propylthio-5-hexynyl, 2-ethylthio-6-heptynyl, 6-methyl-6-methylthio-4-heptynyl, 1-methylthio-8-nonynyl, 3-methylthio-8-nonynyl, 8-methylthio-6-nonynyl, 3-ethylthio-7-octynyl, 3-methyl-7-methylthio-4-octynyl, 7,7-dimethylthio-5-octynyl, 4-methyl-8-methylthio-6-nonynyl, 3,7-dimethyl-11-methylthio-9-dodecynyl, 4,8-dimethyl-12-methylthio-10-tridecynyl, 1-methylthio-14-pentadecynyl, 14-methylthio-12-pentadecynyl, 13-methyl-13-methylthio-11-tetradecynyl, 15-methylthio-13-hexadecynyl, 1-methylthio-16-heptadecynyl or 3,7,11-trimethyl-15-methylthio-13-hexadecynyl;

an alkynyl group having 3 to 20 carbon atoms interposed with 1 or 2 oxygen atoms such as 2-methyloxyethynyl, 1-methyloxy-2-propynyl, 3-methyloxy-1-propynyl, 2-ethyloxyethynyl, 1-methyloxy-3-butynyl, 2-methyloxy-3-butynyl, 1-ethyloxy-2-propynyl, 3-methyl-3-methyloxy-1-propynyl, 4-methyloxy-2-pentynyl, 3-methyloxy-4-pentynyl, 2-methyloxy-4-pentynyl, 1-methyloxy-4-pentynyl, 3,3-dimethyloxy-1-butynyl, 2,2-dimethyloxy-3-butynyl, 1,1-dimethyloxy-3-butynyl, 1-methyl-2-methyloxy-3-butynyl, 2-ethyloxy-3-butynyl, 1-methyloxy-5-hexynyl, 2-methyloxy-5-hexynyl, 3-methyloxy-5-hexynyl, 4-methyloxy-5-hexynyl, 5-methyloxy-3-hexynyl, 1-propyloxy-3-butynyl, 4-methyl-4-methyloxy-2-pentynyl, 1-methyloxy-6-heptynyl, 2-methyloxy-6-heptynyl, 3-methyloxy-6-heptynyl, 4-methyloxy-6-heptynyl, 5-methyloxy-6-heptynyl, 6-methyloxy-6-heptynyl, 1-propyloxy-6-pentynyl, 2-ethyloxy-5-hexynyl, 5-methyl-5-methyloxy-3-hexynyl, 3-methyloxy-7-octynyl, 4-methyloxy-7-octynyl, 5-methyloxy-7-octynyl, 6-methyloxy-7-octynyl, 1-propyloxy-5-hexynyl, 2-ethyloxy-6-heptynyl, 6-methyl-6-methyloxy-4-heptynyl, 1-methyloxy-8-nonynyl, 3-methyloxy-8-nonynyl, 8-methyloxy-6-nonynyl, 3-ethyloxy-7-octynyl, 3-methyl-7-methyloxy-6-octynyl, 7,7-dimethyloxy-5-octynyl, 4-methyl-8-methyloxy-6-nonynyl, 3,7-dimethyl-11-methyloxy-9-dodecynyl, 4,8-dimethyl-12-methyloxy-10-tridecynyl, 1-methyloxy-14-pentadecynyl, 14-methyloxy-12-pentadecynyl, 13-methyl-13-methyloxy-11-tetradecynyl, 15-methyloxy-13-hexadecynyl, 1-methyloxy-14-heptadecynyl or 3,7,11-trimethyl-15-methyloxy-13-hexadecynyl;

an alkynyl group having 3 to 20 carbon atoms interposed with 1 or 2 nitrogen atoms such as 2-(N-methylamino)ethynyl, 1-(N-methylamino)-2-propynyl, 3-(N-methylamino)-1-propynyl, 2-(N-ethylamino)ethynyl, 2-(N,N-dimethylamino)ethynyl, 1-(N-methylamino)-3-butynyl, 2-(N-methylamino)-3-butynyl, 3-(N-methylamino)-1-butynyl, 3-(N-ethylamino)-1-propynyl, 3-(N,N-dimethylamino)-1-propynyl, 4-(N-methylamino)-2-pentynyl, 3-(N-methylamino)-4-pentynyl, 2-(N-methylamino)-4-pentynyl, 1-(N-methylamino)-4-pentynyl, 3-(N,N-dimethylamino)-1-butynyl, 2-(N,N-dimethylamino)-3-butynyl, 1-(N,N-dimethylamino)-3-butynyl, 1-methyl-2-(N-methylamino)-3-butynyl, 2-(N-ethylamino)-3-butynyl, 1-(N-methylamino)-5-hexynyl, 2-(N-methylamino)-5-hexynyl, 3-(N-methylamino)-5-hexynyl, 4-(N-methylamino)-5-hexynyl, 5-(N-methylamino)-3-hexynyl, 1-(N-propylamino)-3-butynyl, 4-methyl-4-(N-methylamino)-2-pentynyl, 1-(N-methylamino)-6-heptynyl, 2-(N-methylamino)-6-heptynyl, 3-(N-methylamino)-6-heptynyl, 4-(N-methylamino)-6-heptynyl, 5-(N-methylamino)-6-heptynyl, 6-(N-methylamino)-6-heptynyl, 1-(N-propylamino)-4-pentynyl, 2-(N-ethylamino)-5-hexynyl, 5-methyl-5-(N-methylamino)-5-hexynyl, 3-(N-methylamino)-7-octynyl, 4-(N-methylamino)-7-octynyl, 5-(N-methylamino)-7-octynyl, 6-(N-methylamino)-7-octynyl, 1-(N-propylamino)-5-hexynyl, 2-(N-ethylamino)-6-heptynyl, 6-methyl-6-(N-methylamino)-6-heptynyl, 1-(N-methylamino)-8-nonynyl, 3-(N-methylamino)-8-nonynyl, 8-(N-methylamino)-6-nonynyl, 3-(N-ethylamino)-7-octynyl, 3-methyl-7-(N-methylamino)-5-octynyl, 7,7-di(N-methylamino)-5-octynyl, 4-methyl-8-(N-methylamino)-6-nonynyl, 3,7-dimethyl-11-(N-methylamino)-9-dodecynyl, 4,8.-dimethyl-12-(N-methylamino)-10-tridecynyl, 1-(N-methylamino)-14-pentadecynyl, 14-(N-methylamino)-14-pentadecynyl, 13-methyl-13-(N-methylamino)-11-tetradecynyl, 15-(N-methylamino)-13-hexadecynyl, 1-(N-methylamino)-16-heptadecynyl or 3,7,11-trimethyl-15-(N-methylamino)-15-hexadecynyl, preferably an alkynyl group having 3 to 10 carbon atoms interposed with a hetero atom, and more preferably an alkynyl group having 3 to 5 carbon atoms interposed with a hetero atom.

In the above, an "alkynyl group having 2 to 20 carbon atoms substituted with an aryl group or aromatic heterocyclic group" in the definition of $R^7$ indicates a group in which the aforementioned "alkynyl group having 2 to 20 carbon atoms" may be the same or different, and is substituted with 1 to 3 of the aforementioned "aryl groups". or the aforementioned "aromatic heterocyclic groups", and is preferably an alkynyl group having 2 to 5 carbon atoms substituted with an aryl group or aromatic heterocyclic group, examples of which include 2-phenylethynyl, 3-phenyl-1-propynyl, 1-phenyl-2-propynyl, 3-(4-methylphenyl)-1-propynyl, 4-phenyl-2-butynyl, 3-phenyl-1-butynyl, 4-(4-methylphenyl)-2-butynyl, 5-phenyl-3-pentynyl, 4-phenyl-2-pentynyl, and 3-phenyl-1-pentynyl.

In the above, an "alkenyl group having 2 to 20 carbon atoms" in the definition of $R^7$ is a linear or branched alkenyl group having 2 to 20 carbon atoms, examples of which include ethenyl, 2-propenyl, 1-methyl-2-propenyl, 2-methyl-2-propenyl, 2-ethyl-2-propenyl, 2-butenyl, 1-methyl-2-butenyl, 2-methyl-2-butenyl, 1-ethyl-2-butenyl, 3-butenyl, 1-methyl-3-butenyl, 2-methyl-3-butenyl, 1-ethyl-3-butenyl, 2-pentenyl, 1-methyl-2-pentenyl, 2-methyl-2-pentenyl, 3-pentenyl, 1-methyl-3-pentenyl, 2-methyl-3-pentenyl, 4-pentenyl, 1-methyl-4-pentenyl, 2-methyl-4-pentenyl, 2-hexenyl, 3-hexenyl, 4-hexenyl, 5-hexenyl, 6-heptenyl, 1-methyl-5-hexenyl, 2-methyl-5-hexenyl, 3-methyl-5-hexenyl, 4-methyl-5-hexenyl, 5-methyl-5-hexenyl, 1-propyl-3-butenyl, 4,4-dimethyl-2-pentenyl, 7-octenyl, 1-methyl-6-heptenyl, 2-methyl-6-heptenyl, 3-methyl-6-heptenyl, 4-methyl-6-heptenyl, 5-methyl-6-heptenyl, 6-methyl-6-heptenyl, 1-propyl-4-pentenyl, 2-ethyl-5-hexenyl, 5,5-dimethyl-3-hexenyl, 8-nonenyl, 3-methyl-7-octenyl, 4-methyl-7-octenyl, 5-methyl-7-octenyl, 6-methyl-7-octenyl, 1-propyl-5-hexenyl, 2-ethyl-6-heptenyl, 6,6-dimethyl-4-heptenyl, 9-decenyl, 1-methyl-B-nonenyl, 3-methyl-8-nonenyl, 8-methyl-8-nonenyl, 3-ethyl-7-octenyl, 3,7-dimethyl-7-octenyl, 7,7-dimethyl-7-octenyl, 10-undecenyl, 4,8-dimethyl-8-nonenyl, 9-dodecenyl, 12-tridecenyl, 13-tetradecenyl, 14-pentadecenyl, 3,7,11-trimethyl-11-dodecenyl, 15-hexadecenyl, 4,8,12-trimethyl-12-tridecenyl, 1-methyl-14-pentadecenyl, 14-methyl-14-pentadecenyl, 13,13-dimethyl-13-tetradecenyl, 16-heptadecenyl, 15-methyl-15-hexadecenyl, 17-octadecenyl, 1-methyl-16-heptadecenyl, 18-nonadecenyl, 19-eicosenyl or 3,7,11,15-tetramethyl-15-hexadecenyl group and preferably an alkenyl group having 2 to 10 carbon atoms.

In the above, an "alkenyl group having 3 to 20 carbon atoms interposed with a hetero atom" in the definition of $R^7$ indicates a group in which an "alkenyl group having 3 to 20 carbon atoms" of the aforementioned "alkenyl groups having 2 to 20 carbon atoms" may be the same or different, and is interposed with 1 or 2 sulfur atoms, oxygen atoms or nitrogen atoms, examples of which include an alkenyl group having 3 to 20 carbon atoms interposed with one or two sulfur atoms such as 1-methylthioethenyl, 2-methylthioethenyl, 1-methylthio-2-propenyl, 2-methylthio-2-propenyl, 3-methylthio-1-propenyl, 2-ethylthioethenyl, 2-methyl-2-methylthioethenyl, 1-methylthio-3-butenyl, 2-methylthio-3-butenyl, 3-methylthio-3-butenyl, 2-ethylthio-2-propenyl, 3-methyl-3-methylthio-1-propenyl, 4-methylthio-4-pentenyl, 3-methylthio-4-pentenyl, 2-methylthio-4-pentenyl, 1-methylthio-4-pentenyl, 3,3-dimethylthio-1-butenyl, 2,2-dimethylthio-3-butenyl, 1,1-dimethylthio-3-butenyl, 1-methyl-2-methylthio-3-butenyl, 1,3-dimethylthio-3-butenyl, 2,3-dimethylthio-3-butenyl, 2-ethylthio-3-butenyl, 1-methylthio-5-hexenyl, 2-methylthio-5-hexenyl, 3-methylthio-5-hexenyl, 4-methylthio-5-hexenyl, 5-methylthio-5-hexenyl, 1-propylthio-3-butenyl, 4-methyl-4-methylthio-4-pentenyl, 1-methylthio-6-heptenyl, 2-methylthio-6-heptenyl, 3-methylthio-6-heptenyl, 4-methylthio-6-heptenyl, 5-methylthio-6-heptenyl, 6-methylthio-6-heptenyl, 1-propylthio-4-pentenyl, 2-ethylthio-5-hexenyl, 5-methyl-5-methylthio-5-hexenyl, 3-methylthio-7-octenyl, 4-methylthio-7-octenyl, 5-methylthio-7-octenyl, 6-methylthio-7-octenyl, 1-propylthio-5-hexenyl, 2-ethylthio-6-heptenyl, 6-methyl-6-methylthio-6-heptenyl, 1-methylthio-8-nonenyl, 3-methylthio-8-nonenyl, 8-methylthio-8-nonenyl, 3-ethylthio-7-octenyl, 3-methyl-7-methylthio-7-octenyl, 7,7-dimethylthio-7-octenyl, 4-methyl-8-methylthio-8-nonenyl, 3,7-dimethyl-11-methylthio-11-dodecenyl, 4,8-dimethyl-12-methylthio-12-tridecenyl, 1-methylthio-14-pentadecenyl, 14-methylthio-14-pentadecenyl, 13-methyl-13-methylthio-13-tetradecenyl, 15-methylthio-15-hexadecenyl, 1-methylthio-16-heptadecenyl or 3,7,11-trimethyl-15-methylthio-15-hexadecenyl;

an alkenyl group having 3 to 20 carbon atoms interposed with 1 or 2 oxygen atoms such as;

1-methyloxyethenyl, 2-methyloxyethenyl, 1-methyloxy-2-propenyl, 2-methyloxy-2-propenyl, 3-methyloxy-2-propenyl, 2-ethyloxyethenyl, 2-methyl-2-methyloxyethenyl, 1-methyloxy-3-butenyl, 2-methyloxy-3-butenyl, 3-methyloxy-3-butenyl, 2-ethyloxy-2-propenyl, 3-methyl-3-methyloxy-2-propenyl, 4-methyloxy-4-pentenyl, 3-methyloxy-4-pentenyl, 2-methyloxy-4-pentenyl, 1-methyloxy-4-pentenyl, 3,3-dimethyloxy-3-butenyl, 2,2-dimethyloxy-3-butenyl, 1,1-dimethyloxy-3-butenyl, 1-methyl -2-methyloxy-3-butenyl, 1,3-dimethyloxy-3-butenyl, 2,3-dimethyloxy-3-butenyl, 2-ethyloxy-3-butenyl, 1-methyloxy-5-hexenyl, 2-methyloxy-5-hexenyl, 3-methyloxy-5-hexenyl, 4-methyloxy-5-hexenyl, 5-methyloxy-5-hexenyl, 1-propyloxy-3-butenyl, 4-methyl-4-methyloxy-4-pentenyl, 1-methyloxy-6-heptenyl, 2-methyloxy-6-heptenyl, 3-methyloxy-6-heptenyl, 4-methyloxy-6-heptenyl, 5-methyloxy-6-heptenyl, 6-methyloxy-6-heptenyl, 1-propyloxy-4-pentenyl, 2-ethyloxy-5-hexenyl, 5-methyl-5-methyloxy-5-hexenyl, 3-methyloxy-7-octenyl, 4-methyloxy-7-octenyl, 5-methyloxy-7-octenyl, 6-methyloxy-7-octenyl, 1-propyloxy-5-hexenyl, 2-ethyloxy-6-heptenyl, 6-methyl -6-methyloxy-6-heptenyl, 1-methyloxy-8-nonenyl, 3-methyloxy-8-nonenyl, 8-methyloxy-8-nonenyl, 3-ethyloxy-7-octenyl, 3-methyl -7-methyloxy-7-octenyl, 7,7-dimethyloxy-7-octenyl, 4-methyl-8-methyloxy-8-nonenyl, 3,7-dimethyl-11-methyloxy-11-dodecenyl, 4,8-dimethyl-12-methyloxy-12-tridecenyl, 1-methyloxy-14-pentadecenyl, 14-methyloxy-14-pentadecenyl, 13-methyl-13-methyloxy-11-tetradecenyl, 15-methyloxy-15-hexadecenyl, 1-methyloxy-16-heptadecenyl or 3,7,11-trimethyl-15-methyloxy-15-hexadecenyl;

an alkenyl group having 3 to 20 carbon atoms interposed with 1 or 2 nitrogen atoms such as;

1-(N-methylamino)ethenyl, 2-(N-methylamino)ethenyl, 1-(N -methylamino)-2-propenyl, 2-(N-methylamino)-2-propenyl, 3-(N -methylamino)-2-propenyl, 2-(N-ethylamino)ethenyl, 2-(N,N -dinethylamino)ethenyl, 1-(N-methylamino)-3-butenyl, 2-(N -methylamino)-3-butenyl, 3-(N-methylamino)-3-butenyl, 2-(N -ethylamino)-2-propenyl, 3-(N,N-dimethylamino)-2-propenyl, 4-(N-methylamino)-4-pentenyl, 3-(N-methylamino)-4-pentenyl, 2-(N -methylamino)-4-pentenyl, 1-(N-methylamino)-4-pentenyl, 3-(N,N -dimethylamino)-3-butenyl, 2-(N,N-dimethylamino)-3-butenyl, 1-(N,N-dimethylamino)-3-butenyl, 1-methyl-2-(N-methylamino)-3-butenyl, 1,3-di(N-methylamino)-3-butenyl, 2,3-di(N-methylamino) -3-butenyl, 2-(N-ethylamino)-3-butenyl, 1-(N-methylamino)-5-hexenyl, 2-(N-methylamino)-5-hexenyl, 3-(N-methylamino)-5-hexenyl, 4-(N-methylamino)-5- hexenyl, 5-(N-methylamino)-5-hexenyl, 1-(N-propylamino)-3-butenyl, 4-methyl-4-(N-methylamino)-4-pentenyl, 1-(N-methylamino)-6-heptenyl, 2-(N-methylamino)-6-heptenyl, 3-(N-methylamino)-6-heptenyl, 4-(N-methylamino)-6-heptenyl, 5-(N-methylamino)-6-heptenyl, 6-(N-methylamino)-6-heptenyl, 1-(N-propylamino)-4-pentenyl, 2-(N-ethylamino)-5-hexenyl, 5-methyl-5-(N-methylamino)-3-hexenyl, 3-(N-methylamino)-7-octenyl, 4-(N-methylamino)-7-octenyl, 5-(N-methylamino)-7-octenyl, 6-(N-methylamino)-7-octenyl, 1-(N-propylamino)-5-hexenyl, 2-(N-ethylamino)-6-heptenyl, 6-methyl-6-(N-methylamino)-6-heptenyl, 1-(N-methylamino)-8-nonenyl, 3-(N-methylamino)-8-nonenyl, 8-(N-methylamino)-8-nonenyl, 3-(N-ethylamino)-7-octenyl, 3-methyl-7-(N-methylamino)-7-octenyl, 7,7-di(N-methylamino)-5-octenyl, 4-methyl-8-(N-methylamino)-8-nonenyl, 3,7-dimethyl-11-(N-methylamino)-11-dodecenyl, 4,8-dimethyl-12-(N-methylamino)-12-tridecenyl, 1-(N-methylamino)-14-pentadecenyl, 14-(N-methylamino)-14-pentadecenyl, 13-methyl-13-(N-methylamino)-13-tetradecenyl, 15-(N-methylamino)-15-hexadecenyl, 1-(N-methylamino)-16-heptadecenyl or 3,7,11-trimethyl-15-(N-methylamino)-15-hexadecenyl and preferably an alkenyl group having 3 to 10 carbon atoms interposed with a hetero atom.

In the above, an "alkenyl group having 2 to 20 carbon atoms substituted with an aryl group or heterocyclic group" in the definition of R$^7$ is a group in which the aforementioned "alkenyl group having 2 to 20 carbon atoms" may be the same or different, and is substituted with 1 to 3 of the aforementioned "aryl groups" or the aforementioned "aromatic heterocyclic groups", examples of which include 2-phenylethenyl, 3-phenyl-1-propenyl, 1-phenyl-2-propenyl, 3-(4-methylphenyl)-1-propenyl, 4-phenyl-2-butenyl, 3-phenyl-1-butenyl, 4-(4-methylphenyl)-2-butenyl, 5-phenyl-3-pentenyl, 4-phenyl-2-pentenyl and 3-phenyl-1-pentenyl.

In the above, an "alkyl group having 1 to 20 carbon atoms substituted with an aryl group or aromatic heterocyclic group and interposed with a hetero atom" in the definition of R$^7$ indicates a group in which the aforementioned "alkyl group having 2 to 20 carbon atoms interposed with a hetero atom" may be the same or different, and is substituted with 1 or 3 of the aforementioned "aryl groups" or the aforementioned "aromatic heterocyclic groups", examples of which include an alkyl group having 2 to 20 carbon atoms interposed with 1 or sulfur atoms substituted with an aryl group such as 1-phenylthioethyl, 2-phenylthioethyl, 1-phenylthio-2-propyl, 2-phenylthio-2-propyl, 3-phenylthio-1-propyl, 2-(4-methylphenyl)thioethyl, 2-methyl-2-phenylthioethyl, 1-phenylthio-3-butyl, 2-phenylthio-3-butyl, 3-phenylthio-3-butyl, 2-(4-methylphenyl)thio-2-propyl, 3-methyl-3-phenylthio-1-propyl, 4-phenylthio-4-pentyl, 3-phenylthio-4-pentyl, 2-phenylthio-4-pentyl, 1-phenylthio-4-pentyl, 3,3-diphenylthio-1-butyl, 2,2-diphenylthio-3-butyl, 1,1-diphenylthio-3-butyl, 1-methyl-2-phenylthio-3-butyl, 1,3-diphenylthio-3-butyl, 2,3-diphenylthio-3-butyl, 2-(4-methylphenyl)thio-3-butyl, 1-phenylthio-5-hexyl, 2-phenylthio-5-hexyl, 3-phenylthio-5-hexyl, 4-phenylthio-5-hexyl, 5-phenylthio-5-hexyl, 1-(4-ethylphenyl)thio-3-butyl, 4-methyl-4-phenylthio-4-pentyl, 1-phenylthio-6-heptyl, 2-phenylthio-6-heptyl, 3-phenylthio-6-heptyl, 4-phenylthio-6-heptyl, 5-phenylthio-6-heptyl, 6-phenylthio-6-heptyl, 1-(4-ethylphenyl)thio-4-pentyl, 2-(4-methylphenyl)thio-5-hexyl, 5-methyl-5-phenylthio-5-hexyl, 3-phenylthio-7-octyl, 4-phenylthio-7-octyl, 5-phenylthio-7-octyl, 6-phenylthio-7-octyl, 1-(4-ethylphenyl)thio-5-hexyl, 2-(4-methylphenyl)thio-6-heptyl, 6-methyl-6-phenylthio-6-heptyl, 1-phenylthio-8-nonyl, 3-phenylthio-8-nonyl, 8-phenylthio-8-nonyl, 3-(4-methylphenyl)thio-7-octyl, 3-methyl-7-phenylthio-7-octyl, 7,7-diphenylthio-7-octyl, 4-methyl-8-phenylthio-8-nonyl, 3,7-dimethyl-11-phenylthio.-11-dodecyl, 4,8-dimethyl-12-phenylthio-12-tridecyl, 1-phenylthio-14-pentadecyl, 14-phenylthio-14-pentadecyl, 13-methyl-13-phenylthio-13-tetradecyl, 15-phenylthio-15-hexadecyl, 1-phenylthio-16-heptadecyl or 3,7,11-trimethyl-15-phenylthio-15-hexadecyl;

an alkyl group having 2 to 20 carbon atoms interposed with 1 or 2 oxygen atoms substituted with an aryl group such as 1-phenyloxyethyl, 2-phenyloxyethyl, 1-phenyloxy-2-propyl, 2-phenyloxy-2-propyl, 3-phenyloxy-2-propyl, 2-ethyloxyethyl, 2-methyl-2-phenyloxyethyl, 1-phenyloxy-3-butyl, 2-phenyloxy-3-butyl, 3-phenyloxy-3-butyl, 2-ethyloxy-2-propyl, 3-methyl-3-phenyloxy-2-propyl, 4-phenyloxy-4-pentyl, 3-phenyloxy-4-pentyl, 2-phenyloxy-4-pentyl, 1-phenyloxy-4-pentyl, 3,3-diphenyloxy-3-butyl, 2,2-diphenyloxy-3-butyl, 1,1-diphenyloxy-3-butyl, 1-methyl-2-phenyloxy-3-butyl, 1,3-diphenyloxy-3-butyl, 2,3-diphenyloxy-3-butyl, 2-(4-methylphenyl)oxy-3-butyl, 1-phenyloxy-5-hexyl, 2-phenyloxy-5-hexyl, 3-phenyloxy-5-hexyl, 4-phenyloxy-5-hexyl, 5-phenyloxy-5-hexyl, 1-(4-ethylphenyl)oxy-3-butyl, 4-methyl-4-phenyloxy-4-pentyl, 1-phenyloxy-6-heptyl, 2-phenyloxy-6-heptyl, 3-phenyloxy-6-heptyl, 4-phenyloxy-6-heptyl, 5-phenyloxy-6-heptyl, 6-phenyloxy-6-heptyl., 1-(4-ethylphenyl)oxy-4-pentyl, 2-(4-methylphenyl)oxy-5-hexyl, 5-methyl-5-phenyloxy-5-hexyl, 3-phenyloxy-7-octyl, 4-phenyloxy-7-octyl, 5-phenyloxy-7-octyl, 6-phenyloxy-7-octyl, 1-(4-ethylphenyl)oxy-5-hexyl, 2-(4-methylphenyl)oxy-6-heptyl, 6-methyl-6-phenyloxy-6-heptyl, 1-phenyloxy-8-nonyl, 3-phenyloxy-8-nonyl, 8-phenyloxy-8-nonyl, 3-(4-methylphenyl)oxy-7-octyl, 3-methyl-7-phenyloxy-7-octyl, 7,7-diphenyloxy-7-octyl, 4-methyl-8-phenyloxy-8-nonyl, 3,7-dimethyl-11-phenyloxy-11-dodecyl, 4,8-dimethyl-12-phenyloxy-12-tridecyl, 1-phenyloxy-14-pentadecyl, 14-phenyloxy-14-pentadecyl, 13-methyl-13-phenyloxy-11-tetradecyl, 15-phenyloxy-15-hexadecyl, 1-phenyloxy-16-heptadecyl or 3,7,11-trimethyl-15-phenyloxy-15-hexadecyl; and an alkyl group having 2 to 20 carbon atoms interposed with 1 or 2 nitrogen atoms substituted with an aryl group such as 1-(N-phenylamino)ethyl, 2-(N-phenylamino)ethyl, 1-(N-phenylamino)-2-propyl, 2-(N-phenylamino)-2-propyl, 3-(N-phenylamino)-2-propyl, 2-[N-(4-methylphenyl)amino]ethyl, 2-(N,N-diphenylamino)ethyl, 1-(N-phenylamino)-3-butyl, 2-(N-phenylamino)-3-butyl, 3-(N-phenylamino)-3-butyl, 2-[N-(4-methylphenyl)-amino]-2-propyl, 3-(N,N-diphenylamino)-2-propyl, 4-(N-phenylamino)-4-pentyl, 3-(N-phenylamino)-4-pentyl, 2-(N-phenylamino)-4-pentyl, 1-(N-phenylamino)-4-pentyl, 3-(N,N-diphenylamino)-3-butyl, 2-(N,N-diphenylamino)-3-butyl, 1-(N,N-diphenylamino)-3-butyl, 1-methyl-2-(N-phenylamino)-3-butyl, 1,3-di(N-phenylamino)-3-butyl, 2,3-di(N-phenylamino)-3-butyl, 2-[N-(4-methylphenyl)amino]-3-butyl, 1-(N-phenylamino)-5-hexyl, 2-(N-phenylamino)-5-hexyl, 3-(N-phenylamino)-5-hexyl, 4-(N-phenylamino)-5-hexyl, 5-(N-phenylamino)-5-hexyl, 1-[N-(4-ethylphenyl)amino]-3-butyl, 4-methyl-4-(N-phenylamino)-4-pentyl, 1-(N-phenylamino)-6-heptyl, 2-(N-phenylamino)-6-heptyl, 3-(N-phenylamino)-6-heptyl, 4-(N-phenylamino)-6-heptyl, 5-(N-phenylamino)-6-heptyl, 6-(N-phenylamino)-6-heptyl, 1-[N-(4-ethylphenyl)amino]-4-pentyl, 2-[N-(4-methylphenyl)amino]-5-hexyl, 5-methyl-5-(N-phenylamino)-3-hexyl, 3-(N-phenylamino)-7-octyl, 4-(N- phenylamino)-7-octyl, 5-(N-phenylamino)-7-octyl, 6-(N-phenylamino)-7-octyl, 1-[N-(4-ethylphenyl)amino]-5-hexyl, 2-[N-(4-methylphenyl)amino]-6-heptyl, 6-methyl-6-(N-phenylamino)-6-heptyl, 1-(N-phenylamino) -8-nonyl, 3-(N-phenylamino)-8-nonyl, 8-(N-phenylamino)-8-nonyl, 3-[N-(4-methylphenyl)amino]-7-octyl, 3-methyl-7-(N-phenylamino) -7-octyl, 7,7-di(N-phenylamino)-5-octyl, 4-methyl-8-(N -phenylamino)-8-nonyl, 3,7-dimethyl-1-(N-phenylamino)-11-dodecyl, 4,8-dimethyl-12-(N-phenylamino)-12-tridecyl, 1-(N -phenylamino)-14-pentadecyl, 14-(N-phenylamino)-14-pentadecyl, 13-methyl-13-(N-phenylamino)-13-tetradecyl, 15-(N-phenylamino) -15-hexadecyl, 1-(N-phenylamino)-16-heptadecyl or 3,7,11-trimethyl-15-(N-phenylamino)-15-hexadecyl.

In the above, a "cycloalkyl group having 2 to 20 carbon atoms" in the definition of $R^7$ is a lower cycloalkyl group, examples of which include the aforementioned "cycloalkyl group", cyclopropyl, cyclobutyl, cyclopentyl or cyclohexyl group, and preferably a cyclopropyl group.

Step C1:

In Step C1, a compound having general formula (X) is produced, and this is carried out by selectively acylating only one of the hydroxyl groups of a compound having general formula (VIII) using a compound having general formula (IX) in the presence or absence or an inert solvent and in the presence of lipase.

There are no particular limitations on the lipase used in the aforementioned reaction, and although the optimum lipase varies depending on the type of raw material compound, it is preferably a lipase originating in *Pseudomonas* sp., *Pseudomonas fluorescens*, *Pseudomonas cepacia*, *Chromobacterium viscosum*, *Aspergillus niger*, *Aspergillus oryzae*, *Candida antarctica*, *Candida cylindracea*, *Candida lipolytica*, *Candida rugosa*, *Candida utilis*, *Penicillium roqueforti*, *Rhizopus arrhizus*, *Rhizopus delemar*, *Rhizopus javanicus*, *Rhizomucor miehei*, *Rhizopus niveus*, *Humicola lanuginosa*, *Mucor javanicus*, *Mucor miehei*, *Thermus aquaticus*, *Thermus flavus*, *Thermus thermophilus*, etc. or human pancreas, hog pancreas, porcine pancreas and wheat germ, and more preferably one which is immobilized from *Pseudomonas* sp., an example of which is immobilized lipase from *Pseudomonas* sp. (Toyobo). In addition to the enzyme being able to be used either partially or completely purified, it can also be used in the immobilized form.

While the optimum compound varies depending on the type of raw material compound, examples of compounds having general formula (IX) used in the aforementioned reaction preferably include vinyl esters of linear aliphatic carboxylic acids such as n-hexanoic acid vinyl ester, n-heptanoic acid vinyl ester, n-pentanoic acid vinyl ester and acetic acid vinyl ester, and more preferably, n-hexanoic acid vinyl ester.

Although there are no particular limitations on the inert solvent used in the aforementioned reaction, a compound having general formula (IX) may be used alone, or, although the optimum inert solvent varies depending on the type of raw material compound, various types of organic solvents and water-containing organic solvents can be used, preferred examples of which include ethers such as diisopropyl ether, t-butyl methyl ether, diethyl ether or tetrahydrofuran; aliphatic hydrocarbons such as n-hexane or n-heptane; aromatic hydrocarbons such as benzene or toluene; or halogenated hydrocarbons such as dichloromethane or 1,2-dichloroethane, more preferably ethers, and particularly preferably diisopropyl ether or t-butyl methyl ether.

Although varying depending on the raw material compound, solvent used and type of lipase used and so forth, the reaction temperature is normally from −50 to 50° C., and preferably from 0 to 40° C.

Although varying depending on the raw material compound, solvent used, type of lipase used, reaction temperature and so forth, the reaction time is normally from 15 minutes to 150 hours, and preferably from 30 minutes to 24 hours.

Step C2:

In Step C2, a compound having general formula (XI) is produced, and this is carried out by oxidizing a compound having general formula (X) in an inert solvent in the presence of an oxidizing agent.

There are no particular limitations on the oxidation reaction in the aforementioned reaction provided it is an oxidation reaction in which an aldehyde is formed from a primary alcohol, and examples of oxidation reactions include Collins oxidation which is carried out in dichloromethane using pyridine and chromic acid; PCC oxidation which is carried out in dichloromethane using pyridinium chlorochromate (PCC); PDC oxidation which is carried out in dichloromethane using pyridinium dichromate (PDC); DMSO oxidation such as Swern oxidation which is carried out in dichloromethane using an electrophilic agent (such as acetic anhydride, trifluorobutyric anhydride, thionyl chloride, sulfuryl chloride, oxalyl chloride, dicyclohexyl carbodiimide, diphenylketene-p-tolylimine, N,N-diethylaminoacetylene or sulfur trioxide-pyridine complex) and dimethyl sulfoxide (DMSO); or manganese dioxide oxidation which is carried out in dichloromethane or benzene using manganese dioxide, and preferably PCC oxidation, PDC oxidation or Swern oxidation.

Although varying depending on the raw material compound, solvent, type of oxidizing agent and so forth, the reaction temperature is normally from −78 to 80° C., and preferably from −78 to 30° C.

Although varying depending on the raw material compound, solvent, type of oxidizing agent, reaction temperature and so forth, the reaction time is normally from 10 minutes to 48 hours, and preferably from 30 minutes to 24 hours.

Step C3:

In Step C3, a compound having general formula (XIII) is produced, and this is carried out by reacting a compound having general formula (XI) with a compound having general formula (XII) in an inert solvent in the presence of a base.

Examples of the inert solvent used in the aforementioned reaction include ethers such as diethyl ether, diisopropyl ether, tetrahydrofuran,. dioxane, dimethoxyethane or diethylene glycol dimethyl ether; aromatic hydrocarbons such as toluene, benzene or xylene; halogenated hydrocarbons such as dichloromethane, chloroform, carbon tetrachloride, dichloroethane, chlorobenzene or dichlorobenzene; and amides such as formamide, N,N-dimethylformamide, N,N-dimethylacetamide or hexamethyl phosphoric triamide, preferably ethers, and more preferably tetrahydrofuran.

There are no particular limitations on the base used in the aforementioned reaction, and examples include alkyl lithiums such as methyl lithium, ethyl lithium, propyl lithium or butyl lithium; alkaline metal carbonates such as lithium carbonate, sodium carbonate or potassium carbonate; alkaline metal bicarbonates such as lithium bicarbonate, sodium bicarbonate or potassium bicarbonate; alkaline metal hydrides such as lithium hydride, sodium hydride or potassium hydride; alkaline metal hydroxides such as lithium hydroxide, sodium hydroxide or potassium hydroxide; and, alkaline metal alkoxides such as lithium methoxide, sodium methoxide, sodium ethoxide or potassium t-butoxide, preferably alkaline metal hydroxides; and organic amines such as trimethyl amine, tributyl amine, diisopropyl ethyl amine, N-methyl morpholine, pyridine, 4-(N,N-dimethylamino)pyridine, N,N-dimethylaniline, N,N-diethylaniline, 1,5-diazabicyclo[4.3.0]nona-5-ene, 1,4-diazabicyclo[2.2.2]octane (DABCO) or 1,8-diazabicyclo[5.4.0]-7-undecene (DBU), preferably alkaline metal alkoxides, and more preferably potassium t-butoxide.

Although varying depending on the raw material compound, solvent, type of base and so forth, the reaction temperature is normally from −78 to 200° C., preferably from −50 to 150° C., and more preferably 0° C.

Although varying depending on the raw material compound, solvent, base, reaction temperature and so forth, the reaction time is normally from 15 minutes to 48 hours, and preferably from 30 minutes to 8 hours.

Step C4:

In Step C4, a compound having general formula (XIV) is produced, and this is carried out by hydrolyzing a compound having general formula (XIII) in an inert solvent in the presence of a base.

There are no particular limitations on the inert solvent used in the aforementioned reaction, and examples include ethers such as diethyl ether, diisopropyl ether, tetrahydrofuran, dioxane, dimethoxyethane or diethylene glycol dimethyl ether; alcohols such as methanol, ethanol, n-propanol, isopropanol, n-butanol, isobutanol, t-butanol, isoamyl alcohol, diethylene glycol, glycerin, octanol, cyclohexanol or methyl cellosolve; amides such as formamide, N,N-dimethylformamide, N,N-dimethylacetamide or hexamethyl phosphoric triamide; water; or mixed solvents of the aforementioned solvents or mixed solvents of the aforementioned solvents and water, preferably mixed solvents of alcohols, ethers and water or mixed solvents of alcohols and water, and more preferably a mixed solvent of methanol, tetrahydrofuran and water or a mixed solvent of methanol and water.

There are no particular limitations on the base used in the aforementioned reaction provided it only acts in the desired hydrolysis reaction, and examples include those similar to the bases used in the aforementioned Step A3 of Process A, preferably-alkaline metal hydroxides, and more preferably sodium hydroxide.

Although varying depending on the raw material compound, solvent, type of base and so forth, the reaction temperature is normally from −78 to 150° C., preferably from −50 to 100° C. and more preferably in the vicinity of room temperature.

Although varying depending on the raw material compound, solvent, base, reaction temperature and so forth, the reaction time is normally from 15 minutes to 48 hours, and preferably from 30 minutes to 6 hours.

Step C5:

In Step C5, a compound having general formula (XV) is produced, and this is carried out by reacting a compound having general formula (XIV) with base in an inert solvent.

There are no particular limitations on the inert solvent used in the aforementioned reaction, and examples include ethers such as diethyl ether, diisopropyl ether, tetrahydrofuran, dioxane, dimethoxyethane and diethylene glycol dimethyl ether; alcohols such as methanol, ethanol, n-propanol, isopropanol, n-butanol, isobutanol, t-butanol, isoamyl alcohol, diethylene glycol, glycerin, octanol, cyclohexanol and methyl cellosolve; amides such as formamide, N,N-dimethylformamide, N,N-dimethylacetamide and hexamethyl phosphoric triamide; water; or mixed solvents of the aforementioned solvents or mixed solvents of the aforementioned solvents and water, preferably ethers or amides, and more preferably tetrahydrofuran.

There are no particular limitations on the base used in the aforementioned reaction provided it is used as a base in ordinary reactions, and examples include those similar to the bases used in the aforementioned Step A3 of Process A, preferably alkaline metal hydroxides, and more preferably potassium t-butoxide.

Although varying depending on the raw material compound, solvent, type of base and so forth, the reaction temperature is normally from −78 to 150° C., preferably from −50 to 100° C. and more preferably 0° C. to room temperature.

Although varying depending on the raw material compound, solvent, base, reaction temperature and so forth, the reaction time is normally from 15 minutes to 48 hours, and preferably from 30 minutes to 8 hours.

Step C5 can also be carried out by de-protecting the amino group of a compound having general formula (XIV), and then reacting with an acylating agent such as N,N-carbonyl diimidazole, dimethyl carbonate or diethyl carbonate.

Step C6:

In Step C6, a compound having general formula (II) is produced, and this is carried out by reducing a compound having general formula (XV) in an inert solvent in the presence of a reducing agent, and preferably, by catalytic reduction in a hydrogen atmosphere.

There are no particular limitations on the inert solvent used in the aforementioned reaction, and examples include aliphatic hydrocarbons such as hexane, heptane, ligroin or petroleum ether; aromatic hydrocarbons such as toluene, benzene or xylene; halogenated hydrocarbons such as dichloromethane, chloroform, carbon tetrachloride, dichloroethane, chlorobenzene or dichlorobenzene; esters such as methyl acetate, ethyl acetate, propyl acetate, butyl acetate or diethyl acetate; ethers such as diethyl ether, dioxane, tetrahydrofuran, dimethoxyethane or diethylene glycol dimethyl ether; amides such as formamide, N,N-dimethylformamide, N,N-dimethylacetamide or hexamethylphosphoric triamide; alcohols such as methanol, ethanol, n-propanol, isopropanol, n-butanol, isobutanol, t-butanol, isoamyl alcohol, diethylene glycol, glycerin, octanol, cyclohexanol or methyl cellosolve; organic acids such as formic acid or acetic acid; aqueous inorganic acid solutions such as aqueous hydrochloric acid or aqueous sulfuric acid; or water or mixed solvents of the aforementioned solvents and water. These examples preferably include alcohols or ethers, and more preferably methanol.

There are no particular limitations on the reducing agent used in the aforementioned reaction provided it is used in ordinary catalytic reduction reactions, and examples include palladium black, palladium-carbon, Raney nickel, platinum oxide, platinum black, rhodium-aluminium oxide, triphenyl phosphine-rhodium chloride or palladium-barium sulfate, preferably palladium-carbon or triphenyl phosphine-rhodium chloride, and more preferably 10% palladium carbon.

Although there are no particular limitations on the hydrogen pressure, it is normally 1 to 10 atmospheres and preferably 1 atmosphere.

Although the reaction temperature varies depending on the type of raw material compound, solvent, type of reducing agent and so forth, it is normally from −20 to 200° C., preferably from 0 to 100° C., and more preferably from 20 to 30° C.

Although the reaction time varies mainly depending on the reaction temperature as well as the raw material compound, reaction reagents, type of solvent used and so forth, it is normally from 5 minutes to 96 hours, preferably 15 minutes to 24 hours, and more preferably from 30 minutes to 2 hours.

Step C7:

In Step C7, a compound having general formula (XVI) is produced, and this is carried out by hydrolyzing a compound having general formula (II) in an inert solvent in the presence of a base.

There are no particular limitations on the inert solvent used in the aforementioned reaction, and examples include the same solvents as used in the previously described Step A3, preferably mixed solvents of alcohol and ether or mixed solvents of alcohol and water, and more preferably a mixed solvent of methanol and tetrahydrofuran or a mixed solvent of methanol and water.

There are no particular limitations on the base used in the aforementioned reaction provided it only acts in the desired hydrolysis reaction, and examples include the same bases used in the previously described Step A3 of Process A, preferably alkaline metal hydroxides, and more preferably potassium hydroxide or sodium hydroxide.

Although the reaction temperature varies depending on the type of raw material compound, solvent, type of base and so forth, it is normally from −78 to 200° C., preferably from 0 to 180° C., and more preferably from 20 to 120° C.

Although the reaction time varies depending on the raw material compound, base, solvent, reaction temperature and so forth, it is preferably from 15 minutes to 10 days, and more preferably from 2 hours to 5 days.

Step C8:

In Step C8, a compound having general formula (III) is produced, and this is carried out by protecting a hydroxyl group and an amino group of a compound having general formula (XVI) in an inert solvent.

Protection of the hydroxyl group and amino group can typically be carried out according to a commonly known method in the art of organic synthesis chemistry, such as Protective Groups in Organic Synthesis (Third Edition, 1999, John Wiley & Sons, Inc.).

An example of a method for protecting the amino group consists of reacting a compound having general formula (XVI) with the following compound:

$R^4$-Q or $R^5$-Q (wherein $R^4$, $R^5$ and Q are the same as previously defined) in an inert solvent (preferably an ether such as diethyl ether, diisopropyl ether, tetrahydrofuran, dioxane, dimethoxyethane or diethylene glycol dimethyl ether; or an alcohol such as methanol, ethanol, n-propanol, isopropanol, n-butanol, isobutanol, t-butanol, isoamyl alcohol, diethylene glycol, glycerin, octanol, cyclohexanol or methyl cellosolve), in the presence or absence of a base (preferably an organic amine such as trimethyl amine, tributyl amine, diisopropyl ethyl amine, N-methyl morpholine or pyridine), and at a reaction temperature of −78 to 150° C., preferably −50 to 100° C. and particularly preferably in the vicinity of room temperature, for 15 minutes to 48 hours and preferably for 30 minutes.

An example of a method for protecting the hydroxyl group includes reacting compound (XVI) with the following compound:

$R^6$-Q (wherein $R^6$ and Q are the same as previously defined) in an inert solvent (preferably a halogenated hydrocarbon such as chloroform, dichloromethane, 1,2-dichloroethane or carbon tetrachloride; an amide such as formamide, dimethylformamide, dimethylacetamide or hexamethyl phosphoric triamide; or a sulfoxide such as dimethyl sulfoxide), in the presence of a base (preferably an alkaline metal hydroxide such as lithium hydroxide, sodium hydroxide or potassium hydroxide; or an organic amine such as trimethyl amine, tributyl amine, diisopropyl ethyl amine, N-methyl morpholine or pyridine), and at a reaction temperature of −78 to 150° C., preferably −50 to 100° C. and most preferably in the vicinity of room temperature, for 15 minutes to 48 hours and preferably for 30 minutes.

Amino group protection and hydroxyl group protection can be carried out in any order, and the desired reactions can be carried out sequentially.

The desired compounds of each step of Process C are recovered from the reaction mixture in accordance with ordinary methods. For example, in the case of suitably neutralizing the reaction mixture or when impurities are present, an organic solvent such as ethyl acetate that is not miscible with water is added after removing the impurities by filtration, and after washing with water and so forth, the organic layer containing the desired compound is separated, and after drying with anhydrous magnesium sulfate or anhydrous sodium sulfate, the desired compound is obtained by distilling off the solvent. The resulting desired compound can be separated and purified as necessary by suitably combining ordinary methods, such as recrystallization, reprecipitation or other method commonly used for separation and purification of organic compounds, examples of which include absorption column chromatography using a carrier such as silica gel, alumina or magnesium-silica gel-based Florisil; a method using a synthetic adsorbent such as partition column chromatography using a carrier such as Sephadex LH-20 (Pharmacia), Amberlite XAD-11 (Rohm and Haas) or Diaion HP-20 (Mitsubishi Chemical), a method using ion exchange chromatography, and a forward-phase, reverse-phase column chromatography method using silica gel or alkylated silica gel (and preferably high-performance liquid column chromatography), and eluting with a suitable eluent.

Furthermore, when it is necessary to separate isomers, isomers can be separated by the aforementioned separation and purification means at a suitable time either following completion of the reaction of each step or following completion of a desired step.

Raw materials in the form of the compounds having general formula (VIII) and general formula (IX) are either known or can be easily produced by a known method or method similar thereto.

Process D is a process for producing a compound having general formula (XII), and can be carried out in accordance with a method described in the literature (J. Org. Chem., 52, 19 (1987)).

[Chemical Formula 14]

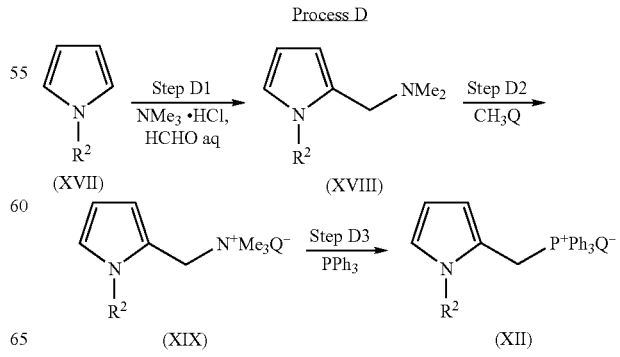

In the above formulae, $R^2$ and Q are the same as previously defined.

Step D1:

In Step D1, a compound having general formula (XVIII) is produced, and this is carried out by reacting a compound having general formula (XVII) with formalin and dimethylamine hydrochloride in accordance with a known method (such as the method described in J. Am. Chem. Soc., 73, 4921 (1951)).

Step D2:

In Step D2, a compound having general formula (XIX) is produced, and this is carried out by reacting a compound having general formula (XVIII) with a methyl halide such as methyl iodide to obtain a quaternary salt.

There are no particular limitations on the inert solvent used in the aforementioned reaction, and examples include aliphatic hydrocarbons such as hexane, heptane, ligroin or petroleum ether; aromatic hydrocarbons such as toluene, benzene or xylene; halogenated hydrocarbons such as dichloromethane, chloroform, carbon tetrachloride, dichloroethane, chlorobenzene or dichlorobenzene; ethers such as diethyl ether, diisopropyl ether, tetrahydrofuran, dioxane, dimethoxyethane or diethylene glycol dimethyl ether; lower alkyl nitriles such as acetonitrile or propionitrile; lower alkyl alcohols such as methanol, ethanol, propanol or butanol; or lower alkyl ketones such as acetone or methyl ethyl ketone, and preferably alcohols.

Although the reaction temperature varies depending on the raw material compound, type of solvent and so forth, it is normally from −10 to 200° C. and preferably from 0 to 50° C.

Although the reaction time mainly varies depending on the reaction temperature as well as raw material compound and type of solvent used, it is normally from 5 minutes to 96 hours, preferably from 15 minutes to 48 hours, and more preferably from 1 to 8 hours.

Step D3:

In Step D3, a compound having general formula (XII) is produced, and this is carried out by reacting a compound having general formula (XIX) with triphenyl phosphine in an inert solvent.

There are no particular limitations on the inert solvent used in the aforementioned reaction, and examples include aliphatic hydrocarbons such as hexane, heptane, ligroin or petroleum ether; aromatic hydrocarbons such as toluene, benzene or xylene; halogenated hydrocarbons such as dichloromethane, chloroform, carbon tetrachloride, dichloroethane, chlorobenzene or dichlorobenzene; ethers such as diethyl ether, diisopropyl ether, tetrahydrofuran, dioxane, dimethoxyethane or diethylene glycol dimethyl ether; lower alkyl nitriles such as acetonitrile or propionitrile; lower alkyl alcohols such as methanol, ethanol, propanol or butanol; or lower alkyl ketones such as acetone or methyl ethyl ketone, preferably ethers or nitriles, and more preferably acetonitrile.

Although the reaction temperature varies depending on the raw material compound, type of solvent and so forth, it is normally from 0 to 200° C., preferably from room temperature to 150° C., and more preferably from 20 to 100° C.

Although the reaction time mainly varies depending on the reaction temperature as well as raw material compound and type of solvent used, it is normally from 5 minutes to 96 hours, preferably from 15 minutes to 48 hours, and more preferably from 1 to 8 hours.

The desired compounds of each step of Process D are recovered from the reaction mixture in accordance with ordinary methods. For example, in the case of suitably neutralizing the reaction mixture or when impurities are present, an organic solvent such as ethyl acetate that is not miscible with water is added after removing the impurities by filtration, and after washing with water and so forth, the organic layer containing the desired compound is separated, and after drying with anhydrous magnesium sulfate or anhydrous sodium sulfate, the desired compound is obtained by distilling off the solvent. The resulting desired compound can be separated and purified as necessary by suitably combining ordinary methods, such as recrystallization, reprecipitation or other method commonly used for separation and purification of organic compounds, examples of which include absorption column chromatography using a carrier such as silica gel, alumina or magnesium-silica gel-based Florisil; a method using a synthetic adsorbent such as partition column chromatography using a carrier such as Sephadex LH-20 (Pharmacia), Amberlite XAD-11 (Rohm and Haas) or Diaion HP-20 (Mitsubishi Chemical), a method using ion exchange chromatography, and a forward-phase, reverse-phase column chromatography method using silica gel or alkylated silica gel (and preferably high-performance liquid column chromatography), and eluting with a suitable eluent.

Furthermore, when it is necessary to separate isomers, isomers can be separated by the aforementioned separation and purification means at a suitable time either following completion of the reaction of each step or following completion of a desired step.

A raw material in the form of the compound having general formula (XVII) is either known or can be easily produced by a known method or method similar thereto.

Process E is a process for increasing the optical purity of a compound having general formula (XVI).

[Chemical Formula 15]

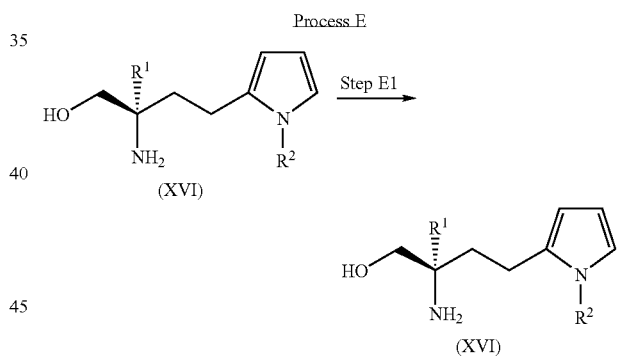

In the above formulae, $R^1$ and $R^2$ are the same as previously defined.

Step E1:

In Step E1, the optical purity of a compound having general formula (XVI) is increased, and this is carried out by treating a compound having general formula (XVI) with an optically active organic acid in an inert solvent to form a salt followed by increasing the optical purity by recrystallizing as necessary, and treating with base to obtain a compound having general formula (XVI).

There are no particular limitations on the inert solvent used in the aforementioned reaction provided it dissolves the raw material, and examples include aromatic hydrocarbons such as toluene, benzene or xylene; halogenated hydrocarbons such as dichloromethane, chloroform, carbon tetrachloride, dichloroethane, chlorobenzene or dichlorobenzene; esters such as methyl acetate, ethyl acetate, propyl acetate, butyl acetate or diethyl acetate; ethers such as diethyl ether, diisopropyl ether, tetrahydrofuran, dioxane, dimethoxyethane or diethylene glycol dimethyl ether; alcohols such as methanol, ethanol, n-propanol, isopropanol, n-butanol, isobutanol, t-butanol, isoamyl alcohol, diethylene glycol, glycerin, octanol, cyclohexanol or methyl cellosolve; nitriles such as acetonitrile or propionitrile; water or mixed solvents of the aforementioned solvents and water, and preferably alcohols or mixed solvents of alcohols and water.

There are no particular limitations on the optically active organic acid used in the aforementioned reaction, and examples include tartaric acid, mandelic acid or camphor-10-sulfonic acid, and preferably tartaric acid.

The resulting salt can be easily returned to the free form (XVI) by an ordinary extraction procedure using organic solvent and base.

The desired compounds of each step of Process D are recovered from the reaction mixture in accordance with ordinary methods. For example, in the case of suitably neutralizing the reaction mixture or when impurities are present, an organic solvent such as ethyl acetate that is not miscible with water is added after removing the impurities by filtration, and after washing with water and so forth, the organic layer containing the desired compound is separated, and after drying with anhydrous magnesium sulfate or anhydrous sodium sulfate, the desired compound is obtained by distilling off the solvent. The resulting desired compound can be separated and purified as necessary by suitably combining ordinary methods, such as recrystallization, reprecipitation or other method commonly used for separation and purification of organic compounds, examples of which include absorption column chromatography using a carrier such as silica gel, alumina or magnesium-silica gel-based Florisil; a method using a synthetic adsorbent such as partition column chromatography using a carrier such as Sephadex LH-20 (Pharmacia), Amberlite XAD-11 (Rohm and Haas) or Diaion HP-20 (Mitsubishi Chemical), a method using ion exchange chromatography, and a forward-phase, reverse-phase column chromatography method using silica gel or alkylated silica gel (and preferably high-performance liquid column chromatography), and eluting with a suitable eluent.

In the case of using an active ingredient of the present invention in the form of a compound having general formula (I), a pharmacologically acceptable salt thereof or a pharmacologically acceptable ester thereof as the aforementioned therapeutic or prophylactic, the active ingredient itself, or a mixture with a suitable pharmacologically acceptable vehicle or diluent and so forth can be administered orally in the form of, for example, a tablet, capsule, granules, powder or syrup, or parenterally in the form of an injection or suppository and so forth, and preferably administered orally in the form of a tablet or capsule.

These preparations can be produced by commonly known methods using an additive such as a vehicle (examples of which include sugar derivatives such as lactose, sucrose, glucose, mannitol or sorbitol; starch derivatives such as corn starch, potato starch, α-starch or dextrin; cellulose derivatives such as crystalline cellulose; organic vehicles such as pullulan; and, inorganic vehicles such as light silicic anhydride, synthetic aluminium silicate, calcium silicate or magnesium metasilicate aluminate), a lubricant (examples of which include stearic acid and stearic acid metal salts such as calcium stearate or magnesium stearate; talc; colloidal silica; waxes such as bee gum or spermaceti; boric acid; adipic acid; sulfates such as sodium sulfate; glycol; fumaric acid; sodium benzoate; DL-leucine; fatty acid sodium salts; lauryl sulfates such as sodium lauryl sulfate or magnesium lauryl sulfate; silicic acids such as silicic anhydride or silicic hydride; and, the aforementioned starch derivatives), a binder (examples of which include hydroxypropyl cellulose, hydroxypropyl methyl cellulose, polyvinylpyrrolidone, Macrogol and compounds similar to the aforementioned vehicles), a disintegrant (examples of which include cellulose derivatives such as lowly substituted hydroxypropyl cellulose, carboxymethyl cellulose, calcium carboxymethyl cellulose or internally crosslinked sodium carboxymethyl cellulose; and, chemically modified starches and celluloses such as carboxymethyl starch, sodium carboxymethyl starch and crosslinked polyvinylpyrrolidone), a stabilizer (examples of which include paraoxybenzoic acid esters such as methyl p-hydroxybenzoate or propyl p-hydroxybenzoate; alcohols such as chlorobutanol, benzyl alcohol or phenyl ethyl alcohol; phenols such as benzalkonium chloride, phenol or cresol; thimerosal; dehydroacetic acid; and, sorbic acid), or a diluent.

Although varying depending on symptoms, age and so forth, the human adult dosage of the active ingredient in the form of an amino alcohol compound, regardless of whether by oral administration or intravenous administration, is 0.0001 mg/kg to 1.0 mg/kg, and preferably 0.001 mg/kg to 0.1 mg/kg.

In the case of oral administration, although the number of administrations is normally. from one to three times per day to once per week depending on the case, since the pharmaceutical composition of the present invention has satisfactory physicochemical stability, biological absorptivity and pharmacokinetics (including blood half-life), it has the advantage of enabling the number of administrations to be lower than normal, and the number of administrations thereof is from once per day to once per week, and preferably from once per day to once in three days.

EXAMPLE

In the following, Examples and Test examples are shown and the present invention is explained in more detail but the scope of the present invention is not limited thereto.

Example 1

(2R) -2-Amino-2-methyl-4-{1-methyl-5-[4- (4-methylphenyl)butanoyl]pyrrol-2-yl}butan-1-ol hydrochloride (Exemplary Compound No. 19)

[Chemical Formula 16]

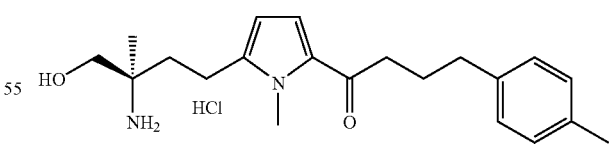

(1a) (2R)-1-Acetoxy-2-acetylamino-2-methyl-4-{1-methyl-5-[4-(4-methylphenyl)-1-(4-(4-methylphenyl)butanoyloxy)but-1-enyl]pyrrol-2-yl}butane Thionyl chloride (9.0 mL, 123 mmol) and N,N -dimethylformamide (50 µL) were added to a solution of 4-(4-methylphenyl)butyric acid (11.0 g, 62.0 mmol) in benzene (220 mL) and the mixture was stirred at 80° C. for 2 hours. After cooling the mixture to room temperature, the solvent was evaporated under reduced pressure to obtain 5-(4-methylphenyl)butyric chloride. A solution of 4-dimethylaminopyridine (15.2 g, 124 mmol) and 4-(4-methylphenyl)butyric chloride (12.2 g, 62.0 mmol) in toluene (50 mL) was added to a solution of (2R)-1-acetoxy-2-acetylamino-2-methyl-4-(1-methylpyrrol-2-yl)butane (5.00 g, 18.8 mmol) obtained in Reference example 1 in toluene (150 mL) and the mixture was stirred at 110° C. for 48 hours. The temperature of the mixture was returned to room temperature and ethyl acetate and water were added to the reaction mixture to separate it. The thus obtained organic phase was separated, washed with water and a saturated aqueous NaCl solution and dried over anhydrous sodium sulfate and the solvent was evaporated under reduced pressure. The residue was purified by silica gel chromatography (ethyl acetate:hexane, 3:2-2:1) to obtain the title compound (5.15 g, yield: 47%).

(1b) (2R)-2-Amino-2-methyl-4-{1-methyl-5-[4-(4-methylphenyl)butanoyl]pyrrol-2-yl}butan-1-ol hydrochloride (2R)-1-Acetoxy-2-acetylamino-2-methyl-4-{1-methyl-5-[4-(4-methylphenyl)-1-(4-(4-methylphenyl)butanoyloxy)but-1-enyl]pyrrol-2-yl}butane (5.15 g, 8.80 mmol) obtained in Example 1 (1a) was dissolved in a mixture of tetrahydrofuran (52 mL) and methanol (52 mL), and water (52 mL) and lithium hydroxide monohydrate (3.68 g, 87.7 mmol) were added thereto, followed by stirring of the mixture at 50° C. for 4 hours. After cooling, water and methylene chloride were added to the reaction mixture to separate it. The thus obtained organic phase was separated, washed with a saturated aqueous NaCl solution and dried over anhydrous sodium sulfate, and the solvent was evaporated under reduced pressure. The residue was purified by basic silica gel (NH type) chromatography (methylene chloride:metahanol, 100:1) to obtain (2R)-2-amino-2-methyl-4-{1-methyl-5-[4-(4-methylphenyl)butanoyl]pyrrol-2-yl}butan-1-ol (2.51 g). A 4N hydrochloric acid-dioxane solution (0.42 mL, 1.68 mmol) was added to a solution of the thus obtained (2R)-2-amino-2-methyl-4-{1-methyl-5-[4-(4-methylphenyl)butanoyl]pyrrol-2-yl}butan-1-ol (600 mg, 1.80 mmol) in methanol (9 mL) under ice-cooling and the mixture was stirred for 10 minutes. The mixture was concentrated under reduced pressure, ethyl acetate was added thereto and the precipitated crystal was collected by filtration. The crystal was washed with ethyl acetate and dried under reduced pressure to obtain the title compound (500 mg, yield: 86%).

Mp: 165-166° C.;

$[\alpha]_D$-4.848 (c 1.00, MeOH);

$^1$H NMR (CD$_3$OD, 400 MHz): δ 7.06-7.05 (m, 4H,), 6.96 (d, 1H, J=4.0 Hz), 6.02 (d, 1H, J=4.0 Hz), 3.86 (s, 3H), 3.65 (d, 1H, J=11.7 Hz), 3.55 (d, 1H, J=11.7 Hz), 2.74 (t, 2H, J=6.2 Hz), 2.72-2.65 (m, 2H), 2.61 (t, 2H, J=7.7 Hz), 2.29 (s, 3H), 2.03 (ddd, 1H, J=13.9, 9.5, 7.3 Hz), 1.94 (t, 1H, J=6.6 Hz), 1.92-1.86 (m, 2H), 1.35 (s, 3H);

IR $\upsilon_{max}$ cm$^{-1}$ (KBr): 3345, 3019, 2946, 2919, 2900, 1645, 1499, 1481, 1462, 1381, 1362, 1174, 1067, 1043, 770;

MS (FAB) m/z : 343 ((M+H)$^+$; free body);

Elementary analysis (% for C$_{21}$H$_{30}$N$_2$O$_2$.HCl.0.5 H$_2$O),

Calculated: C: 65.01, H: 8.31, N: 7.22;

Found: C: 64.58, H: 8.44, N: 7.26.

Example 2

(2R)-2-Amino-2-methyl-4-{1-methyl-5-[4-(3,4-dimethylphenyl)butanoyl]pyrrol-2-yl}butan-1-ol hydrochloride (Exemplary Compound No. 23)

[Chemical Formula 17]

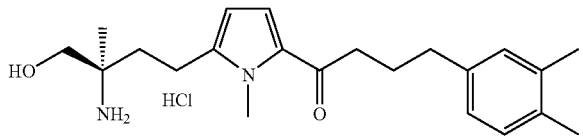

(2a) (2R)-1-Acetoxy-2-acetylamino-2-methyl-4-{1-methyl-5-[4-(3,4-dimethylphenyl)-1-(4-(3,4-dimethylphenyl)butanoyloxy)but-1-enyl]pyrrol-2-yl}butane The reaction was carried out in the similar manner to Example 1 (1a) using 4-(3,4-dimethylphenyl)butyric acid obtained in Reference example 4 and (2R)-1-acetoxy-2-acetylamino-2-methyl-4-(1-methylpyrrol-2-yl)butane obtained in Reference example 1 to obtain the title compound (yield: 65%).

(2b) (2R)-2-Amino-2-methyl-4-{1-methyl-5-[4-(3,4-dimethylphenyl)butanoyl]pyrrol-2-yl}butan-1-ol hydrochloride The reaction was carried out in the similar manner to Example 1 (1b) using (2R)-1-acetoxy-2-acetylamino-2-methyl-4-{1-methyl-5-[4-(3,4-dimethylphenyl)-1-(4-(3,4-dimethylphenyl)butanoyloxy)but-1-enyl]pyrrol-2-yl}butane obtained in Example 2 (2a) to obtain the title compound (yield: 64%).

$^1$H NMR (CD$_3$OD, 400 MHz): δ 6.99 (d, 1H, J=7.7 Hz), 6.96 (d, 1H, J=4.0 Hz), 6.93 (s, 1H), 6.87 (d, 1H, J=7.7 Hz), 6.02 (d, 1H, J=4.0 Hz), 3.86 (s, 3H), 3.65 (d, 1H, J=11.7 Hz), 3.55 (d, 1H, J=11.7 Hz), 2.76-2.63 (m, 4H), 2.57 (t, 2H, J=7.3 Hz), 2.21 (s, 3H), 2.21 (s, 3H), 2.07-2.01 (m, 1H), 1.93 (t, 1H, J=7.3 Hz), 1.99-1.86 (m, 2H), 1.35 (s, 3H);

IR $\upsilon_{max}$ cm$^{-1}$ (KBr): 3354, 2947, 2898, 1645, 1502, 1480, 1380, 1354, 1174, 1066, 986, 911, 769;

MS (FAB) m/z: 357 ((M+H)$^+$; free body);

Elementary analysis (% for C$_{21}$H$_{30}$N$_2$O$_2$.HCl),

Calculated: C: 67.24, H: 8.46, N: 7.13;

Found: C: 67.09, H: 8.41, N: 7.29.

Example 3

(2R)-2-Amino-2-methyl-4-{1-methyl-5-[4-(2,3-dimethylphenyl)butanoyl]pyrrol-2-yl}butan-1-ol hydrochloride (Exemplary compound No. 20)

[Chemical Formula 18]

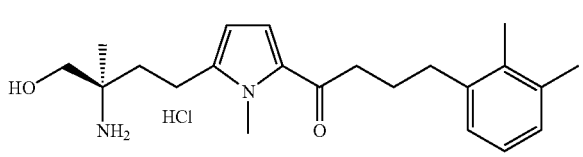

(3a) (2R)-1-Acetoxy-2-acetylamino-2-methyl-4-{1-methyl-5-[4-(2,3-dimethylphenyl)-1-(4-(2,3-dimethylphenyl)butanoyloxy)but-1-enyl]pyrrol-2-yl}butane The reaction was carried out in the similar manner to Example 1 (1a) using 4-(2,3-dimethylphenyl)butyric acid obtained in Reference example 5 and (2R)-1-acetoxy-2-acetylamino-2-methyl-4-(1-methylpyrrol-2-yl)butane obtained in Reference example 1 to obtain the title compound (yield: 69%).

(3b) (2R)-2-Amino-2-methyl-4-{1-methyl-5-[4-(2,3-dimethylphenyl)butanoyl]pyrrol-2-yl}butan-1-ol hydrochloride The reaction was carried out in the similar manner to Example 1 (1b) using (2R)-1-acetoxy-2-acetylamino-2-methyl-4-{1-methyl-5-[4-(2,3-dimethylphenyl)-1-(4-(2,3-dimethylphenyl)butanoyloxy)but-1-enyl]pyrrol-2-yl}butane obtained in Example 3 (3a) to obtain the title compound (yield: 84%).

$^1$H NMR (CD$_3$OD, 400 MHz): δ 6.97 (d, 1H, J=4.3 Hz), 6.95-6.91 (m, 3H), 6.05 (d, 1H, J=4.3 Hz), 3.85 (s, 3H), 3.64 (d, 1H, J=11.3 Hz), 3.54 (d, 1H, J=11.3 Hz), 2.78 (t, 2H, J=7.4 Hz), 2.73-2.63 (m, 4H), 2.24 (s; 3H), 2.19 (s, 3H), 2.07-1.98 (m, 1H), 1.94-1.84 (m, 3H), 1.34 (s, 3H);

IR υ$_{max}$ cm$^{-1}$ (KBr): 3387, 3104, 2948, 2896, 1641, 1589, 1481, 1462, 1384, 1362, 1072, 769;

MS (FAB) m/z: 357 ((M+H)$^+$; free body);
Elementary analysis (% for C$_{22}$H$_{33}$N$_2$O$_2$.HCl),
Calculated: C: 67.24, H: 8.75, N: 6.84, Cl: 9.02;
Found: C: 67.10, H: 8.75, N: 6.89, Cl: 8.84.

Example 4

(2R)-2-Amino-2-methyl-4-{1-methyl-5-[4-(2,4-dimethylphenyl)butanoyl]pyrrol-2-yl}butan-1-ol hydrochloride (Exemplary compound No. 21)

[Chemical Formula 19]

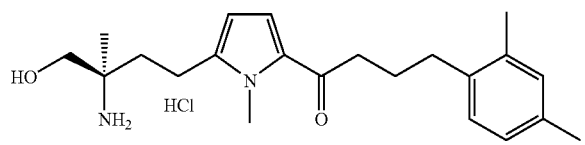

(4a) (2R)-1-Acetoxy-2-acetylamino-2-methyl-4-{1-methyl-5-[4-(2,4-dimethylphenyl)-1-(4-(2,4-dimethylphenyl)butanoyloxy)but-1-enyl]pyrrol-2-yl}butane The reaction was carried out in the similar manner to Example 1 (1a) using 4-(2,4-dimethylphenyl)butyric acid obtained in Reference example 6 and (2R)-1-acetoxy-2-acetylamino-2-methyl-4-(1-methylpyrrol-2-yl)butane obtained in Reference example 1 to obtain the title compound (yield: 63%).

(4b) (2R)-2-Amino-2-methyl-4-{1-methyl-5-[4-(2,4-dimethylphenyl)butanoyl]pyrrol-2-yl}butan-1-ol hydrochloride The reaction was carried out in the similar manner to Example 1 (1b) using (2R)-1-acetoxy-2-acetylamino-2-methyl-4-{1-methyl-5-[4-(2,4-dimethylphenyl)-1-(4-(2,4-dimethylphenyl)butanoyloxy)but-1-enyl]pyrrol-2-yl}butane obtained in Example 4 (4a) to obtain the title compound (yield: 62%).

$^1$H NMR (CD$_3$OD, 400 MHz): δ 6.99 (d, 1H, J=4.4 Hz), 6.98 (d, 1H, J=8.4 Hz), 6.92 (s, 1H), 6.88 (d, 1H, J=8.4 Hz), 6.03 (d, 1H, J=4.4 Hz), 3.87 (s, 3H), 3.65 (d, 1H, J=11.7 Hz), 3.55 (d, 1H, J=11.7 Hz), 2.78 (t, 2H, J=7.3 Hz), 2.75-2.65 (m, 2H), 2.61 (t, 2H, J=7.3 Hz), 2.24 (s, 3H), 2.24 (s, 3H), 2.07-1.99 (m, 1H), 1.94-1.85 (m, 3H), 1.35 (s, 3H);

IR υ$_{max}$ cm$^{-1}$ (KBr): 3353, 3014, 2974, 2948, 2918, 2898, 1645, 1501, 1480, 1461, 1381, 800;

MS (FAB) m/z: 357 ((M+H)$^+$; free body);
Elementary analysis (% for C$_{21}$H$_{30}$N$_2$O$_2$.HCl),
Calculated: C: 67.24, H: 8.46, N: 7.13;
Found: C: 64.75, H: 8.36, N: 6.95.

Example 5

(2R)-2-Amino-2-methyl-4-{1-methyl-5-[4-(4-t-butylphenyl)butanoyl]pyrrol-2-yl}butan-1-ol hydrochloride (Exemplary compound No. 36)

[Chemical Formula 20]

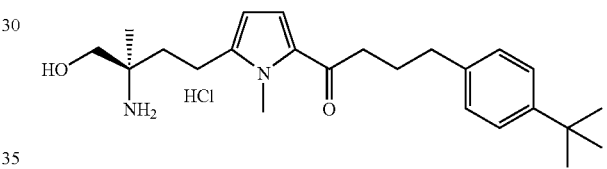

(5a) (2R)-1-Acetoxy-2-acetylamino-2-methyl-4-{1-methyl-5-[4-(4-t-butylphenyl)-1-(4-(4-t-butylphenyl)butanoyloxy)but-1-enyl]pyrrol-2-yl}butane The reaction was carried out in the similar manner to (1a) using 4-(4-t-butylphenyl)butyric acid obtained in Reference example 7 and (2R)-1-acetoxy-2-acetylamino-2-methyl-4-(1-methylpyrrol-2-yl)butane obtained in Reference example 1 to obtain the title compound (yield: 59%).

(5b) (2R)-2-Amino-2-methyl-4-{1-methyl-5-[4-(4-t-butylphenyl)butanoyl]pyrrol-2-yl}butan-1-ol hydrochloride The reaction was carried out in the similar manner to Example 1 (1b) using (2R)-1-acetoxy-2-acetylamino-2-methyl-4-{1-methyl-5-[4-(4-t-butylphenyl)-1-(4-(4-t-butylphenyl)butanoyloxy)but-1-enyl]pyrrol-2-yl}butane obtained in Example 5 (5a) to obtain the title compound (yield: 62%).

$^1$H NMR (CD$_3$OD, 500 MHz): δ 7.29 (d, 2H, J=8.3 Hz), 7.10 (d, 2H, J=8.3 Hz), 6.96 (d, 1H, J=3.9 Hz), 6.02 (d, 1H, J=3.9 Hz), 3.86 (s, 3H), 3.65 (d, 1H, J=11.2 Hz), 3.55 (d, 1H, J=11.2 Hz), 2.75 (t, 2H, J=7.3 Hz), 2.65-2.71 (m, 2H), 2.62 (t, 2H, J=7.3 Hz), 1.86-2.06 (m, 4H), 1.35 (s, 3H), 1.30 (s, 9H);

IR υ$_{max}$ cm$^{-1}$ (KBr): 3369, 2956, 1647, 1479, 1460, 1382, 1063, 1041;

MS (FAB) m/z: 385 ((M+H)$^+$; free body);

Example 6

(2R)-2-Amino-2-methyl-4-{1-methyl-5-[4-(4-isopropylphenyl)butanoyl]pyrrol-2-yl}butan-1-ol hydrochloride (Exemplary compound No. 33)

[Chemical Formula 21]

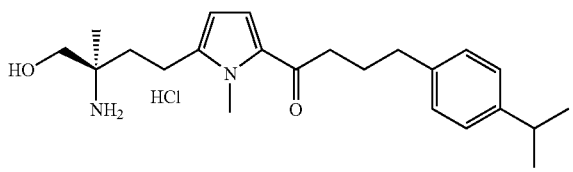

(6a) (2R)-1-Acetoxy-2-acetylamino-2-methyl-4-{1-methyl-5-[4-(4-isopropylphenyl)-1-(4-(4-isopropylphenyl)butanoyloxy)but-1-enyl]pyrrol-2-yl}butane The reaction was carried out in the similar manner to Example 1 (1a) using 4-(4-isopropylphenyl)butyric acid obtained in Reference example 8 and (2R)-1-acetoxy-2-acetylamino-2-methyl-4-(1-methylpyrrol-2-yl)butane obtained in Reference example 1 to obtain the title compound (yield: 58%).

(6b) (2R)-2-Amino-2-methyl-4-{1-methyl-5-[4-(4-isopropylphenyl)butanoyl]pyrrol-2-yl}butan-1-ol hydrochloride The reaction was carried out in the similar manner to Example 1 (1b) using (2R)-1-acetoxy-2-acetylamino-2-methyl-4-{1-methyl-5-[4-(4-isopropylphenyl)-1-(4-(4-isopropylphenyl)butanoyloxy)but-1-enyl]pyrrol-2-yl}butane obtained in Example 6 (6a) to obtain the title compound (yield: 59%).

$^1$H NMR (CD$_3$OD, 400 MHz): δ 7.13 (d, 1H, J=8.1 Hz), 7.11 (d, 1H, J=7.3 Hz), 7.11 (d, 1H, J=7.3 Hz), 7.09 (d, 1H, J=8.1 Hz), 6.97 (d, 1H, J=4.4 Hz), 6.10 (d, 1H, J=4.4 Hz), 3.86 (s, 3H), 3.65 (d, 1H, J=11.3 Hz), 3.55 (d, 1H, J=11.3 Hz), 2.85 (tt, 1H, J=7.3, 7.3 Hz), 2.75 (t, 2H, J=7.3 Hz), 2.72-2.67 (m, 2H), 2.63 (t, 2H, J=7.3 Hz), 2.07-2.00 (m, 1H), 1.98-1.85 (m, 1H), 1.94 (t, 1H, J=8.1 Hz), 1.34 (s, 3H), 1.22 (d, 3H, J=7.3 Hz), 1.22 (d, 3H, J=7.3 Hz);

IR υ$_{max}$ cm$^{-1}$ (KBr): 3348, 3208, 3008, 2956, 2897, 1646, 1480, 1460, 1382, 1175, 1057, 1041, 987, 917, 811, 771;

MS (FAB) m/z: 371 ((M+H)$^+$; free body);

Elementary analysis (% for C$_{21}$H$_{30}$N$_2$O$_2$.HCl),
Calculated: C: 66.12, H: 8.73, N: 6.71;
Found: C: 65.93, H: 8.76, N: 6.77.

Example 7

(2R)-2-Amino-2-methyl-4-{1-methyl-5-[4-(4-cyclopropylphenyl)butanoyl]pyrrol-2-yl}butan-1-ol hydrochloride (Exemplary compound No. 30)

[Chemical Formula 22]

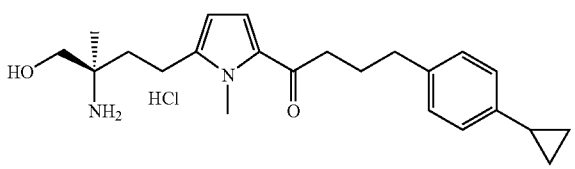

(7a) (2R)-1-Acetoxy-2-acetylamino-2-methyl-4-(1-methyl-5-{4-(4-cyclopropylphenyl)-1-[4-(4-cyclopropylphenyl)butanoyloxy]but-1-enyl}pyrrol-2-yl)butane The reaction was carried out in the similar manner to Example 1 (1a) using 4-(4-cyclopropylphenyl)butyric acid obtained in Reference example 9 and (2R)-1-acetoxy-2-acetylamino-2-methyl-4-(1-methylpyrrol-2-yl)butane obtained in Reference example 1 to obtain the title compound (yield: 54%).

(7b) (2R)-2-Amino-2-methyl-4-{1-methyl-5-[4-(4-cyclopropylphenyl)butanoyl]pyrrol-2-yl}butan-1-ol hydrochloride The reaction was carried out in the similar manner to Example 1 (1b) using (2R)-1-acetoxy-2-acetylamino-2-methyl-4-(1-methyl-5-{4-(4-cylopropylphenyl)-1-[4-(4-cyclopropylphenyl)butanoyloxy]but-1-enyl}pyrrol-2-yl)butane obtained in Example 7 (7a) to obtain the title compound (yield: 84%).

$^1$H NMR (CD$_3$OD, 400 MHz): δ 7.05 (d, 2H, J=8.3Hz), 6.98-6.95 (m, 3H), 6.02 (d, 1H, J=3.9 Hz), 3.86 (s, 3H), 3.65 (d, 1H, J=11.7 Hz), 3.55 (d, 1H, J=11.7 Hz), 2.75-2.67 (m, 4H), 2.60 (t, 2H, J=7.3Hz), 2.07-2.00 (m, 1H), 1.97-1.82 (m, 4H), 1.35 (s, 3H), 0.93-0.87 (m, 2H), 0.64-0.60 (m, 2H);

MS (FAB) m/z: 369 ((M+H)$^+$; free body);

Elementary analysis (% for C$_{23}$H$_{32}$N$_2$O$_2$.HCl. 0.5H$_2$O),
Calculated: C: 66.73, H: 8.28, N: 6.77;
Found: C: 66.85, H: 8.14, N: 6.89.

Example 8

(2R)-2-Amino-2-methyl-4-{1-methyl-5-[4-(4-fluorophenyl)butanoyl]pyrrol-2-yl}butan-1-ol hydrochloride (Exemplary compound No. 3)

[Chemical Formula 23]

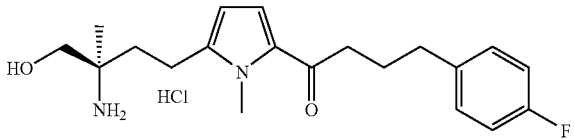

(8a) (2R)-1-Acetoxy-2-acetylamino-2-methyl-4-{1-methyl-5-[4-(4-fluorophenyl)-1-(4-(4-fluorophenyl)butanoyloxy)but-1-enyl]pyrrol-2-yl}butane The reaction was carried out in the similar manner to Example 1 (1a) using 5-(4-fluorophenyl)butyric acid obtained in Reference example 10 and (2R)-1-acetoxy-2-acetylamino-2-methyl -4-(1-methylpyrrol-2-yl)butane obtained in Reference example 1 to obtain the title compound (yield: 17%).

(8b) (2R)-2-Amino-2-methyl-4-{1-methyl-5-[4-(4-fluorophenyl)butanoyl]pyrrol-2-yl}butan-1-ol hydrochloride The reaction was carried out in the similar manner to Example 1 (1b) using (2R)-1-acetoxy-2-acetylamino-2-methyl -4-{1-methyl-5-[4-(4-fluorophenyl)-1-(4-(4-fluorophenyl)butanoyloxy)but-1-enyl]pyrrol-2-yl}butane obtained in Example 8 (8a) to obtain the title compound (yield: 29%).

$^1$H NMR (DMSO-d6, 400 MHz): δ 7.24-7.20 (m, 2H,), 7.11-7.07 (m, 2H,), 6.99 (d, 1H, J=4.0 Hz), 5.94 (d, 1H, J=4.0 Hz), 5.50 (s, 1H,), 3.79 (s, 3H), 3.48 (d, 1H, J=11.2 Hz), 3.43 (d, 1H, J=11.2 Hz), 2.71 (t, 2H, J=7.6 Hz), 2.64-2.57 (m, 4H), 1.88-1.79 (m, 4H), 1.21 (s, 3H);
IR $\upsilon_{max}$ cm$^{-1}$ (KBr): 3366, 3175, 2942, 2688, 2573, 1636, 1509, 1483, 1459, 1381, 1217, 1059, 988, 775;
MS (FAB) m/z: 347 ((M+H)$^+$; free body);
Elementary analysis (% for $C_{20}H_{27}N_2O_2F.HCl$),
Calculated: C: 62.74, H: 7.37, N: 7.32;
Found: C: 62.68, H: 7.07, N: 7.37.

Example 9

(2R)-2-Amino-2-methyl-4-{1-methyl-5-[4-(4-trifluoromethylphenyl)butanoyl]pyrrol-2-yl}butan-1-ol hydrochloride (Exemplary compound No. 66)

[Chemical Formula 24]

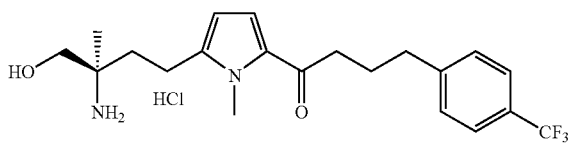

(9a) (2R)-1-Acetoxy-2-acetylamino-2-methyl-4-{1-methyl-5-[4-(4-trifluoromethylphenyl)-1-(4-(4-trifluoromethylphenyl)butanoyloxy)but-1-enyl]pyrrol-2-yl}butane The reaction was carried out in the similar manner to Example 1 (1a) using 4-(4-trifluoromethylphenyl)butyric acid obtained in Reference example 11 and (2R)-1-acetoxy-2-acetylamino-2-methyl-4-(1-methylpyrrol-2-yl)butane obtained in Reference example 1 to obtain the title compound (yield: 28%).

(9b) (2R)-2-Amino-2-methyl-4-{1-methyl-5-[4-(4-trifluoromethylphenyl)butanoyl]pyrrol-2-yl}butan-1-ol hydrochloride The reaction was carried out in the similar manner to Example 1 (1b) using (2R)-1-acetoxy-2-acetylamino-2-methyl -4-{1-methyl-5-[4-(4-trifluoromethylphenyl)-1-(4-(4-trifluoromethylphenyl)butanoyloxy)but-1-enyl]pyrrol-2-yl}butane obtained in Example 9 (9a) to obtain the title compound (yield: 56%).

$^1$H NMR (CDCl$_3$, 400 MHz): δ 7.51 (d, 2H, J=8.6 Hz), 7.28 (d, 2H, J=8.6 Hz), 6.79 (d, 1H, J=4.1 Hz), 5.92 (d, 1H, J=4.1 Hz), 3.83 (s, 3H), 3.68 (s, 2H), 2.76-2.65 (m, 6H), 2.05-1.95 (m, 4H), 1.60 (bs, 3H), 1.38 (s, 3H);
IR $\upsilon_{max}$ cm$^{-1}$ (KBr): 3362, 2947, 1645, 1480, 1325, 1174, 1129, 1067;
MS (FAB) m/z: 397 ((M+H)$^+$; free body);
Elementary analysis (% for $C_{21}H_{27}N_2O_2F_3.HCl.H_2O$),
Calculated: C: 55.94, H: 6.71, N: 6.21;
Found: C: 55.99, H: 6.51; N: 6.28.

Example 10

(2R)-2-Amino-2-methyl-4-{1-methyl-5-[4-(4-cyanophenyl)butanoyl]pyrrol-2-yl}butan-1-ol ½ fumarate (Exemplary compound No. 73)

[Chemical Formula 25]

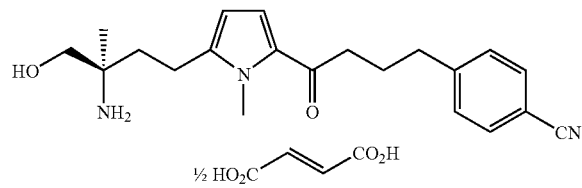

(10a) (2R)-1-Acetoxy-2-acetylamino-2-methyl-4-{1-methyl-5-[4-(4-cyanophenyl)-1-(4-(4-cyanophenyl)butanoyloxy)but-1-enyl]pyrrol-2-yl}butane The reaction was carried out in the similar manner to Example 1 (1a) using 4-(4-cyanophenyl)butyric acid obtained in Reference example 12 and (2R)-1-acetoxy-2-acetylamino-2-methyl-4-(1-methylpyrrol-2-yl)butane obtained in Reference example 1 to obtain the title compound (yield: 74%).

(10b) (2R)-2-Amino-2-methyl-4-{1-methyl-5-[4-(4-cyanophenyl)butanoyl]pyrrol-2-yl}butan-1-ol ½ fumarate (2R)-1-Acetoxy-2-acetylamino-2-methyl-4-{1-methyl-5-[4-(4-cyanolphenyl)-1-(4-(4-cyanophenyl)butanoyloxy)but-1-enyl]pyrrol2-yl}butane (4.10 g, 6.90 mmol) obtained in Example 10 (10a) was dissolved in a mixture of tetrahydrofuran (10 mL) and methanol (10 mL), and water (10 mL) and lithium hydroxide monohydrate (2.90 g, 69 mmol) were added thereto, followed by stirring of the mixture at 80° C. for 1 hour. After cooling, water and methylene chloride were added to the reaction mixture to separate it. The thus obtained organic phase was separated, washed with a saturated aqueous NaCl solution and dried over anhydrous sodium sulfate. The solvent was evaporated under reduced pressure and the residue was purified by basic silica gel (NH type) chromatography (methylene chloride:methanol, 100:1) to obtain (2R)-2-amino-2-methyl-4-{1-methyl-5-[4-(4-cyanophenyl)butanoyl]pyrrol-2-yl}butan-1-ol (1.90 g, yield: 79%). A solution of fumaric acid (0.630 g, 5.40 mmol) in methanol (10 mL) was added to a solution of the thus obtained (2R)-2-amino-2-methyl-4-{1-methyl-5-[4-(4-cyanophenyl)butanoyl]pyrrol-2-yl}butan-1-ol (1.90 g, 5.40 mmol) in methanol (10 mL) under ice-cooling. After methanol was evaporated under reduced pressure, the residue was dissolved in a small amount of methanol, ethyl acetate was added thereto and recrystallization was carried out to obtain a crude crystal (1.29 g) of the title compound. Recrystallization of the thus obtained crude crystal (1.29 g) was carried out again using methanol to obtain the title compound (1.01 g, yield: 45%) as a white crystal.

$^1$H NMR (CD$_3$OD, 500 MHz): δ7.62 (d, 2H, J=8.3 Hz), 7.39 (d, 2H, J=8.3 Hz), 6.99 (d, 1H, J=3.9 Hz), 6.65 (s, 1H), 6.02 (d, 1H, J=3.9 Hz), 3.85 (s, 3H), 3.62 (d, 1H, J=11.7 Hz), 3.54 (d, 1H, J=11.7 Hz), 2.65-2.80 (m, 6H), 1.96-2.04 (m, 3H), 1.85-1.93 (m, 1H), 1.32 (s, 3H);

IR $\upsilon_{max}$ cm$^{-1}$ (KBr): 3402, 3275, 2582, 2228, 2135, 1644, 1567, 1548, 1381, 1361;

MS (FAB) m/z: 354 ((M+H)$^+$; free body);

Elementary analysis (% for C$_{21}$H$_{27}$N$_3$O$_2$.0.5 (C$_4$H$_4$O$_4$).H$_2$O), Calculated: C: 64.32, H: 7.27, N: 9.78;
Found: C: 64.67, H: 6.92, N: 9.82.

Example 11

(2R)-2-Amino-2-methyl-4-{1-methyl-5-[4-(3-methyl-4-methoxyphenyl)butanoyl]pyrrol-2-yl}butan-1-ol hydrochloride (Exemplary compound No. 57)

[Chemical Formula 26]

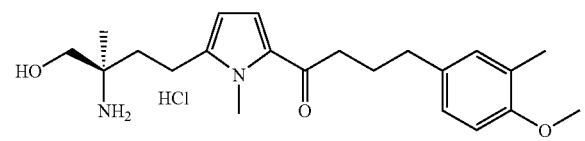

(11a) (2R)-1-Acetoxy-2-acetylamino-2-methyl-4-{1-methyl-5-[4-(3-methyl-4-methoxyphenyl)-1-(4-(3-methyl-4-methoxyphenyl)butanoyloxy)but-1-enyl]pyrrol-2-yl}butane The reaction was carried out in the similar manner to Example 1 (1a) using 4-(3-methyl-4-methoxyphenyl)butyric acid obtained in Reference example 13 and (2R)-1-acetoxy-2-acetylamino-2-methyl-4-(1-methylpyrrol-2-yl)butane obtained in Reference example 1 to obtain the title compound (yield: 37%).

(11b) (2R)-2-Amino-2-methyl-4-{1-methyl-5-[4-(3-methyl-4-methoxyphenyl)butanoyl]pyrrol-2-yl}butan-1-ol hydrochloride The reaction was carried out in the similar manner to Example 1 (1b) using (2R)-1-acetoxy-2-acetylamino-2-methyl-4-{1-methyl-5-[4-(3-methyl-4-methoxyphenyl)-1-(4-(3-methyl-4-methoxyphenyl)butanoyloxy)but-1-enyl]pyrrol-2-yl}butane obtained in Example 11 (11a) to obtain the title compound (yield: 64%).

$^1$H NMR (DMSO, 400 MHz): δ 8.00 (br, 3H), 6.98-6.95 (m, 3H), 6.81 (d, 1H, J=8.1 Hz), 5.94 (d, 1H, J=3.7 Hz), 5.53 (t, 1H, J=5.1 Hz), 3.80 (s, 3H), 3.77 (s, 3H), 3.52-3.42 (m, 2H), 2.72-2.63 (m, 4H), 2.60-2.48 (m, 2H), 2.11 (s, 3H), 1.89-1.78 (m, 4H), 1.23 (s, 3H);

IR $\upsilon_{max}$ cm$^{-1}$ (KBr): 3365, 2999, 2837, 1630, 1505, 1486, 1463, 1375, 1253, 1228, 1133, 1067, 1032, 904;

MS (FAB) m/z: 373 ((M+H)$^+$; free body);

Elementary analysis (% for C$_{21}$H$_{30}$N$_2$O$_2$.HCl),

Calculated: C: 64.61, H: 8.13, N: 6.85;
Found: C: 63.78, H: 8.16, N: 6.69.

Example 12

(2R)-2-Amino-2-ethyl-4-{1-methyl-5-[4-(4-methylphenyl)butanoyl]pyrrol-2-yl}butan-1-ol hydrochloride (Exemplary compound No. 165)

[Chemical Formula 27]

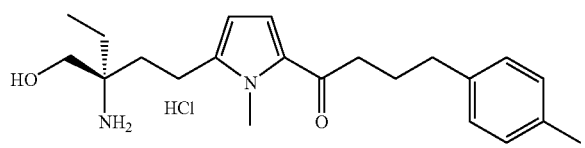

(12a) (2R)-1-Acetoxy-2-acetylamino-2-ethyl-4-{1-methyl-5-[4-(4-methylphenyl)-1-(4-(4-methylphenyl)butanoyloxy)but-1-enyl]pyrrol-2-yl}butane A solution of 4-dimethylaminopyridine (1.17 g, 11.8 mmol) and 4-(4-methylphenyl)butyric chloride (1.06 g, 5.90 mmol) in toluene (5 mL) was added to a solution of (2R)-1-acetoxy-2-acetylamino-2-ethyl-4-(1-methylpyrrol-2-yl)butane (444 mg, 1.60 mmol) obtained in Reference example 2 in toluene (15 mL) and the mixture was stirred at 110° C. for 72 hours. The temperature of the mixture was returned to room temperature and ethyl acetate and water were added to the reaction mixture to separate it. The thus obtained organic phase was separated, washed with water and a saturated aqueous NaCl solution and dried over anhydrous sodium sulfate. After filtration, the solvent was evaporated under reduced pressure and the residue was purified by silica gel chromatography (ethyl acetate:hexane, 3:2-2:1) to obtain the title compound (377 mg, yield: 40%).

(12b) (2R)-2-Amino-2-ethyl-4-{1-methyl-5-[4-(4-methylphenyl)butanoyl]pyrrol-2-yl}butan-1-ol hydrochloride (2R)-1-Acetoxy-2-acetylamino-2-ethyl-4-{1-methyl-5-[4-(4-methylphenyl)-1-(4-(4-methylphenyl)butanoyloxy)but-1-enyl]pyrrol-2-yl}butane (372 mg, 0.620 mmol) obtained in Example 12 (12a) was dissolved in a mixture of tetrahydrofuran (5 mL) and methanol (5 mL), and water (5 mL) and lithium hydroxide monohydrate (260 mg, 6.20 mmol) were added thereto, followed by stirring of the mixture at 50° C. for 4 hours. After cooling, water was added to the reaction mixture and methylene chloride was added thereto to separate it. The thus obtained organic phase was separated, washed with a saturated aqueous NaCl solution and dried over anhydrous sodium sulfate. After filtration, the solvent was evaporated under reduced pressure and the residue was purified by basic silica gel (NH type) chromatography (methylene chloride:methanol, 100:1) to obtain crude (2R)-2-amino-2-ethyl-4-{1-methyl-5-[4-(4-methylphenyl)butanoyl]pyrrol-2-yl}butan-1-ol (206 mg). A 4N hydrochloric acid-dioxane solution (0.135 mL, 0.54 mmol) was added to a solution of the thus obtained crude product in methanol (5.0 mL) under ice-cooling and the mixture was stirred for 10 minutes. The mixture was concentrated under reduced pressure, ethyl acetate was added thereto and the precipitated crystal was collected by filtration. The crystal was washed with ethyl acetate and dried under reduced pressure to obtain the title compound (212 mg, yield: 88%).

$^1$H NMR (CD$_3$OD, 400 MHz): δ 7.06 (m, 4H), 6.97 (d, 1H, J=3.9 Hz), 6.02 (d, 1H, J=3.9 Hz), 3.86 (s, 3H), 3.65 (d, 1H, J=11.7 Hz), 3.61 (d, 1H, J=11.7 Hz), 2.74 (t, 2H, J=7.4 Hz), 2.69-2.64 (m, 2H), 2.61 (t, 2H, J=7.4 Hz), 2.28 (s, 3H), 2.04-1.90 (m, 4H) 1.81-1.71 (m, 2H), 1.01 (t, 3H, J=7.4 Hz);

MS (FAB) m/z: 357 ((M+H)$^+$; free body).

Example 13

(2R)-2-Amino-2-methyl-4-{1-ethyl-5-[4-(4-methylphenyl)butanoyl]pyrrol-2-yl}butan-1-ol hydrochloride (Exemplary compound No. 92)

[Chemical Formula 28]

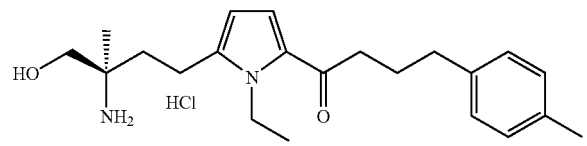

(13a) (2R)-1-Acetoxy-2-acetylamino-2-methyl-4-{1-ethyl-5-[4-(4-methylphenyl)-1-(4-(4-methylphenyl)butanoyloxy)but-1-enyl]pyrrol-2-yl}butane A solution of 4-dimethylaminopyridine (1.30 g, 10.6 mmol) and 4-(4-methylphenyl)butyric chloride (1.05 g, 5.3 mmol) in toluene (10 mL) was added to a solution of (2R)-1-acetoxy-2-acetylamino-2-methyl-4-(1-methylpyrrol-2-yl)butane (500 mg, 1.80 mmol) obtained in Reference example 3 in toluene (20 mL) and the mixture was stirred at 110° C. for 78 hours. The temperature of the mixture was returned to room temperature and ethyl acetate and water were added to the reaction mixture to separate it. The thus obtained organic phase was separated, washed with water and a saturated aqueous NaCl solution and dried over anhydrous sodium sulfate. After filtration, the solvent was evaporated under reduced pressure and the residue was purified by silica gel chromatography (ethyl acetate:hexane, 3:2) to obtain the title compound (751 mg, yield: 70%).

(13b) (2R)-2-Amino-2-methyl-4-{1-ethyl-5-[4-(4-methylphenyl)butanoyl]pyrrol-2-yl}butan-1-ol hydrochloride (2R)-1-Acetoxy-2-acetylamino-2-methyl-4-{1-ethyl-5-[4-(4-methylphenyl)-1-(4-(4-methylphenyl)butanoyloxy)but-1-enyl]pyrrol-2-yl}butane (750 mg, 1.20 mmol) obtained in Example 13 (13a) was dissolved in a mixture of tetrahydrofuran (7 mL) and methanol (7 mL), and water (7 mL) and lithium hydroxide monohydrate (530 mg, 12.6 mmol) were added thereto, followed by stirring of the mixture at 50° C. for 7 hours. After cooling, water and methylene chloride were added to the reaction mixture to separate it. The thus obtained organic phase was separated, washed with a saturated aqueous NaCl solution and dried over anhydrous sodium sulfate. After filtration, the solvent was evaporated under reduced pressure and the residue was purified by basic silica gel (NH type) chromatography (methylene chloride:methanol, 97:3) to obtain crude (2R)-2-amino-2-methyl-4-{1-ethyl-5-[4-(4-methylphenyl)butanoyl]pyrrol-2-yl}butan-1-ol (251 mg). A 4N hydrochloric acid-dioxane solution (0.360 mL, 1.40 mmol) was added to a solution of the thus obtained crude product in ethanol (5 mL) under ice-cooling and the mixture was stirred for 10 minutes. The mixture was concentrated under reduced pressure, ethyl acetate was added thereto and the precipitated crystal was collected by filtration. The crystal was washed with ethyl acetate and dried under reduced pressure to obtain the title compound (215 mg, yield: 44%).

$^1$H NMR (DMSO-d$_6$, 400 MHz): δ 7.90 (br s, 2H), 7.11-7.04 (m, 4H) 7.00 (d, 1H, J=3.7 Hz), 5.95 (d, 1H, J=3.7 Hz), 5.53 (br s, 1H), 4.30 (q, 2H, J=7.0 Hz), 3.53-3.39 (m, 2H), 2.72 (t, 2H, J=7.3 Hz), 2.64 (t, 2H, J=8.4 Hz), 2.55 (t, 2H, J=7.3 Hz), 2.26 (s, 3H), 1.95-1.78 (m, 4H), 1.22 (s, 3H), 1.18 (t, 3H, J=7.0 Hz);

MS (FAB) m/z : 357 ((M+H)$^+$; free body)

Example 14

(2R)-2-Amino-2-methyl-4-{1-methyl-5-[4-(4-methylphenyl)butanoyl]pyrrol-2-yl}butan-1-ol 1/2 fumarate (Exemplary compound No. 19)

[Chemical Formula 29]

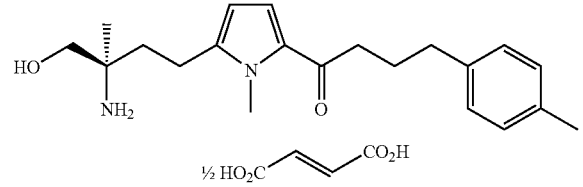

Fumaric acid (94.9 mg, 0.82 mmol) was added to a solution of (2R)-2-amino-2-methyl-4-{1-methyl-5-[4-(4-methylphenyl)butanoyl]pyrrol-2-yl}butan-1-ol (560 mg, 1.6 mmol) obtained in Example 1 (1b) in ethanol (18 mL) at room temperature and the mixture was left to stand for 15 hours. The precipitated crystal was collected by filtration to obtain the title compound (622.7 mg, yield: 95%).

$^1$H NMR (CD$_3$OD, 400 MHz): δ 7.08-7.03 (m, 4H,), 6.96 (d, 1H, J=3.7 Hz), 6.65 (s, 0.5×2H), 6.01 (d, 1H, J=4.3 Hz), 3.85 (s, 3H), 3.62 (d, 1H, J=11.0 Hz), 3.54 (d, 11.0 Hz, J=11.0 Hz), 2.73 (t, 2H, J=7.3 Hz), 2.69 (t, 2H, J=8.4 Hz), 2.60 (t, 2H, J=7.8 Hz), 2.28 (s, 3H), 2.01-1.84 (m, 4H), 1.32 (s, 3H);

MS (FAB) m/z: 343 ((M+H)$^+$; free body);

Elementary analysis (% for C$_{21}$H$_{30}$N$_2$O$_2$·0.5C$_4$H$_4$O$_4$),

Calculated: C: 68.97, H: 8.05, N: 6.99;

Found: C: 69.06, H: 7.82, N: 7.08.

Example 15

(2R)-2-Amino-2-methyl-4-{1-methyl-5-[4-(3,4-dimethylphenyl)butanoyl]pyrrol-2-yl}butan-1-ol 1/2 fumarate (Exemplary compound No. 23)

[Chemical Formula 30]

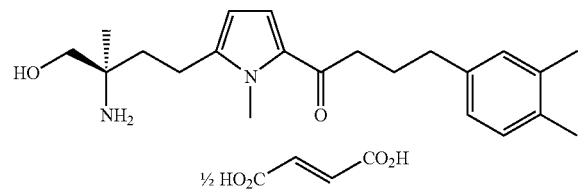

(2R)-1-Acetoxy-2-acetylamino-2-methyl-4-{1-methyl-5-[4-(3,4-dimethylphenyl)-1-(4-(3,4-dimethylphenyl)butanoyloxy)but-1-enyl]pyrrol-2-yl}butane (29.6 g, 48.1 mmol) obtained in Example 2 (2a) was dissolved in a mixture of tetrahydrofuran (100 mL) and methanol (100 mL) and water (100 mL) and lithium hydroxide monohydrate (20.2 g, 481 mmol) were added thereto, followed by stirring of the mixture at 60° C. for 5 hours. After cooling, water and methylene chloride were added to the reaction mixture to separate it. An organic phase was separated and after it was washed with a saturated aqueous NaCl solution, it was dried over anhydrous sodium sulfate. The solvent was evaporated under reduced pressure and the residue was purified by basic silica gel (NH type) chromatography (methylene chloride:methanol, 100:1) to obtain (2R)-2-amino-2-methyl-4-{1-methyl-5-[4-(3,4-dimethylphenyl)butanoyl]pyrrol-2-yl}butan-1-ol (13.2 g, yield: 77%). A solution of fumaric acid (244 g, 2.10 mmol) in methanol (5 mL) was added to a solution of the obtained (2R)-2-amino-2-methyl-4-{1-methyl-5-[4-(3,4-dimethylphenyl)butanoyl]pyrrol-2-yl}butan-1-ol (1.50 g, 4.21 mmol) in methanol (16 mL) under ice-cooling. After methanol was evaporated under reduced pressure, the residue was dissolved in a small amount of methanol, ethyl acetate was added thereto and recrystallization was carried out to obtain a crude crystal (1.51 g) of the title compound. The obtained crude crystal (1.51 g), was subjected again to recrystallization using methanol and ethyl acetate to obtain the title compound (1.23 g, yield: 71%) as a white crystal.

$^1$H NMR (CD$_3$OD, 400 MHz): δ 6.98 (d, 1H, J=7.8 Hz), 6.93 (d, 1H, J=3.9 Hz), 6.91 (s, 1H), 6.86 (d, 1H, J=7.8 Hz), 6.63 (s, 1H), 6.00 (d, 1H, J=4.0 Hz), 3.84 (s, 3H), 3.62 (d, 1H, J=11.3 Hz), 3.53 (d, 1H, J=11.3 Hz), 2.74-2.66 (m, 4H), 2.57 (t, 2H, J=7.4 Hz), 2.21 (s, 3H), 2.21 (s, 3H), 2.06-1.83 (m, 4H), 1.32 (s, 3H);

IR $υ_{max}$ cm$^{-1}$ (KBr): 3276, 2945, 2900, 1645, 1543, 1411, 1355, 1216, 1157, 986, 804, 669, 536;
MS (FAB) m/z : 357 ((M+H)$^+$; free body);
Elementary analysis (% for C$_{22}$H$_{32}$N$_2$O$_2$.0.5(C4H4O4)),
Calculated: C: 69.54, H: 8.27, N: 6.76;
Found: C: 69.40, H: 8.44, N: 6.73.

Reference Example 1

(2R)-1-Acetoxy-2-acetylamino-2-methyl-4-(1-methylpyrrol-2-yl)butane (1a) (2R)-2-t-Butoxycarbonylamino-3-n-hexanoyloxy-2-methyl-1-propanol 2-t-Butoxycarbonylamino-2-methylpropane-1,3-diol (20.0 g, 97.4 mmol) was suspended in isopropyl ether (200 mL), and 16.3 mL (0.100 mol) of vinyl hexanoate and lipase [Immobilized lipase from Pseudomonas sp., manufactured by TOYOBO Co., Inc., 0.67 U/mg] (0.8 g) were added thereto, followed by stirring of the mixture at room temperature for 2 hours. After the reaction mixture was filtered, the filtrate was evaporated under reduced pressure. The residue was purified by silica gel column chromatography (hexane: ethyl acetate, 10:1-2:1) to obtain the title compound (25.0 g, yield: 85%).

The thus obtained (2R)-2-t-butoxycarbonylamino-3-n-hexanoyloxy-2-methyl-1-propanol was analyzed by optical active HPLC column for analysis [ChiralCel OF (0.46 cm×25 cm), manufactured by Daicel Chemical Industries, eluting solvent hexane:2-propanol, 70:30, flow rate 0.5 mL/min] and optical purity (85% ee) was determined. The retention time of 2S form was 8.2 minutes and the retention time of 2R form was 10.5 minutes.

[α]$_D$ –8.5 (c 1.86, CHCl$_3$);
$^1$H NMR (CDCl$_3$, 400 MHz): δ 4.86 (s, 1H) 4.25 (d, 1H, J=11.2 Hz), 4.19 (d, 1H, J=11.2 Hz), 3.86 (br s, 1H), 3.70-3.55 (m, 2H), 2.36 (t, 2H, J=7.4 Hz), 1.44 (s, 9H), 1.40-1.30 (m, 4H), 1.25 (s, 3H), 0.90 (t, 3H, J=7.0 Hz);
IR $υ_{max}$ cm$^{-1}$ (Liquid Film): 3415, 3380, 2961, 2935, 2874, 1721, 1505, 1458, 1392, 1368, 1293, 1248, 1168, 1076;
MS (FAB) m/z: 304 ((M+H)$^+$).

(1b) (2S)-2-t-Butoxycarbonylamino-3-n-hexanoyloxy-2-methyl-1-propanal

Molecular sieve 4A (220 g) and pyridinium chlorochromate (43.6 g, 0.202 mol) were added to a solution of (2R)-2-t-butoxycarbonylamino-3-n-hexanoyloxy-2-methyl-1-propanol (30.7 g, 0.101 mol) obtained in Reference example 1 (1a) in methylene chloride (600 mL) under ice-cooling and the mixture was stirred at room temperature for 2 hours. Ether was added to the reaction mixture, the mixture was filtered and the filtrate was evaporated under reduced pressure. The residue was purified by silica gel chromatography (hexane: ethyl acetate, 10:1-5:1) to obtain the title compound (28.8 g, yield: 95%).

$^1$H NMR (CDCl$_3$, 400 MHz): δ 9.45 (s, 1H), 5.26 (br s, 1H), 4.44 (d, 1H, J=11.2 Hz), 4.32 (d, 1H, J=11.2 Hz), 2.32 (t, 2H, J=7.46 Hz), 1.70-1.55 (m, 2H), 1.45 (s, 9H), 1.38 (s, 3H), 1.40-1.25 (m, 4H), 0.90 (t, 3H, J=7.0 Hz);
IR $υ_{max}$ cm$^{-1}$ (Liquid Film) : 3367, 2961, 2935, 2874, 1742, 1707, 1509, 1458, 1392, 1369, 1290, 1274, 1254, 1166, 1100, 1078;
MS (FAB) m/z: 302 ((M+H)$^+$).

(1c) (1-Methylpyrrol-2-yl)methyltriphenylphosphonium iodide

A mixture of 35% aqueous formaldehyde solution (20.8 mL, 264 mmol) and dimethylamine hydrochloride (22.7 g, 278 mmol) was added to 1-methylpyrrole (21.4 g, 264 mmol) under ice-cooling with stirring over 1 hour and 30 minutes and the mixture was stirred at room temperature for 6 hours. A 10% aqueous sodium hydroxide solution (150 mL) and ether were added to the reaction mixture to separate it. The thus obtained organic phase was separated, washed with a saturated aqueous NaCl solution and dried over anhydrous sodium sulfate. After filtration, the solvent was evaporated under reduced pressure and the residue was purified by silica gel chromatography (methylene chloride:methanol, 10:1) to obtain 2-(N,N-dimethylaminomethyl)-1-methylpyrrol (31.5 g, yield: 86%). Methyl iodide (16.2 mL, 260 mmol) was added to a solution of 2-(N,N-dimethylaminomethyl)-1-methylpyrrol (30.0 g, 217 mmol) in ethanol (220 mL) under ice-cooling and the mixture was stirred at room temperature for 2 hours. Ethyl acetate (220 mL) was added to the reaction mixture, the precipitated crystal was collected by filtration, washed with ethyl acetate and dried to obtain (1-methylpyrrol-2-yl)methyltrimethylammonium iodide (55.3 g, yield: 91%).

(1-Methylpyrrol-2-yl)methyltrimethylammonium iodide (55.3 g, 198 mmol) was suspended in acetonitrile (400 mL) and triphenylphosphine (62.2 g, 237 mmol) was added thereto, followed by stirring of the mixture at 80° C. for 10 hours. After cooling, the mixture was concentrated to about 1/2 under reduced pressure, ethyl acetate (200 mL) was added thereto, and the precipitated crystal was collected by filtration. The crystal was washed with ethyl acetate and dried under reduced pressure to obtain the title compound (77.1 g, yield: 81%).

(1d) (2R)-2-t-Butoxycarbonylamino-1-n-hexanoyloxy-2-methyl-4-(1-methylpyrrol-2-yl)-3-butene (1-Methylpyrrol-2-yl)methyltriphenylphosphonium iodide (58.0 g, 120 mmol) obtained in Reference example 1 (1c) was suspended in tetrahydrofuran (300 mL) and a solution of potassium t-butoxide (13.5 g, 120 mmol) in tetrahydrofuran (180 mL) was added thereto under ice-cooling with stirring over 30 minutes, followed by further stirring of the mixture under ice-cooling for 80 minutes. A solution of (2S)-2-t-butoxycarbonylamino-3-n-hexanoyloxy-2-methyl-1-propanol (30.3 g, 101 mmol) obtained in Reference example 1 (1b) in tetrahydrofuran (120 mL) was added to the reaction mixture over 30 minutes and the mixture was stirred under ice-cooling for 30 minutes. A saturated aqueous ammonium chloride solution was added to the reaction mixture to stop the reaction and the temperature of the liquid was returned to room temperature. The mixture was concentrated under reduced pressure and water and ethyl acetate were added thereto to separate it. The thus obtained organic phase was separated, washed with water and a saturated aqueous NaCl solution and dried over anhydrous sodium sulfate. After filtration, the solvent was evaporated under reduced pressure and the residue was purified by silica gel chromatography (hexane:ethyl acetate, 9:1) to obtain the title compound (37.0 g, yield: 97%).

$^1$H NMR (CDCl$_3$, 400 MHz): δ 6.60 (t, 1H, J=2.3 Hz), 6.57 (t, 1H, J=2.3 Hz), 6.38 (d, 1H, J=16.1 Hz), 6.30-6.26 (m, 2H), 6.27 (d, 1H, J=12.5 Hz), 6.11 (t, 1H, J=3.2 Hz), 6.08 (t, 1H, J=3.2 Hz), 5.99 (d, 1H, J=16.1 Hz), 5.58 (d, 1H, J=12.5 Hz) 5.04 (br s, 1H), 4.81 (br s, 1H), 4.34-4.16 (m, 4H), 3.60 (s, 3H), 3.54 (s, 3H), 2.36-2.30 (m, 4H), 1.67-1.22 (m, 36H), 0.92-0.87 (s, 6H);

MS (EI) m/z: 280(M$^+$), 249, 224, 193 (base), 164, 149, 132, 108, 94, 57.

(1e) (4R)-4-Methyl-4-[2-(1-methylpyrrol-2-yl)ethenyl]-1,3-oxazolidin-2-one (2R)-2-t-butoxycarbonylamino-1-n-hexanoyloxy-2-methyl-4-(1-methylpyrrol-2-yl)-3-butene (37.0 g, 97.8 mmol) obtained in Reference example 1 (1d) was dissolved in a mixture of tetrahydrofuran (100 mL) and methanol (100 mL) and a 2N aqueous sodium hydroxide solution (100 mL) was added thereto, followed by stirring of the mixture at room temperature for 1 hour. Water and methylene chloride were added to the reaction mixture to separate it. The thus obtained organic phase was separated, washed with a saturated aqueous NaCl solution and dried over anhydrous sodium sulfate. After filtration, the solvent was evaporated under reduced pressure to obtain a crude product (28.8 g, yield: quantitative). A solution of potassium t-butoxide (13.2 g, 117 mmol) in tetrahydrofuran (80 mL) was added to a solution of the crude product in tetrahydrofuran (320 mL) under ice-cooling over 10 minutes and the mixture was stirred at the same temperature for 20 minutes. Acetic acid (6.7 mL, 117 mmol) was added to the reaction mixture to neutralize it and the mixture was concentrated under reduced pressure. Water and ethyl acetate were added thereto to separate it. The thus obtained organic phase was separated, washed with a saturated aqueous NaCl solution and dried over anhydrous sodium sulfate. After filtration, the solvent was evaporated under reduced pressure and the residue was purified by silica gel chromatography (hexane:ethyl acetate, 1:1-1:2) to obtain the title compound (20.3 g, yield: quantitative).

$^1$H NMR (CDCl$_3$, 400 MHz): δ 6.67 (t, 1H, J=2.1 Hz), 6.62 (t, 1H, J=1.5 Hz), 6.48 (d, 1H, J=15.7 Hz), 6.36 (dd, 1H, J=3.7, 1.5 Hz), 6.31 (d, 1H, J=12.2 Hz), 6.14-6.10 (m, 2H), 6.07 (br d, 1H, J=3.6 Hz), 5.99 (d, 1H, J=15.7 Hz), 5.65 (d, 1H, J=12.2 Hz), 5.46 (br s, 1H), 5.11 (br s, 1H), 4.31 (d, 1H, J=8.2 Hz), 4.22 (d, 1H, J=8.2 Hz), 4.17 (d, 1H, J=8.2 Hz), 4.16 (d, 1H, J=8.2 Hz), 3.62 (s, 3H), 3.55 (s, 3H), 1.59 (s, 3H), 1.57 (s, 3H);

MS (EI) m/z: 206 (M$^+$, base), 191, 176, 161, 147, 132, 120, 106, 94, 81, 77.

(1f) (4R)-4-Methyl-4-[2-(1-methylpyrrol-2-yl)ethyl-1,3-oxazolidin-2-one

10% Palladium-carbon (2.02 g, 50% hydrous) was suspended in methanol (40 ml) and a solution of (4R)-4-methyl-4-[2-(1-methylpyrrol-2-yl)ethenyl]-1,3-oxazolidin-2-one (20.3 g, 97.8 mmol) obtained in Reference example 1 (1e) in methanol (360 mL) was added thereto, followed by stirring of the mixture under hydrogen atmosphere at room temperature for 60 minutes. After the palladium-carbon in the reaction mixture was Celite-filtered, the filtrate was evaporated under reduced pressure. The residue was purified by silica gel chromatography (hexane:ethyl acetate, 3:2) to obtain the title compound (18.8 g, yield: 88%).

The thus obtained (4R)-4-methyl-4-[2-(1-methylpyrrol-2-yl)ethyl]-1,3-oxazolidin-2-one was analyzed by an optically active HPLC column for analysis [ChiralCel OJ (0.46 cm×25 cm), manufactured by Daicel Chemical Industries, eluting solvent n-hexane:2-propanol, 70:30, flow rate 1.0 mL/min] to determine the optical purity (75% ee). The retention time of 4S form was 12.5 minutes and the retention time of 4R form was 15.5 minutes.

$^1$H NMR (CDCl$_3$, 400 MHz): δ 6.58 (t, 1H, J=2.4 Hz), 6.05 (dd, 1H, J=3.2 Hz, 2.4 Hz), 5.88 (br d, 1H, J=3.2 Hz), 5.15 (br s, 1H), 4.14 (d, 1H, J=8.3 Hz), 4.07 (d, 1H, J=8.3 Hz), 2.70-2.58 (m, 2H), 2.00-1.87 (m, 2H), 1.42 (s, 3H);

IR υ$_{max}$ cm$^{-1}$ (KBr): 3289, 3103, 2977, 2938, 1759, 1713, 1495, 1397, 1381, 1309, 1281, 1231, 1032, 945, 928, 776, 718, 706, 656;

MS (EI) m/z: 208 (M$^+$), 108 (base), 94, 81, 56, 42.

(1g) (2R)-2-Amino-2-methyl-4-(1-methylpyrrol-2-yl)butan-1-ol 1/2D-(−)-tartrate (4R)-4-Methyl-4-[2-(1-methylpyrrol-2-yl)ethyl]-1,3-oxazolidin-2-one (17.9 g, 86.0 mmol) obtained in Reference example 1 (1f) was dissolved in a mixture of tetrahydrofuran (250 mL) and methanol (125 mL) and a 5N aqueous potassium hydroxide solution (125 mL) was added thereto, followed by heating under reflux of the mixture for 4 days. After cooling, water and methylene chloride were added to the reaction mixture to separate it. The thus obtained organic phase was separated and dried over anhydrous sodium sulfate. After filtration, the solvent was evaporated under reduced-pressure and the residue was dissolved in ethanol (260 mL). D-(−)-tartaric acid (6.45 g, 43.0 mmol) was added thereto and the mixture was stirred for 2 hours. The precipitated crystal was collected by filtration to obtain a crude crystal (20.7 g). The crude crystal (18.7 g) was recrystallized from a mixture of ethanol (370 mL) and water (37 mL) and the thus obtained crystal was recrystallized again from a mixture of ethanol (300 mL) and water (30 mL). Further, the obtained crystal was recrystallized again from a mixture of ethanol (240 mL) and water (24 mL) to obtain the title compound (10.5 g, yield: 53%) as a colourless scaly crystal.

The optical purity of the obtained title compound was determined as shown below.

The obtained (2R)-2-amino-2-methyl-4-(1-methylpyrrol-2-yl)butan-1-ol 1/2 D-(−)-tartrate (41.4 mg, 0.16 mmol) was suspended in methylene chloride (1.6 mL) and di-t-butyl dicarbonate (0.176 g, 0.810 mmol), triethylamine (0.225 mL, 1.62 mmol) and 4-dimethylaminopyridine (2.0 mg, 0.016 mmol) were added thereto, followed by stirring of the mixture at room temperature for 30 minutes. The solvent was evaporated under reduced pressure and the residue was purified by silica gel chromatography (hexane:ethyl acetate 3:2-2:1) to obtain (4R)-4-methyl-4-[2-(1-methylpyrrol-2-yl)ethyl]-1,3-oxazolidin-2-one (17.7 mg, yield: 53%).

The thus obtained (4R)-4-methyl-4-[2-(1-methylpyrrol-2-yl)ethyl]-1,3-oxazolidin-2-one was analyzed by an optically active HPLC column for analysis [ChiralCel OJ (0.46 cm×25 cm), manufactured by Daicel Chemical Industries, eluting solvent n-hexane:2-propanol, 70:30, flow rate 1.0 mL/min] similarly to Reference example (1f) to determine the optical purity (99.7% ee).

Mp: 198-199° C.;
[α]$_D$ −13.3 (c 1.00, H$_2$O)
$^1$H NMR (CD$_3$OD, 400 MHz): δ 6.54 (t, 1H, J=2.3 Hz), 5.91 (dd, 1H, J=3.7 Hz, 2.3 Hz), 5.82 (br d, 1H, J=3.7 Hz), 4.32 (s, 1H), 3.61 (d, 1H, J=11.3 Hz), 3.55 (s, 3H), 3.54 (d, 1H, J=11.3 Hz), 2.69-2.57 (m, 2H), 1.97 (ddd, 1H, J=13.8, 9.4, 7.6 Hz), 1.88 (ddd, 1H, J=13.8, 11.0, 6.3 Hz), 1.28 (s, 3H);
IR υ$_{max}$ cm$^{-1}$ (KBr): 3480, 3430, 2926, 2634, 2545, 1586, 1516, 1389, 1359, 1309, 1291, 1105, 1039, 710, 690;
MS (FAB) m/z: 183 ((M+H)$^+$; free body);
Elementary analysis (% for C$_{10}$H$_{18}$N$_2$O.1/2C$_4$H$_6$O$_6$)
Calculated: C: 56.01, H: 8.23, N: 10.89;
Found: C: 55.81, H: 8.22, N: 10.89.

(1h) (2R)-1-Acetoxy-2-acetylamino-2-methyl-4-(1-methylpyrrol-2-yl)butane (2R)-2-Amino-2-methyl-4-(1-methylpyrrol-2-yl)butan-1-ol 1/2 D-(−)-tartrate (3.98 g, 15.5 mmol) obtained in Reference example 1 (1 g) was suspended in a mixture of methylene chloride (50 mL) and water (12.5 mL) and an aqueous sodium hydroxide solution (3.20 g of 97% sodium hydroxide was dissolved in 12.5 mL of water) was added thereto, followed by stirring of the mixture at room temperature for 20 minutes. Methylene chloride was added to the reaction mixture to separate it. The thus obtained organic phase was separated and dried over anhydrous sodium sulfate. After filtration, the solvent was evaporated under reduced pressure and the residue was dissolved in methylene chloride (78 mL). Triethylamine (21.5 mL, 155 mmol), acetic anhydride (7.30 mL, 77.4 mmol) and 4-dimethylaminopyridine (0.189 g, 1.55 mmol) were added thereto and the mixture was stirred at room temperature for 1 hour. Methanol was added thereto to stop the reaction and the solvent was evaporated under reduced pressure. Ethyl acetate and water were added to the residue to separate it. The thus obtained organic phase was separated, washed with water, a saturated aqueous sodium hydrogencarbonate solution and a saturated aqueous NaCl solution and dried over anhydrous sodium sulfate. After filtration, the solvent was evaporated under reduced pressure and the residue was purified by silica gel chromatography (ethyl acetate) to obtain the title compound (4.23 g, yield: quantitative).

$^1$H NMR (CDCl$_3$, 400 MHz): δ 6.54 (t, 1H, J=2.4 Hz), 6.04 (t, 1H, J=2.4 Hz), 5.88 (d, 1H, J=2.4 Hz), 5.39 (br s, 1H), 4.33 (d, 1H, J=11.2 Hz), 4.20 (d, 1H, J=11.2 Hz), 2.60-2.51 (m, 2H), 2.26-2.19 (m, 1H), 2.09 (s, 3H), 1.97-1.89 (m, 4H), 1.38 (s, 3H);
MS (FAB) m/z: 267 ((M+H)$^+$), 266 (M$^+$)

Reference example 2

(2R)-1-Acetoxy-2-acetylamino-2-ethyl-4-(1-methylpyrrol-2-yl)butane (2a) (2R)-2-t-Butoxycarbonylamino-2-ethyl-3-n-hexanoyloxy-1-propanol 2-t-Butoxycarbonylamino-2-ethylpropane-1,3-diol (52.9 g, 241 mmol) was suspended in isopropyl ether (1.0 L) and vinyl hexanoate (41.0 mL, 254 mmol) and lipase [Immobilized lipase from *Pseudomonas* sp., manufactured by TOYOBO Limited, 0.67 U/mg] (2.1 g) was added thereto, followed by stirring of the mixture at room temperature for 4 hours. After the reaction mixture was filtered, the filtrate was evaporated under reduced pressure. The residue was purified by silica gel column chromatography (hexane:ethyl acetate, 7:1-4:1-2:1) to obtain the title compound (66.8 g, yield: 87%).

The thus obtained (2R)-2-t-butoxycarbonylamino-2-ethyl-3-n-hexanoyloxy-1-propanol was analyzed by an optically active HPLC column for analysis [ChiralCel OF (0.46 cm×25 cm), manufactured by Daicel Chemical Industries, eluting solvent hexane:2-propanol, 80:20, flow rate 0.5 mL/min] to determine the optical purity (93% ee). The retention time of 2S form was 7.4 minutes and the retention time of 2R form was 7.9 minutes.

$^1$H NMR (CDCl$_3$, 400 MHz): δ 4.76 (br s, 1H), 4.24 (d, 1H, J=11.0 Hz), 4.10 (d, 1H, J=11.0 Hz), 3.65-3.62 (m, 2H) 2.35 (t, 2H, J=7.7 Hz), 1.78-1.69 (m, 1H), 1.63-1.53 (m, 4H), 1.44 (s, 9H), 1.30-1.25 (m, 4H), 0.87-0.83 (m, 6H);
MS (FAB) m/z: 340 ((M+Na)$^+$), 318 ((M+H)$^+$)

(2b) (2S)-2-t-Butoxycarbonylamino-2-ethyl-3-n-hexanoyloxy-1-propanol

Molecular sieve 4A (117 g) and pyridinium dichromate (117 g, 311 mmol) were added to a solution of (2R)-2-t-butoxycarbonylamino-2-ethyl-3-n-hexanoyloxy-1-propanol (66.7 g, 210 mmol) obtained in Reference example 2 (2a) in methylene chloride (700 mL) under ice-cooling and the mixture was stirred at room temperature for 2 hours. Ether was added to the reaction mixture and the mixture was filtered. The filtrate was evaporated under reduced pressure and the residue was purified by silica gel chromatography (hexane:ethyl acetate, 10:1-5:1) to obtain the title compound (45.9 g, yield: 69%).

$^1$H NMR (CDCl$_3$, 400 MHz): δ 9.34, (s, 1H), 5.30 (br s, 1H), 4.60 (d, 1H, J=11.4 Hz), 4.40 (d, 1H, J=11.4 Hz), 2.28 (t,

2H, J=7.3 Hz), 2.18-2.06 (m, 1H), 1.79-1.69 (m, 1H), 1.62-1.55 (m, 2H), 1.44 (s, 9H), 1.34-1.22 (m, 4H), 0.90 (t, 3H, J=7.3 Hz), 0.81 (t, 3H, J=7.3 Hz);
MS (FAB) m/z: 338 ((M+Na)$^+$), 316 ((M+H)$^+$)

(2c) (2R)-2-t-Butoxycarbonylamino-2-ethyl-1-n-hexanoyloxy-4-(1-methylpyrrol-2-yl)-3-butene The reaction was carried out in the similar manner to Reference example 1 (1d) using (1-methylpyrrol-2-yl)methyltriphenylphosphonium iodide obtained in Reference example 1 (1c) and (2S)-2-t-butoxycarbonylamino-3-n-hexanoyloxy-2-ethyl-1-propanal obtained in Reference example 2 (2b) as starting materials to obtain the title compound (yield: 69%).
$^1$H NMR (CDCl$_3$, 400 MHz): δ 6.61-6.54 (m, 1H), 6.39-6.21 (m, 2H), 6.13-6.05 (m, 1H), 5.89-5.37 (m, 1H), 4.39-4.20 (m, 2H), 3.65-3.52 (m, 3H), 2.31 (t, 2H, J=7.3 Hz), 1.99-1.23 (m, 17H), 0.97-0.85 (t, 6H, J=7.3 Hz);
MS (FAB) m/z: 392 (M$^+$)

(2d) (4R)-4-Ethyl-4-[2-(1-methylpyrrol-2-yl)ethenyl]-1,3-oxazolidin-2-one

The reaction was carried out in the similar manner to Reference example 1 (1e) using (2R)-2-t-butoxycarbonylamino-2-ethyl-1-n-hexanoyloxy-4-(1-methylpyrrol-2-yl)-3-butene obtained in Reference example 2 (2c) as a starting material to obtain the title compound (yield: 74%).
$^1$H NMR (CDCl$_3$, 400 MHz): δ 6.66-6.57 (m, 1H), 6.48 (d, 1H, J=15.7 Hz), 6.35-6.30 (m, 1H), 6.12-6.05 (m, 1H), 5.90 (d, 1H, J=15.7 Hz), 4.30-4.15 (m, 2H,) 3.55-3.50 (m, total 3H), 1.90-1.72 (m, 2H), 0.95-1.05 (m, 3H);
MS (EI) m/z: 220 (M$^+$).

(2e) (4R)-4-Ethyl-4-[2-(1-methylpyrrol-2-yl)ethyl]-1,3-oxazolidin-2-one

The reaction was carried out in the similar manner to Reference example 1 (1f) using (4R)-4-ethyl-4-[2-(1-methylpyrrol-2-yl)ethenyl]-1,3-oxazolidin-2-one obtained in Reference example 2 (2d) as a starting material to obtain the title compound (yield: 96%). The thus obtained (4R)-4-ethyl-4-[2-(1-methylpyrrol-2-yl)ethyl]-1,3-oxazolidin-2-one was analyzed by an optically active HPLC column for analysis [ChiralCel OJ-H (0.46 cm×25 cm), manufactured by Daicel Chemical Industries, eluting solvent n-hexane:2-propanol, 60:40, flow rate 1.0 mL/min] to determine the optical purity (94% ee). The retention time of 2S form was 8.5 minutes and the retention time of 2R form was 11.3 minutes.
$^1$H NMR (CDCl$_3$, 400 MHz): δ 6.58 (t, 1H, J=2.4 Hz), 6.06 (dd, 1H, J=3.2 Hz, 2.4 Hz), 5.88 (m, 1H), 4.15 (d, 1H, J=8.8 Hz), 4.10 (d, 1H, J=8.8 Hz), 3.54 (s, 3H), 2.63-2.59 (m, 2H), 1.96-1.91 (m, 2H), 1.75-1.56 (m, 2H), 0.98 (t, 3H, J=7.3Hz),
IR $υ_{max}$ cm$^{-1}$ (liquid film): 3270, 2969, 2938, 1748, 1495, 1400, 1302, 1271, 1049, 709;
MS (EI) m/z: 222 (M$^+$)

(2f) (2R)-1-Acetoxy-2-acetylamino-2-ethyl-4-(1-methylpyrrol-2-yl)butane

The reaction was carried out in the similar manner to Reference example 1 (1 g) and (1h) using (4R)-4-ethyl-4-[2-(1-methylpyrrol-2-yl)ethyl]-1,3-oxazolidin-2-one obtained Reference example 2 (2e) as a starting material to obtain the title compound (yield: 77%).
$^1$H NMR (CDCl$_3$, 400 MHz): δ 6.54 (t, 1H, J=2.4 Hz), 6.04 (t, 1H, J=2.4 Hz), 5.89-5.87 (m, 1H), 4.32 (s, 2H), 3.53 (s, 3H), 2.52 (dd, 2H, J=8.8, 8.3Hz), 2.17-1.72 (m, 4H), 2.08 (s, 3H), 1.94 (s, 3H), 0.88 (t, 3H, J=7.3Hz);
MS (FAB) m/z: 281 ((M+H)$^+$).

Reference Example 3

(2R)-1-Acetoxy-2-acetylamino-2-methyl-4-(1-ethylpyrrol-2-yl)butane (3a)
(1-Ethylpyrrol-2-yl)methyltriphenylphosphonium iodide A mixture of a 35% aqueous formaldehyde solution (9.0 mL, 105 mmol) and dimethylamine hydrochloride (9.0 g, 110 mmol) was added to 1-ethylpyrrol (10.0 g, 105 mmol) under ice-cooling with stirring over 1 hour and 30 minutes and the mixture was stirred at room temperature for 6 hours. A 10% aqueous sodium hydroxide solution (150 mL) and ether were added to the reaction mixture to separate it. The thus obtained organic phase was separated, washed with a saturated aqueous NaCl solution and dried over anhydrous sodium sulfate. After filtration, the solvent was evaporated under reduced pressure and the residue was purified by silica gel chromatography (methylene chloride:methanol, 9:1) to obtain 2-(N,N-dimethylaminomethyl)-1-ethylpyrrol (15.6 9, yield: 97%).
Methyl iodide (7.7 mL, 124 mmol) was added to a solution of 2-(N,N-dimethylaminomethyl)-1-ethylpyrrol (15.6 g, 102 mmol) in ethanol (150 mL) under ice-cooling and the mixture was stirred at room temperature for 3 hours. Ethyl acetate (150 mL) was added to the reaction mixture and the precipitated crystal was collected by filtration. After the crystal was washed with ethyl acetate and dried to obtain (1-ethylpyrrol-2-yl)methyltrimethylammonium iodide (20.0 g, yield: 66%).
(1-Ethylpyrrol-2-yl)methyltrimethylammonium iodide (20.0 g, 68.0 mmol) was suspended in acetonitrile (200 mL) and triphenylphosphine (22.0 g, 83.9 mmol) was added thereto, followed by stirring of the mixture at 80° C. for 9 hours. After cooling, the mixture was concentrated to about ½ under reduced pressure and ethyl acetate (100 mL) was added thereto. The precipitated crystal was collected by filtration, washed with ethyl acetate and dried under reduced pressure to obtain the title compound (27.5 g, yield: 81%).
$^1$H NMR (CDCl$_3$, 400 MHz): δ 7.94-7.89 (m, 3H), 7.78-7.71 (m, 6H), 7.64-7.57 (m, 6H), 6.82-6.79 (m, 1H), 5.96-5.92 (m, 1H), 5.51-5.47 (m, 1H), 5.10 (d, 2H, J=13.9Hz), 3.35 (q, 2H, J=7.3 Hz), 0.96 (t, 3H, J=7.3 Hz).

(3b) (2R)-2-t-Butoxycarbonylamino-2-methyl-4-(1-ethylpyrrol-2-yl)-1-n-hexanoyloxy-3-butene (1-Ethylpyrrol-2-yl)methyltriphenylphosphonium iodide (19.8 g, 39.8 mmol) obtained in Reference example 3 (3a) was suspended in tetrahydrofuran,(100 mL) and a solution of potassium t-butoxide (4.47 g, 39.8 mmol) in tetrahydrofuran (70 mL) was added thereto under ice-cooling with stirring over 30 minutes, followed by further stirring of the mixture under ice-cooling for 1 hour and 30 minutes. Then, a solution of (2S)-2-t-butoxycarbonylamino-1-n-hexanoyloxy-2-methyl-3-propanal (10.0 g, 33.2 mmol) obtained in Reference example 1 (1b) in tetrahydrofuran (50 mL) was added to the mixture over 30 minutes and the mixture was stirred under ice-cooling for 1 hour and 30 minutes. A saturated aqueous ammonium chloride solution was added to the reaction mixture to stop the reaction and the temperature of the mixture was returned to room temperature. The mixture was concentrated under reduced pressure and water and ethyl acetate were added thereto to separate it. The thus obtained organic phase was separated, washed with water and a saturated aqueous NaCl solution and dried over anhydrous sodium sulfate. After filtration, the solvent was evaporated under reduced pressure and the residue was purified by silica gel chromatography (hexane:ethyl acetate, 4:1) to obtain the title compound (11.7 g, yield: 90%).

$^1$H NMR (CDCl$_3$, 400 MHz): δ 6.67-6.62 (m, 2H), 6.42-6.36 (m, 1H,), 6.31-6.26 (m, 3H), 6.13-6.08 (m, 2H), 6.02-5.96 (m, 1H), 5.63-5.58 (m, 1H), 4.35-4.08 (m, 4H), 3.96-3.86 (m, 4H), 2.85-2.81 (m, 4H), 1.67-1.58 (m, 4H), 1.48-1.24 (m, 38H), 0.93-0.86 (m, 6H).

(3c) (4R)-4-Methyl-4-[2-(1-ethylpyrrol-2-yl)ethenyl]-1,3-oxazolidin-2-one (2R)-2-t-Butoxycarbonylamino-2-methyl-4-(1-ethylpyrrol-2-yl)-1-n-hexanoyloxy-3-butene (11.7 g, 29.8 mmol) obtained in Reference example 3 (3b) was dissolved in a mixture of tetrahydrofuran (40 mL) and methanol (40 mL) and a 2N aqueous sodium hydroxide solution (40 mL) was added thereto, followed by stirring of the mixture at room temperature for 1 hour and 30 minutes. Acetic acid (1.5 mL) was added to the reaction mixture to stop the reaction and water and ethyl acetate were added thereto to separate it. The thus obtained organic phase was separated, washed with water and a saturated aqueous NaCl solution and dried over anhydrous sodium sulfate. After filtration, the solvent was evaporated under reduced pressure to obtain a crude product (8.7 g). A solution of potassium t-butoxide (4.0 g, 35.6 mmol) in tetrahydrofuran (30 mL) was added to a solution of the crude product (8.7 g) in tetrahydrofuran (100 mL) under ice-cooling over 10 minutes, followed by stirring of the mixture at the same temperature for 1 hour. Acetic acid (2 mL) was added to the reaction mixture to neutralize it, and the mixture was concentrated under reduced pressure and water and ethyl acetate were added thereto to separate it. The thus obtained organic phase was washed with a saturated aqueous NaCl solution and dried over anhydrous sodium sulfate. After filtration, the solvent was evaporated under reduced pressure and the residue was purified by silica gel chromatography (hexane:ethyl acetate, 3:2) to obtain the title compound (5.7 g, yield: 86%).

$^1$H NMR (CDCl$_3$, 400 MHz): δ 6.73-6.65 (m, 2H), 6.52-6.46 (m, .1H,), 6.36-6.29 (m, 2H), 6.15-6.10 (m, 2H), 6.05-5.97 (m, 2H), 5.69-5.65 (m, 2H), 4.31-4.09 (m, 4H), 3.97-3.83 (m, 4H), 1.60-1.53 (m, 6H), 1.39-1.31 (m, 6H).

(3d) (4R)-4-Methyl-4-[2-(1-ethylpyrrol-2-yl)ethyl]-1,3-oxazolidin-2-one

10% Palladium-carbon (500 mg, 50% hydrous) was suspended in ethanol (10 mL) and a solution of (4R)-4-methyl-4-[2-(1-ethylpyrrol-2-yl)ethenyl]-1,3-oxazolidin-2-one (5.7 g, 25.9 mmol) obtained in Reference example 3 (3c) in ethanol (50 mL) was added thereto, followed by stirring of the mixture at room temperature under a hydrogen atmosphere for 1 hour. After the palladium-carbon in the reaction mixture was Celite-filtered, the filtrate was evaporated under reduced pressure. The residue was purified by silica gel chromatography (hexane: ethyl acetate, 3:7) to obtain the title compound (5.0 g, yield: 87%).

The thus obtained (4R)-4-methyl-4-[2-(1-ethylpyrrol-2-yl)ethyl]-1,3-oxazolidin-2-one was analyzed by an optically active HPLC column for analysis (ChiralPak OJ (0.46 cm×25 cm), manufactured by Daicel Chemical Industries, eluting solvent n-hexane:2-propanol, 70:30, flow rate 1.0 mL/min] to determine the optical purity (84% ee). The retention time of 4S form was 7.5 minutes and the retention time of 4R form was 8.3 minutes.

$^1$H NMR (CDCl$_3$, 400 MHz): δ 6.66-6.63 (m, 1H), 6.10-6.07 (m, 1H), 5.B9-5.86 (m, 1H), 5.00 (br s, 1H), 4.15 (d, 1H, J=8.1 Hz), 4.08 (d, 1H, J=8.1 Hz), 3.84 (q, 2H, J=7.3 Hz), 2.67-2.61 (m, 2H), 1.99-1.92 (m, 2H), 1.43 (s, 3H), 1.87 (t, 3H, J=7.3 Hz).

(3e) (2R)-2-Amino-2-methyl-4-(1-ethylpyrrol-2-yl) butan-1-ol ½ D-(−)-tartrate (4R)-4-Methyl-4-[2-(1-ethylpyrrol-2-yl)ethyl]-1,3-oxazolidin-2-one (4.90 g, 22.0 mmol) obtained in Reference example 3 (3d) was dissolved in a mixture of tetrahydrofuran (80 mL) and methanol (40 mL) and a 5.5 N aqueous potassium hydroxide solution (40 mL) was added thereto, followed by heating under reflux of the mixture for 4 days. After cooling, water and methylene chloride were added to the reaction mixture to separate it. The thus obtained organic phase was separated and dried over anhydrous sodium sulfate. After filtration, the solvent was evaporated under reduced pressure and the residue was dissolved in 200 mL of ethanol. After a solution of D-(−)-tartrate (1.59 g, 10.5 mmol) in ethanol (20 mL) was added thereto and the mixture was left to stand for 4 hours, the precipitated crude crystal was recrystallized from a mixture of ethanol (100 mL) and water (10 mL). The obtained crystal was recrystallized again from a mixture of ethanol (50 mL) and water (5 mL) to obtain the title compound (2.80 g, yield: 37%) as a colourless plate-like crystal.

The thus obtained (2R)-2-amino-2-methyl-4-(1-ethylpyrrol-2-yl)butan-1-ol ½ D-(−)-tartrate (55.5 mg, 0.160 mmol) was suspended in methylene chloride (1.6 mL) and di-t-butyl dicarbonate (0.17 g, 0.78 mmol), triethylamine (0.22 mL, 1.58 mmol) and 4-dimethylaminopyridine (3.0 mg, 0.025 mmol) were added thereto, followed by stirring of the mixture at room temperature for 20 minutes. Water and ethyl acetate were added thereto to separate it. The thus obtained organic phase was separated and dried over anhydrous sodium sulfate. The solvent was evaporated under reduced pressure and the residue was purified by silica gel chromatography (hexane:ethyl acetate, 1:1) to obtain (4R)-4-methyl-4-[2-(1-ethylpyrrol-2-yl)ethyl]-1,3-oxazolidin-2-one (18.0 mg, yield: 58%).

The thus obtained (4R)-4-methyl-4-[2-(1-ethylpyrrol-2-yl)ethyl]-1,3-oxazolidin-2-one was analyzed by an optically active HPLC column for analysis [ChiralPak OJ (0.46 cm×25 cm), manufactured by Daicel Chemical Industries, eluting solvent n-hexane:2-propanol, 70:30, flow rate 1.0 mL/min] to determine the optical purity (99.9% ee).

$^1$H NMR (DMSO-d$_6$, 400 MHz): δ 6.58-6.54 (m, 1H), 5.93-5.89 (m, 1H), 5.79-5.76 (m, 1H), 4.27 (s, 1H), 3.85 (q, 2H, J=7.3 Hz), 3.68 (d, 1H, J=11.7 Hz), 3.51 (d, 1H, J=11.7 Hz), 2.62-2.56 (m, 2H), 1.99-1.82 (m, 2H), 1.29 (t, 3H, J=7.3 Hz), 1.27 (s, 3H).

(3f) (2R)-1-Acetoxy-2-acetylamino-2-methyl-4-(1-ethylpyrrol-2-yl)butane

Triethylamine (17.0 mL, 122 mmol), acetic anhydride (7.6 mL, 80.4 mmol) and 4-dimethylaminopyridine (20 mg, 0.16 mmol) were added to a solution of (2R)-2-amino-2-methyl-4-(1-ethylpyrrol-2-yl)butan-1-ol ½ D-(−)-tartrate (2.70 g, 7.80 mmol) obtained in Reference example 3 (3e) in methylene chloride (30 mL) and the mixture was stirred at room temperature for 3 hours and 30 minutes. Water and methylene chloride were added to the reaction mixture to separate it. The thus obtained organic phase was separated, washed with water and a saturated aqueous NaCl solution and dried over anhydrous sodium sulfate. After filtration, it was concentrated to dryness under reduced pressure and the residue was purified by silica gel chromatography (ethyl acetate) to obtain the title compound (2.2 g, yield: 96%).

$^1$H NMR (CDCl$_3$, 400 MHz): δ 6.62-6.59 (m, 1H), 6.09-6.06 (m, 1H), 5.89-5.87 (m, 1H), 5.41 (br s, 1H), 4.34 (d, 1H, J=11.0 Hz), 4.21 (d, 1H, J=11.0 Hz), 3.85 (q, 2H, J=7.3 Hz), 2.60-2.51 (m, 2H), 2.26-2.18 (m, 1H), 2.08 (s, 3H), 1.98-1.93 (m, 1H), 1.92(s, 3H), 1.38 (s, 3H), 1.37 (t, 3H, J=7.3 Hz).

Reference Example 4

4-(3,4-Dimethylphenyl)butyric acid

[2-(1,3-Dioxolan-2-yl)ethyl]triphenylphosphonium bromide (99.2 g, 224 inmol) was suspended in tetrahydrofuran (200 mL) and a solution of potassium t-butoxide (25.1 g, 224 mmol) in tetrahydrofuran (200 mL) was added thereto under nitrogen atmosphere over 30 minutes, followed by stirring of the mixture under ice-cooling for 30 minutes. A solution of 3,4-dimethylbenzaldehyde (20.2 g, 151 mmol) in tetrahydrofuran (100 mL) was added thereto over 20 minutes and the mixture was stirred under ice-cooling for 20 minutes. A saturated aqueous ammonium chloride solution and ethyl acetate were added to the reaction mixture to separate it. The thus obtained organic phase was separated, washed with water and a saturated aqueous NaCl solution and dried over anhydrous magnesium sulfate. After filtration, the solvent was evaporated under reduced pressure and the residue was purified by silica gel chromatography (hexane:ethyl acetate, 15:1-10:1) to obtain a crude product (29.9 g). 10% Palladium-carbon (3.01 g, 50% hydrous) was added to a solution of the obtained crude product (29.9 g) in methanol (300 mL) and the mixture was stirred at room temperature under hydrogen atmosphere for 2 hours. After the palladium-carbon in the reaction mixture was Celite-filtered, the filtrate was evaporated under reduced pressure. The residue was purified by silica gel chromatography (hexane:ethyl acetate, 10:1) to obtain [1-(1,3-dioxolan-2-yl)-3-(3,4-dimethylphenyl)propane (29.6 g, yield: 98%). Water (250 mL) -was added to a solution of the obtained [1-(1,3-dioxolan-2-yl)-3-(3,4-dimethylphenyl)]propane (29.6 g, 134.4 mmol) in tetrahydrofuran (250 mL) and OXONE™ (248 g, 403 mmol) was added thereto with stirring at room temperature over 20 minutes, followed by stirring of the mixture at room temperature for 18 hours. The insolubles were separated by filtration and a 1N aqueous sodium hydroxide solution was added thereto to bring the pH to 11. Ether was added thereto to separate it. A 1N aqueous hydrochloric acid solution was added to an aqueous phase to bring the pH to 2 and ethyl acetate was added thereto to separate it. The thus obtained organic phase was separated, washed with water and a saturated aqueous NaCl solution and dried over anhydrous magnesium sulfate. After filtration, the solvent was evaporated under reduced pressure to obtain the title compound (26.1 g, yield: 98%).

Reference example 5

4-(2,3-Dimethylphenyl)butyric acid

The reaction was carried out in the similar manner to Reference example 4 using 2,3-dimethylbenzaldehyde to obtain the title compound (yield: 87%).

Reference example 6

4-(2,4-Dimethylphenyl)butyric acid (2-Carboxyethyl)triphenylphosphonium bromide (150 g, 361 mmol) was suspended in tetrahydrofuran (500 mL) and 2,4-dimethylbenzaldehyde (55.4 mL, 397 mmol) was added thereto. A solution of potassium t-butoxide (81.1 g, 722 mmol) in tetrahydrofuran (300 mL) was added thereto under nitrogen atmosphere over 10 minutes and the mixture was stirred under ice-cooling for 3 hours. Water was added to the reaction mixture to stop the reaction and the temperature of the liquid was returned to room temperature. The mixture was concentrated under reduced pressure, a 8N aqueous sodium hydroxide solution was added thereto to bring pH to 11 and ether was added thereto to separate it. A 12N aqueous hydrochloric acid solution was added to an aqueous phase to bring pH to 2 and ethyl acetate was added thereto to separate it. The thus obtained organic phase was separated, washed with water and a saturated aqueous NaCl solution and dried over anhydrous magnesium sulfate. After filtration, the solvent was evaporated under reduced pressure and the residue was purified by silica gel chromatography (hexane:ethyl acetate, 10:1-6:1) to obtain 4-(2,4-dimethylphenyl)-3-butenoic acid (37.0 g, yield: 54%). 10% Palladium-carbon (7.96 g, 50% hydrous) was added to a solution of the obtained 4-(2,4-dimethylphenyl)-3-butenoic acid (37.0 g, 195 mmol) in methanol (400 mL) and the mixture was stirred at room temperature under a hydrogen atmosphere for 3 hours. After the palladium-carbon in the reaction mixture was Celite-filtered, the filtrate was evaporated under reduced pressure. The residue was purified by silica gel chromatography (hexane:ethyl acetate, 10:1) to obtain the title compound (64.4 g, yield: 84%).

Reference Example 7

4-(4-t-Butylphenyl)butyric acid

The reaction was carried out in the similar manner to Reference example 4 using 4-t-butylbenzaldehyde to obtain the title compound (yield: 85%).

Reference Example 8

4-(4-Isopropylphenyl)butyric acid

The reaction was carried out in the similar manner to Reference example 6 using 4-isopropylbenzaldehyde to obtain the title compound (yield: 34%).

Reference Example 9

4-(4-Cyclopropylphenyl)butyric acid

Bromine (12.5 mL, 244 mmol) was dropwise added to a solution of cyclopropylbenzene (25.0 g, 212 mmol) in chloroform (430 mL) with stirring at −78° C. and the mixture was stirred for 45 minutes. A 10% aqueous sodium sulfite solution and water were added to the reaction mixture at −780° C. and chloroform was added thereto to separate it. The thus obtained organic phase was separated, washed with a saturated aqueous NaCl solution and dried over anhydrous magnesium sulfate. After filtration, the solvent was evaporated under reduced pressure and the residue was purified by silica gel chromatography (hexane) to obtain 1-bromo-4-cyclopropylbenzene (35.5 g, yield: 85%). Tetrakis-(triphenylphosphine)palladium (5.33 g, 4.61 mmol) and 3-butyn-1-ol (31.5 g, 450 mmol) were added to a solution of the obtained 1-bromo-4-cyclopropylbenzene (35.5 g, 180 mol) in piperidine (345 mL) and the mixture was stirred at 80° C. under nitrogen atmosphere for 3 hours. The reaction mixture was evaporated under reduced pressure and ethyl acetate and a 1N aqueous hydrochloric acid solution were added to the residue to separate it. The thus obtained organic phase was separated, washed with a 1N aqueous hydrochloric acid solution, a saturated aqueous sodium hydrogencarbonate solution and a saturated aqueous NaCl solution and dried over anhydrous magnesium sulfate. After filtration, the solvent was evaporated under reduced pressure and the residue was purified by silica gel chromatography (hexane:ethyl acetate, 4:1-3:1) to obtain 4-(4-cyclopropylphenyl)but-3-yn-1-ol (30.2 g, yield: 90%). A 6N aqueous sulfuric acid solution (250 mL) was added to a solution of the obtained 4-(4-cyclopropylphenyl)but-3-yn-1-ol (27.8 g, 149 mmol) in methanol (300 mL) and the mixture was heated under reflux for 6 hours. After it was left to stand, methanol of the reaction mixture was evaporated under-reduced pressure and ethyl acetate was added thereto to separate it. The thus obtained organic phase was separated, washed with a saturated aqueous NaCl solution and dried over anhydrous magnesium sulfate. After filtration, the solvent was evaporated under reduced pressure. The thus obtained residue was purified by silica gel chromatography (hexane:ethyl acetate, 4:1-2:1) to obtain 1-(4-cyclopropylphenyl)-4-hydroxybutan-1-one (18.7 g, yield: 61%). Hydrazine monohydrate (10.4 mL) and potassium hydroxide (14.4 g) were added to a solution of the obtained 1-(4-cyclopropylphenyl)-4-hydroxybutan-1-one (17.5 g, 85.8 mmol) in ethylene glycol (90 mL) and the mixture was heated under reflux at 180° C. for 6 hours. Water was added to the reaction mixture to dilute it and ethyl acetate was added thereto to separate it. The thus obtained organic phase was separated, washed with a saturated aqueous NaCl solution and dried over anhydrous magnesium sulfate. After filtration, the solvent was evaporated under reduced pressure and the obtained residue was purified by silica gel chromatography (hexane:ethyl acetate, 5:1-3:1) to obtain 4-(4-cyclopropylphenyl)butan-1-ol (15.8 g, yield: 97%). TEMPO (2,2,6,6-tetramethylpiperidine 1-oxyl free radical) (905 mg, 5.79 mmol) and a sodium hydrogenphosphate buffer solution (300 mL, 0.67M, pH 6.7) were added to a solution of the obtained 4-(4-cyclopropylphenyl)butan-1-ol (15.7 g, 83.0 mmol) in acetonitrile (300 mL) and the mixture was stirred at 35° C. for 10 minutes. After an aqueous sodium chlorite solution (16.4 g, water 80 mL) was added to the reaction mixture, a 2% aqueous hypochlorous acid solution (42.3 mL) was further added dropwise thereto and the mixture was stirred at 35° C. for 2 hours. A 1N aqueous sodium hydroxide solution (250 mL) was added to the reaction mixture and the mixture was poured into ice-water (300 mL) added with sodium sulfite (30 g), followed by stirring of the mixture for 5 minutes. Ether was added thereto to separate it. An aqueous phase was taken, concentrated hydrochloric acid was added thereto to acidify it and ether was added thereto to separate it. The thus obtained organic phase was separated and dried over anhydrous magnesium sulfate. After filtration, the solvent was evaporated under reduced pressure to obtain 4-(4-cyclopropylphenyl) butyric acid (15.8 9, yield: 88%) as a white solid.

Reference Example 10

4-(4-Fluorophenyl)butyric acid

The reaction was carried out in the similar manner to Reference example 6 using 4-fluorobenzaldehyde to obtain the title compound (yield: 71%).

Reference example 11

4-(4-Trifluoromethylphenyl)butyric acid

The reaction was carried out in the similar manner to Reference example 4 using 4-(trifluoromethyl)benzaldehyde to obtain the title compound (yield: 53%).

Reference example 12

4-(4-Cyanophenyl)butyric acid

The reaction was carried out in the similar manner to Reference example 4 using 4-cyanobenzaldehyde to obtain the title compound (yield: 79%).

Reference example 13

4-(3-Methyl-4-methoxyphenyl)butyric acid

[2-(1,3-Dioxolan-2-yl) ethyl]triphenylphosphonium bromide (28.2 9, 63.8 mmol) was suspended in tetrahydrofuran (100 mL) and a solution of potassium t-butoxide (7.15 9, 63.8 mmol) in tetrahydrofuran (100 mL) was added thereto under nitrogen atmosphere over 30 minutes, followed by stirring of the mixture under ice-cooling for 30 minutes. A solution of 4-methoxy-3-methylbenzaldehyde (8.2 mL, 60.6 mmol) in tetrahydrofuran (100 mL) was added thereto over 20 minutes and the mixture was stirred under ice-cooling for 20 minutes. A saturated aqueous ammonium chloride solution was added to the reaction mixture to stop the reaction and ethyl acetate was added thereto to separate it. The thus obtained organic phase was separated, washed with water and a saturated aqueous NaCl solution dried over anhydrous magnesium sulfate. After filtration, the solvent was evaporated under reduced pressure and the residue was purified by silica gel chromatography (hexane:ethyl acetate, 15:1-10:1) to obtain a crude product (14.9 9). 10% Palladium-carbon (5.00 9, 50% moisture) was added to a solution of the obtained crude product (14.9 g) in ethanol (100 mL) and the mixture was stirred at room temperature under a hydrogen atmosphere for 2 hours. After the palladium-carbon in the reaction mixture was Celite-filtered, the filtrate was evaporated under reduced pressure. The residue was purified by silica gel chromatography (hexane:ethyl acetate, 10:1) to obtain [1-(1,3-dioxolan-2-yl)-3-(4-methoxy-3-methylphenyl)]propane (12.8 g, yield: 85%). A 3N aqueous hydrochloric acid solution was added dropwise to a solution of the obtained [1-(1,3-dioxolan-2-yl)-3-(4-methoxy-3-methylphenyl)]propane (12.8 g, 54.0 mmol) in THF (200 mL) and the mixture was stirred for 2 hours. Water (400 mL) and ethyl acetate (300 mL) were added to the reaction mixture to separate it. The thus obtained organic phase was separated, washed with water and a saturated aqueous NaCl solution and dried over anhydrous sodium sulfate. After filtration, the solvent was evaporated under reduced pressure to obtain 4-(3-methyl-4-methoxyphenyl)butanaldehyde (8.42 g, 81%). An aqueous solution (50 mL) of sulfamic acid (7.8 9, 0.08 mol) and an aqueous solution (50 mL) of sodium chlorite (9.2 g, 0.10 mol) were added to a solution of 4-(3-methyl-4-methoxyphenyl)butanaldehyde (8.42 9, 43.8 mmol) in dioxane (100 mL) under ice-cooling and the mixture was stirred at room temperature for 1 hour. Ethyl ether (200 mL) was added to the reaction mixture to separate it. After the pH of the aqueous phase was brought to 3 to 4 by 1N hydrochloric acid, ethyl acetate was added thereto to separate it. The thus obtained organic phase was separated, washed with a saturated aqueous NaCl solution and dried over anhydrous sodium sulfate. After filtration, the solvent was evaporated under reduced pressure to obtain 4-(3-methyl-$^4$-methoxyphenyl)butyric acid (5.38 g, yield: 60%).

TEST EXAMPLES

Test Example 1

Measurement of Rat Peripheral Blood Lymphocyte Count
(1) LEW rats (males, age 5 weeks, Japan Charles River) were used in groups of 5 animals per group.
(2) Administration of Compounds The compounds were suspended in 1% tragacanth liquid (solvent). The suspended compounds were orally administered to the rats using a gastric tube in a dose of 5 mL per kg of body weight. Furthermore, the solvent was administered instead of the suspended compounds to a normal control group.
(3) Measurement of Peripheral Blood Lymphocyte Count Blood samples were collected from the descending vena cava under ether anesthesia 3 hours after administration of the solvent or suspended compounds, and then transferred to tubes containing EDTA.

The absolute lymphocyte counts were measured for the collected blood samples using a hematology testing device. Lymphocyte count lowering activity of the test compounds was calculated as a relative value (%) based on a value of 100% for the lymphocyte count of the normal control group.

| Compound | Lymphocyte Count (Relative Value Based on a value of 100% for Normal Control Group) (%) |
|---|---|
| Example 1 | 8 |
| Example 11 | 11 |
| Comparative Compound 1 | 30 |
| Comparative Compound 2 | 31 |

The compounds of the present invention demonstrated superior activity.

Furthermore, Comparative Compound 1 is a compound described in Japanese Patent Application (Kokai) No. 2002-167382 (Exemplary Compound No. 1-1344, Example 19), while Comparative Compound 2 is an optical isomer of a compound described in Japanese Patent Application (Kokai) No. 2003-267950 (Exemplary Compound No. 1-1082).
[Chemical Formula 31]

Comparative Compound 1

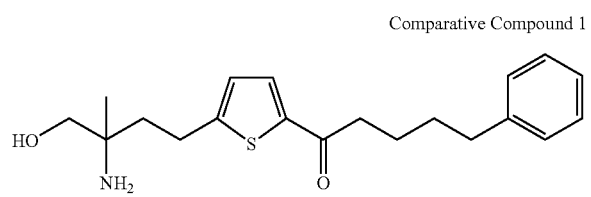

-continued

Comparative Compound 2

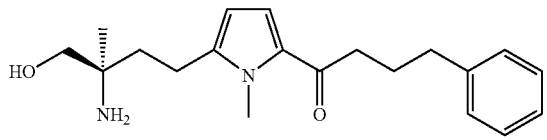

Measurement of $ID_{50}$ of Rat Peripheral Blood Lymphocyte Count (mg/kg)

The inhibition rates for each compound dose group at each dosage were calculated according to the equation below.

Inhibition rate (%) = {1-(lymphocyte count of compound dose group/lymphocyte count of solvent dose group)}×100

The dosage of the compound that yielded a value of 50% for the inhibition rate was calculated as the $ID_{50}$ value.

| Compound | $ID_{50}$ (mg/kg) |
|---|---|
| Example 1 | 0.21 |
| Example 2 | 0.42 |
| Example 11 | 0.39 |
| Comparative Compound 2 | 0.78 |

Test Example 2

Rat Pharmacokinetics (dosage: 1 mg/kg)
(1) LEWIS rats (males, age 6 weeks, Japan Charles River) were used after acclimating for 1 week. 1 to 3 rats were used for each compound.
(2) Administration of Compounds The compounds were dissolved in an aqueous physiological saline solution containing 4% (w/v) sulfobutyl ether β-cyclodextrin. The rats were administered the dissolved compounds directly into the stomach using a metal gastric tube in a dose of 2 mL per kg of body weight.
(3) Measurement of Blood Compound Concentrations Blood samples were collected at 0.1 mL/animal/collection from the jugular vein using heparin as anticoagulant under ether anesthesia at predetermined times after administering the compounds. The blood samples were promptly treated with methanol after collection, and were placed in frozen storage until the time of measurement treatment. After treating the resulting blood samples by solid phase extraction, blood compound concentrations were measured with a high-performance liquid chromatograph-quadropole mass spectrometer. Various pharmacokinetic parameters were then calculated using pharmacokinetics analysis software (Winnonlin Professional) from the resulting blood concentrations.

| Compound | AUC (0–24 h) (ng/mL · h) | Cmax (ng/mL) | T½ (h) |
|---|---|---|---|
| Example 1 | 288 | 19.4 | 15.6 |
| Example 2 | 123 | 8.4 | 8.50 |
| Example 11 | 71.7 | 5.38 | 6.04 |

On the basis of these test results, the pharmaceutical composition of the present invention was determined to demonstrate satisfactory pharmacokinetics.

[Chemical Formula 32]

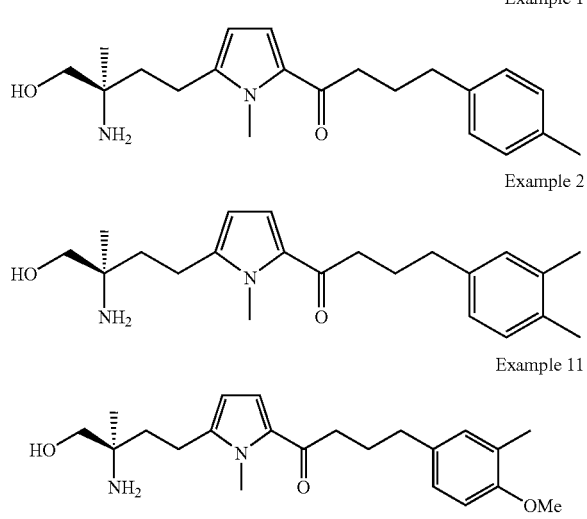

The invention claimed is:

1. A method for suppressing the number of peripheral blood lymphocytes comprising administering to a human in need thereof a pharmaceutically effective amount of a compound which is (2R)-2-amino-2-methyl-4-{1-methyl-5-[4-(4-methylphenyl)butanoyl]pyrrol-2-yl}butan-1-ol or a pharmacologically acceptable salt thereof.

2. The method according to claim 1, wherein the pharmacologically acceptable salt is administered and the pharmacologically acceptable salt is a fumarate salt.

3. The method according to claim 2, wherein the fumarate salt is orally administered to a human adult at a dose of 0.0001 mg/kg to 1 mg/kg.

4. The method according to claim 1, wherein the compound is orally administered to a human adult at a dose of 0.0001 mg/kg to 1 mg/kg.

5. The method according to claim 1, wherein the pharmacologically acceptable salt is administered and the pharmacologically acceptable salt is (2R)-2-amino-2-methyl-4-{1-methyl-5-[4-(4-methylphenyl)butanoyl]pyrrol-2-yl}butan-1-ol hydrochloride.

6. The method according to claim 5, wherein the hydrochloride salt is orally administered to a human adult at a dose of 0.0001 mg/kg to 1 mg/kg.

* * * * *